US009635349B2

(12) United States Patent
Godavarty et al.

(10) Patent No.: US 9,635,349 B2
(45) Date of Patent: Apr. 25, 2017

(54) SECOND GENERATION HAND HELD OPTICAL IMAGER

(75) Inventors: Anuradha Godavarty, Miami, FL (US); Joseph DeCerce, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 909 days.

(21) Appl. No.: 13/703,270

(22) PCT Filed: Jun. 13, 2011

(86) PCT No.: PCT/US2011/040184
§ 371 (c)(1),
(2), (4) Date: Dec. 10, 2012

(87) PCT Pub. No.: WO2011/156810
PCT Pub. Date: Dec. 15, 2011

(65) Prior Publication Data
US 2013/0169759 A1 Jul. 4, 2013

Related U.S. Application Data

(60) Provisional application No. 61/354,130, filed on Jun. 11, 2010.

(51) Int. Cl.
*H04N 13/00* (2006.01)
*H04N 5/253* (2006.01)
(Continued)

(52) U.S. Cl.
CPC ....... *H04N 13/0239* (2013.01); *A61B 5/0073* (2013.01); *A61B 5/0091* (2013.01);
(Continued)

(58) Field of Classification Search
USPC .................................. 348/42, 43, 46–51, 77
See application file for complete search history.

(56) References Cited

U.S. PATENT DOCUMENTS

| 5,730,133 A | 3/1998 | Godik |
| 5,830,145 A | 11/1998 | Tenhoff |

(Continued)

FOREIGN PATENT DOCUMENTS

| DE | 102005058598 A1 | 7/2006 |
| EP | 1797818 A2 | 6/2007 |

(Continued)

OTHER PUBLICATIONS

Culver et al., Three-Dimensional Diffuse Optical Tomography in the Parallel Plane Transmission Geometry: Evaluation of a Hybrid Frequency Domain/Continuous Wave Clinical System for Breast Imaging, Medical Physics, 30(2):235-47 (Feb. 2003).

(Continued)

*Primary Examiner* — Nigar Chowdhury
(74) *Attorney, Agent, or Firm* — Marshall, Gerstein & Borun LLP

(57) ABSTRACT

A method, apparatus, and system acquire data to create a 3D mesh representing a 3D object. The method, apparatus, and system acquire image data of the 3D object using two probes of an imaging system. The flexible probes conform to the shape of the 3D object, illuminate the object at a face of each probe head via optical fibers coupled to an illumination system, and receive at the surface of the 3D object, via optical fibers coupled to a detection system, light reflected from and/or transmitted through the 3D object. The reflectance and transillumination image data collected by the detection system are co-registered with the previously (Continued)

acquired 3D mesh using data from a tracking system monitoring the position of each probe, displayed in real-time, and optionally saved.

23 Claims, 35 Drawing Sheets

(51) Int. Cl.
 *H04N 13/02* (2006.01)
 *A61B 5/00* (2006.01)
 *G06T 17/20* (2006.01)
(52) U.S. Cl.
 CPC .......... *A61B 5/4312* (2013.01); *G06T 17/20* (2013.01); *G06T 2210/41* (2013.01)

(56) References Cited

U.S. PATENT DOCUMENTS

| | | | |
|---|---|---|---|
| 5,971,997 | A | 10/1999 | Guthrie et al. |
| 6,795,195 | B1 | 9/2004 | Barbour et al. |
| 6,808,289 | B2 | 10/2004 | Reed |
| RE38,800 | E | 9/2005 | Barbour |
| 8,070,682 | B2 | 12/2011 | Zhu |
| 8,712,504 | B2 | 4/2014 | Godavarty et al. |
| 2002/0045811 | A1 | 4/2002 | Kittrell et al. |
| 2002/0050988 | A1 | 5/2002 | Petrov et al. |
| 2004/0215072 | A1 | 10/2004 | Zhu |
| 2004/0254464 | A1 | 12/2004 | Stribling |
| 2005/0004453 | A1 | 1/2005 | Tearney et al. |
| 2005/0116179 | A1 | 6/2005 | Aguirre et al. |
| 2007/0219450 | A1 | 9/2007 | Azar et al. |
| 2008/0294056 | A1 | 11/2008 | Boutet et al. |
| 2009/0240145 | A1* | 9/2009 | Otsuka ............... A61B 8/0875 600/439 |
| 2009/0306521 | A1 | 12/2009 | Ermakov et al. |
| 2010/0010340 | A1 | 1/2010 | Godavarty et al. |
| 2010/0078576 | A1 | 4/2010 | Ntziachristos et al. |
| 2010/0155599 | A1 | 6/2010 | Godavarty et al. |
| 2010/0256496 | A1* | 10/2010 | Zhu ..................... A61B 5/0091 600/459 |
| 2010/0324423 | A1* | 12/2010 | El-Aklouk ........... A61B 8/4488 600/444 |
| 2011/0190639 | A1 | 8/2011 | Peltie et al. |
| 2011/0229840 | A1 | 9/2011 | Liang et al. |
| 2014/0364743 | A1 | 12/2014 | Godavarty et al. |
| 2015/0190061 | A1 | 7/2015 | Godavarty et al. |

FOREIGN PATENT DOCUMENTS

| | | | |
|---|---|---|---|
| WO | WO-94/24927 A1 | 11/1994 | |
| WO | WO-99/24927 A1 | 5/1999 | |
| WO | WO 2008039988 A2 * | 4/2008 | ........... A61B 5/0091 |
| WO | WO-2011/156810 A2 | 12/2011 | |

OTHER PUBLICATIONS

Ge et al., A Novel Optical Imager Towards Breast Cancer Diagnosis, Medical Physics, 33(6):1989 (Jun. 2006).
Godavarty et al., Fluorescence-Enhanced Optical Imaging of Large Phantoms Using Single and Simultaneous Dual Point Illumination Geometries, Medical Physics, 31(2):183-90 (Feb. 2004).
International Preliminary Report on Patentability, International Application No. PCT/US2011/040184, Dec. 14, 2012.
International Search Report and Written Opinion, International Application No. PCT/US2011/040184, mailed Jan. 19, 2012.
Jayachandran, B. et al., Design and Development of a Hand-Held Optical Probe Toward Fluorescence Diagnostic Imaging, J. Biomedical Optics, 12(5):054014-1-10 (2007).
Regalado et al., Automated coregistered imaging using a hand-held probe-based optical imager, Rev. Sci. Instrum., 81:023702 (2010).
Supplementary Partial European Search Report, European patent application No. EP 11793309, Jul. 30, 2015.
Zhu et al., Ultrasound-guided optical tomographic imaging of malignant and benign breast legions: initial clinical results of 19 cases, Neoplasia, 5(5):379-86 (2003).
Extended European Search Report issued in European Pat. Appl. No. 11793309.3 dated Nov. 20, 2015.

* cited by examiner

| Imaging Modality | Principle | Advantages | Disadvantages |
|---|---|---|---|
| X-ray | Uses x-rays of ~ 50 KeV photons to detect the x-rays attenuated by tissues of differing densities | Excellent resolution Good penetration depth | Ionizing radiation Poor contrast among soft tissues Overlooks 10% of breast cancer in non-calcified lesions |
| Computer Tomography (CT) | Uses x-rays at different angles for cross-sectional views | Same as x-ray technique, but provides more information | Greater exposure to x-ray radiation |
| Ultrasound (US) | Uses high frequency sound waves to detect the reflectance and transmittance from acoustically dissimilar tissues | Non-ionizing radiation Inexpensive Portable, safe, and versatile | Poor imaging quality Poor contrast |
| Magnetic resonance imaging (MRI) | Uses strong magnetic fields and RF waves to detect the emitted RF waves and relaxation of spin state of nuclei in tissues | Non-ionizing radiation Functional imaging Soft-tissue contrast Good resolution Good penetration depth | Strong magnetic field Expensive Not portable Slow process |

Figure 1

Projection-Shadow

Circular

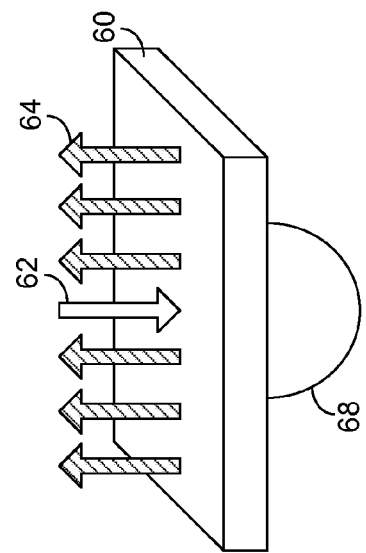
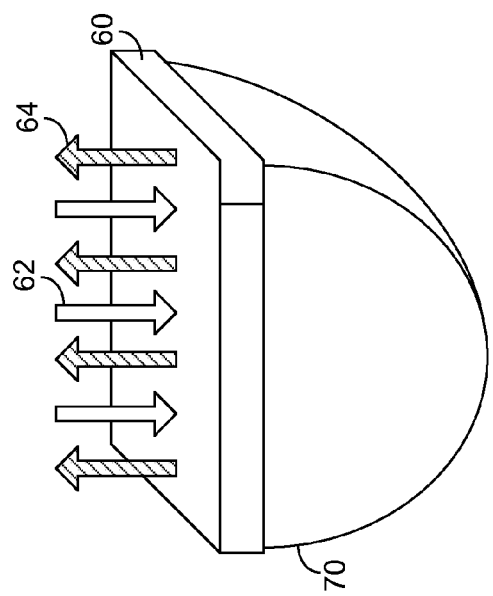
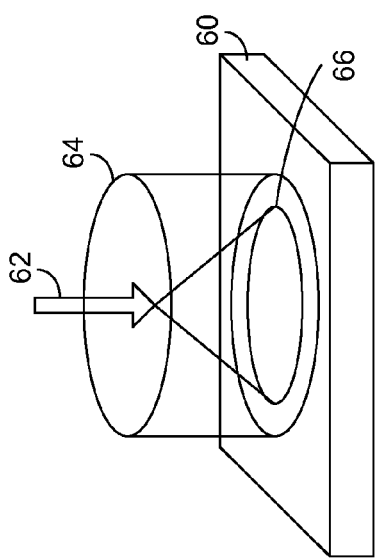
Figure 9A
Figure 9B
Figure 9C

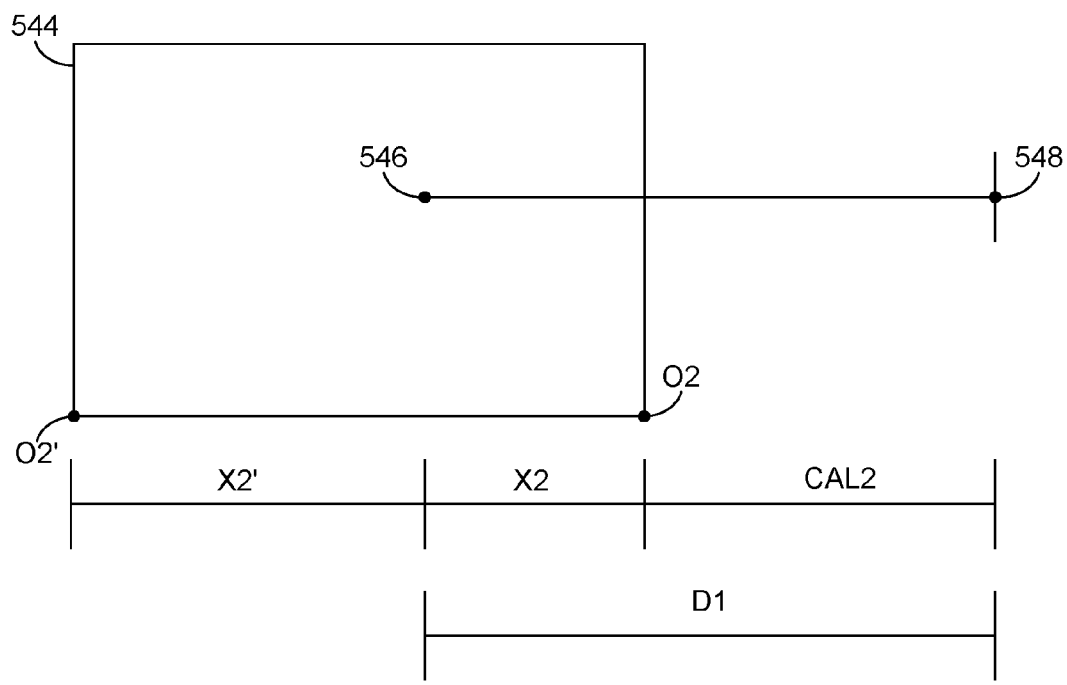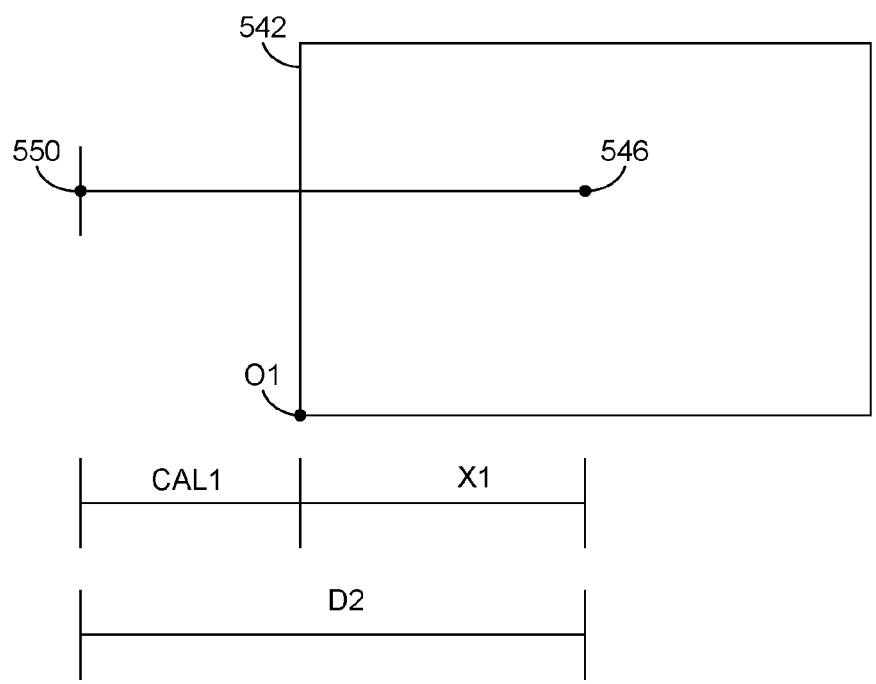
Figure 25

SECOND GENERATION HAND HELD OPTICAL IMAGER

RELATED APPLICATIONS

This application claims priority under 35 U.S.C. §119(e) to U.S. Provisional Application No. 61/354,130, filed Jun. 11, 2010, entitled "Second Generation Hand Held Optical Imager." This application is also related to: U.S. Provisional Patent Application 60/847,812, filed Sep. 28, 2006; International Patent Application PCT/US07/079,906, filed Sep. 28, 2007; U.S. Provisional Patent Application 61/118,326, filed Nov. 26, 2008; U.S. patent application Ser. No. 12/442,505, filed Jun. 26, 2009; and U.S. patent application Ser. No. 12/645,476, filed Nov. 24, 2009. The contents of each of the related applications is hereby incorporated by reference herein.

STATEMENT REGARDING FEDERALLY SPONSORED RESEARCH OR DEVELOPMENT

This invention was made with government support under R15-CA119253, awarded by the National Institutes of Health. The government has certain rights in the invention.

BACKGROUND

Existing diagnostic imaging techniques of breast cancer include X-ray mammography, computer tomography (CT), ultrasound, magnetic resonance imaging (MRI), and nuclear imaging. FIG. 1 illustrates a table summarizing the advantages and disadvantages of each existing diagnostic imaging process or technique. These conventional techniques may be limited by poor resolution, use of harmful ionizing radiation, lack of portability, and/or expensive instrumentation.

Near-infrared (NIR) optical imaging is an emerging non-invasive technology that may be applied towards deep tissue imaging, with one application being breast cancer diagnostics However, the existing NIR optical imaging systems may be limited in a number of ways. For example, existing NIR imaging apparatus may be large and bulky systems, and thus, not generally portable. NIR imaging apparatus may also cause patient discomfort because the apparatus may require a patient to be placed in certain positions or may require compression of patient breast tissue. Moreover, conventional NIR imaging apparatus and methods may be limited to imaging only fixed volumes or certain shapes of breast tissue.

In recent years, hand-held based optical imaging systems have been developed for clinical applications of the imaging technology. These hand-held based systems represent an alternative to the conventional bulky optical imaging systems. However, the hand-held optical imagers available may be limited by having only flat measuring probe heads that cannot conform to different tissue curvatures and/or may not be capable of performing three-dimensional (3D) tomography studies. In addition, each of these optical imagers typically employs single point illumination (e.g., using only a single existing light source or multiple existing light sources in which only a single source is activated at one time) and single/multiple point detection measurement geometries that limit the total data acquisition rates in a clinical environment. Because of the relatively slow data capture rates, patient discomfort and wait time may be further increased.

SUMMARY

A method for performing co-registered optical imaging includes acquiring a three-dimensional (3D) surface outline of the subject to be imaged and representing the 3D surface outline as a discretized mesh. Using two or more probes of a probe assembly, the method acquires an optical signal at a surface of the subject, tracking the probes using one or more markers on each probe of the probe assembly. The method receives from an optical imaging system coupled to the probe assembly, the optical signal captured by the probe assembly, and converts the optical signal to image data. The image data are co-registered with the 3D mesh to form an image.

In some implementations, the method may acquire the 3D surface outline of the subject using an automated mechanism to scan around the subject. The method may acquire optical data comprising data of a reflectance signal, of a trans-illumination signal, and/or of a fluorescence signal. The method may track the subject using a third marker disposed on the subject. Additionally, the method may track the probes and/or the subject using multiple sensors, data from each of which is calibrated using data from the other(s). Further still, the method may track the probes and/or the subject using multiple, orthogonally disposed sensors.

A system for performing co-registered optical imaging includes an illumination assembly operable to output one or more optical signals. The system also includes a probe assembly optically coupled to the illumination assembly and operable to receive the one or more optical signals and to transmit the one or more optical signals into a subject tissue. A tracking system includes an optical marking element and a tracking receiver operable to detect the optical marking element, communicatively coupled to a computing platform. The system further includes an imaging system coupled to the probe assembly and to the computing platform, the imaging system including an imaging sensor operable to receive an optical signal from the subject tissue. A module executable by the computing platform co-registers tracking data received from the tracking system and image data received from the imaging system with a 3D mesh representing the subject tissue.

Where desired, each of the probe heads may include a probe face having an adjustable contour. The system may also include an automatic scanning apparatus for acquiring data of the surface geometry of the subject and an executable module for using the acquired data to create a discretized surface or volumetric 3D mesh.

DESCRIPTION OF THE DRAWINGS

FIG. 1 illustrates a table of existing tumor diagnostic methods indicating principle of operation, advantages and disadvantages;

FIG. 9A illustrates a first configuration for illuminating a tissue surface;

FIG. 9B illustrates a second configuration for illuminating a tissue surface to perform imaging in accordance with the presently described embodiments;

FIG. 9C illustrates a third configuration for illuminating a tissue surface to perform imaging in accordance with the presently described embodiments;

FIG. 25 illustrates 2D coordinate spaces corresponding to each of the two tracking receivers in FIG. 24;

DETAILED DESCRIPTION

General Principles of Operation

Figure 2:
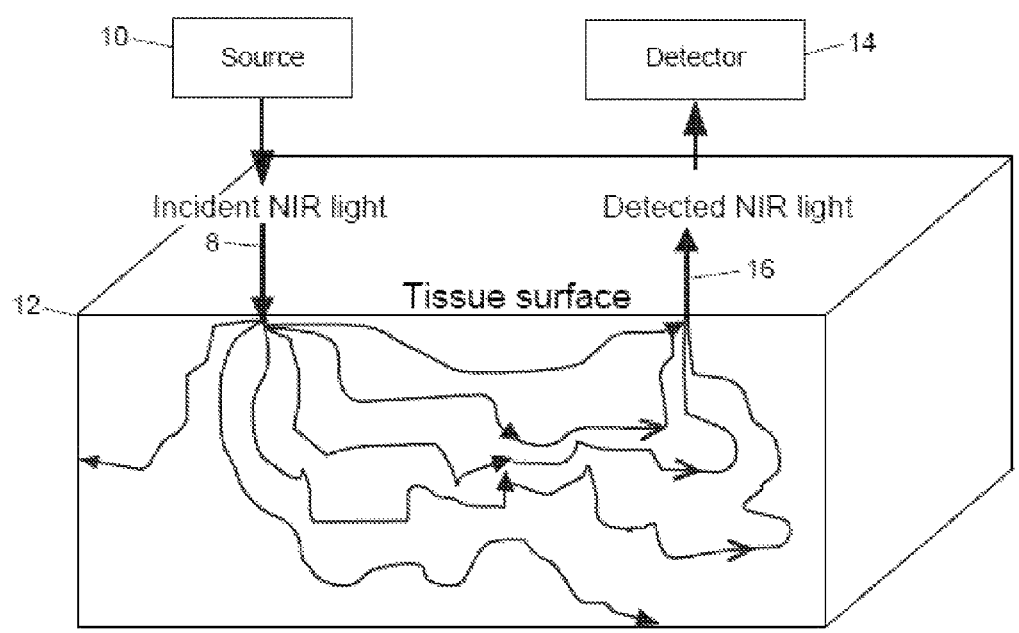
FIG. 2 illustrates a general optical imaging process.

FIG. 2 illustrates general principles behind an optical imaging process. Light 8 from a source 10 is projected on a target tissue 12 at a wavelength of 700-900 nm. The tissue 12 may minimally absorb the light 8 while reflecting and scattering a majority of the light. A corresponding light detector 14 may be positioned to measure characteristics of the reflected light 16, such as intensity, phase, or time delay.

Generally, when NIR light is launched onto a tissue surface, light propagates into the tissue and is minimally absorbed (in biological tissues, hemoglobin and water are least absorbent in the near-infrared spectrum) and preferentially scattered, allowing deep penetration of the light into the tissue and providing an opportunity for diagnostic imaging. The reflected light and/or trans-illuminated light (i.e., light that enters tissue at a first surface and exits the tissue at a second surface opposite the first surface) may be collected at a set of point locations on the tissue surface. From the collected reflected or trans-illuminated measurements, images of scattering ($\mu s$) and absorption ($\mu a$) coefficients of the entire tissue domain may be generated using appropriate light propagation models and reconstruction algorithms (discussed further below). Diffuse optical imaging enables translation of the highly scattered light signals into clinically meaningful information about human tissue. For example, optical properties may be used to locate and identify physiological changes in the tissue that may indicate the existence and/or location of tumors.

Figure 3:
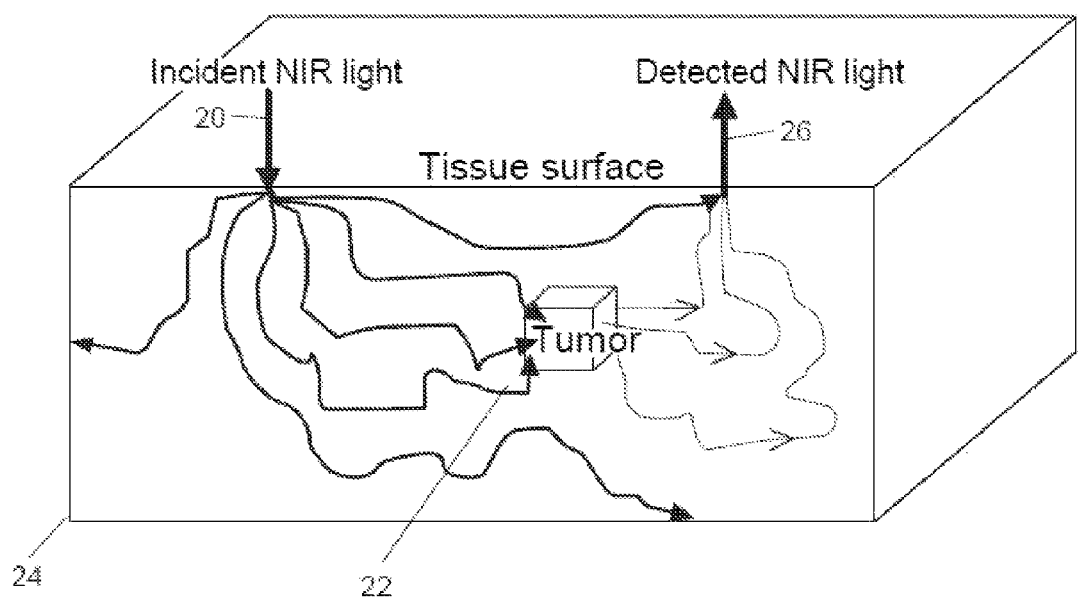
FIG. 3 illustrates a general optical imaging process in tumor detection.

Differences in composition of the tissue may cause a difference in the light characteristics (e.g., in terms of reflected/trans-illuminated light intensity, phase, time delay, etc.) of the imaging data collected. This difference in light characteristics may be used to determine abnormal tissue growth. For example, optical imaging may be used to detect a breast tumor in a chemical environment by looking for two intrinsic cancer signatures: increased blood flow (as shown by the total hemoglobin concentration) and hypermetabolism (as shown by a drop in oxygen concentration). As illustrated in FIG. 3, when NIR light 20 encounters an angiogenic (growth of blood vessels from surrounding tissue to solid tumors) region 22 of a breast tissue 24, light may be absorbed based on the different concentrations of hemoglobin in that area of the breast, thus providing endogenous contrast between normal and tumor tissue. The difference in light characteristics of the collected diffused light 26 may reflect the difference in absorption and/or scattering arising from this angiogenic region 22.

To detect lesions smaller than about 0.5 cm (in diameter) external contrast agents may need to be used in order to improve the optical contrast between normal and diseased tissues in a process known as fluorescence-enhanced optical imaging. Fluorescence-enhanced optical imaging involves the administration of exogenous fluorescent contrast agents that specifically bind to target tissue (e.g., tumor tissue) and that are excitable in the NIR wavelength range. The external fluorescent contrast agents molecularly target the metastatic cancer cells within the breast tissue and enhance the optical contrast between the cancerous cells and the background breast tissue.

Figure 4:
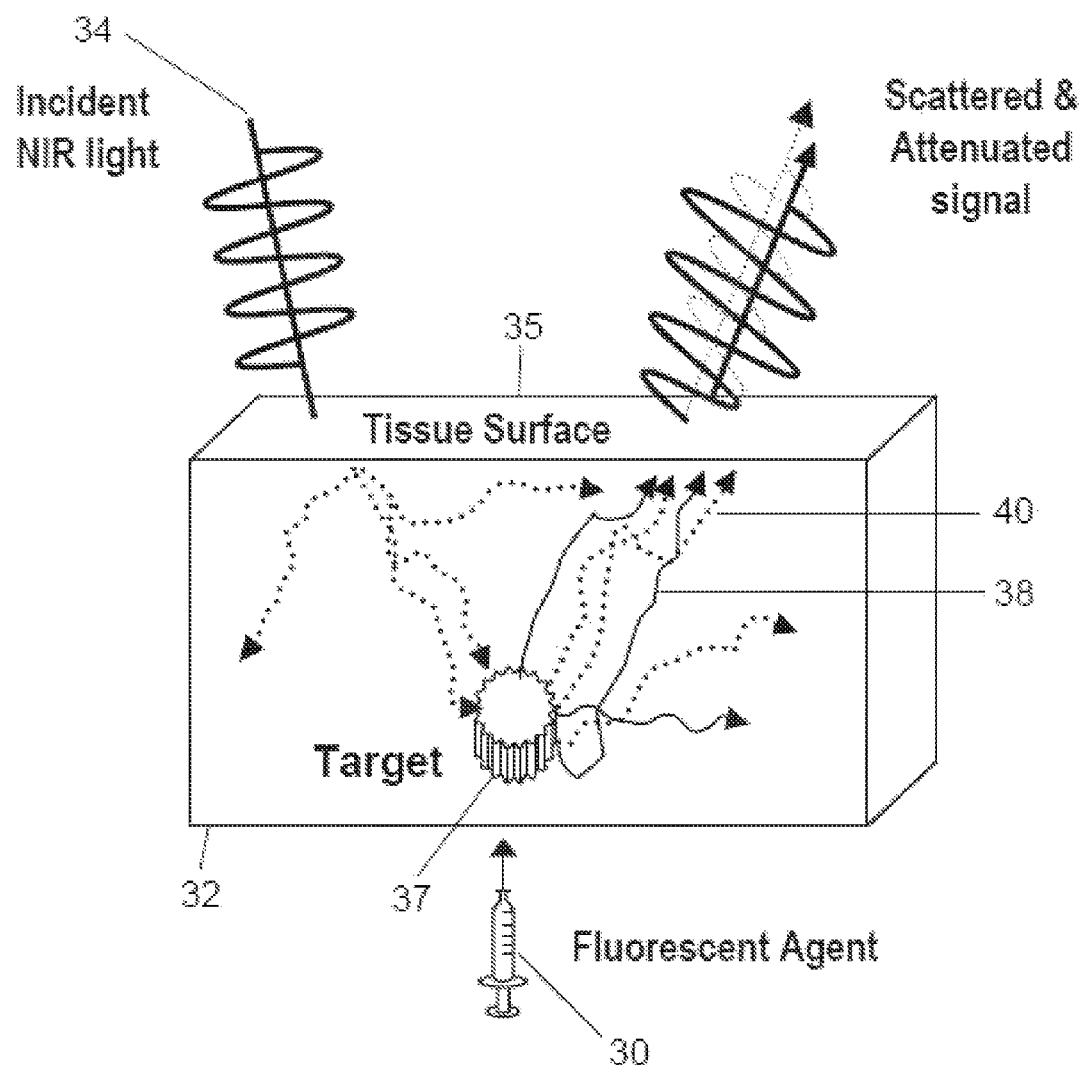
FIG. 4 illustrates a fluorescence enhanced optical imaging process.

FIG. 4 illustrates a fluorescence-enhanced optical imaging process. In a fluorescence-enhanced optical imaging process, a target-specific florescent contrast agent 30 may be injected into the tissue 32. When NIR light 34 (having a wavelength of 700-900 nm) is launched at the tissue surface 35, the minimally-absorbed and preferentially-scattered excitation photons propagate deep into the tissue 32. Upon encountering a fluorescent molecule 37 (e.g., found at the site of target tissue substructure), the photons excite the fluorescent molecule 37 from its ground state to a higher orbital level. After residing at the higher energy orbital for a period (known as the fluorescence lifetime), the fluorescent molecule emits a fluorescent signal 38 at a greater wavelength than the incident NIR light 34. The emitted fluorescent signal 38 along with the attenuated excitation signal 40 (which is at the same wavelength as the incident light) propagates back through the tissue surface where it is detected. At a detection site (not shown in FIG. 4), appropriate optical filters may be used to separate the fluorescence signal from the attenuated excitation signal to provide relevant light characteristic data. FIG. 4 depicts the NIR light 34 as a modulated signal (i.e., implementing a frequency-domain analysis), however the analysis may be conducted in the time domain, in the frequency domain, or in a continuous wave implementation.

Imaging Data Signal Processing

Three distinct measurement techniques may be used to process the collected light characteristic data in optical imaging. These techniques include continuous wave, time-domain photon migration (TDPM), and frequency-domain photon migration (FDPM) based imaging. Each of these measurement techniques has advantages and disadvantages, and the selection of the appropriate technique largely depends on the specific application and requirement.

Continuous wave (CW) measurement technique uses steady state light of constant intensity on the tissue surface and measures the attenuated intensity of the trans-illuminated and/or reflected light. In continuous wave based fluorescent optical imaging the NIR light attenuates due to absorption and scattering in the tissue medium. Upon encountering the florescent molecule, a steady state florescent signal is emitted, which attenuates before it is detected at the tissue surface. Continuous wave-based imaging instrumentation is relatively simple and involves low-cost optical components. The major disadvantages of continuous wave measurement technique include difficulty in resolving tissue absorption from scattering and inability to image the fluorescence decay kinetics. When independent measurements of tissue optical properties (i.e. absorption, scattering or fluorescence lifetime) and/or depth information are required, the use of TDPM or FDPM measurement techniques may be necessary.

TDPM measurement techniques illuminate tissue with ultra fast (e.g., in the femtosecond to picosecond time range) photon pulses and resolve the arrival of the photons as a function of time at different locations around the tissue boundary. In a TDPM-based fluorescent optical imaging process the excitation light pulse broadens and attenuates as it travels through the scattering medium. Upon encountering a fluorescent molecule, a fluorescent light pulse is emitted, which broadens and attenuates as it propagates in the tissue medium. This broadened pulse of fluorescent light is further broadened and attenuated due to absorption and scattering in the tissue medium, before it is detected at the tissue surface using, for example, fluorescence optical imaging.

The TDPM measurement technique may provide better depth information compared to a continuous wave measurement technique. Although TDPM-based measurements provide a wealth of information that may be used to map optical properties of tissues, TDPM measurement techniques may be limited by their large signal-to-noise ratio (SNR) range, which may require significant data acquisition times compared to CW and FDPM measurement techniques.

In FDPM-based fluorescence optical imaging, modulated excitation light is launched onto the tissue surface and the modulated fluorescent signal is detected at the tissue surface in terms of amplitude and phase shift. Measurements of the light intensity and the phase shift of the photon wave-front are obtained with respect to the source light information about the tissue optical properties and fluorochrome distribution. Frequency domain measurement technique may be preferable over TDPM measurement technique due to its inexpensive instrumentation. In addition, the steady-state FDPM measurements in terms of amplitude and phase shift are minimally corrupted by ambient light, since the instrument detects only a modulated signal. Thus, the FDPM instrument automatically acts as a filter for ambient light rejection, which is an advantage of FDPM measurement techniques over continuous wave or TDPM measurement techniques. However, FDPM measurement techniques require frequencies of several hundred MHz or higher to achieve depth information that may be difficult to obtain using continuous wave technique. In practice, usually a single frequency may be employed, and the phase shift may be used to estimate the mean time of flight of the photons. However, data obtained at multiple frequencies may improve FDPM imaging performance and may be equivalent to TDPM data via the inverse Fourier Transform.

While some embodiments are described as implementing fluorescence-based imaging, it should be understood that any of the embodiments herein may implement imaging with or without fluorescence and, in particular, may implement NIR imaging in addition to, or instead of, fluorescence based imaging.

Source and Detector Configurations for Optical Imaging

NIR-based imaging approaches, whether based on endogenous or exogenous contrast, involve trans-illumination and/or reflection measurements. These measurements represent the light propagation between light sources and detector sensor pairs, and are based on excitation illumination and excitation/emission detection. Generally, trans-illumination is the shining of a light through a target tissue, such as breast tissue, to observe the absorption pattern from a different surface of the tissue medium. Reflection measurements involve observing light reflected off a tissue surface from the same side as the incident light.

Generally, existing optical imaging configurations for arranging sources (for providing incident/excitation signals) and detectors (for collecting reflected and/or trans-illuminated NIR signals, fluorescence or non-fluorescence signals) may be broadly categorized into projection shadow, circular, and sub-surface/reflective configurations.

Figure 5:
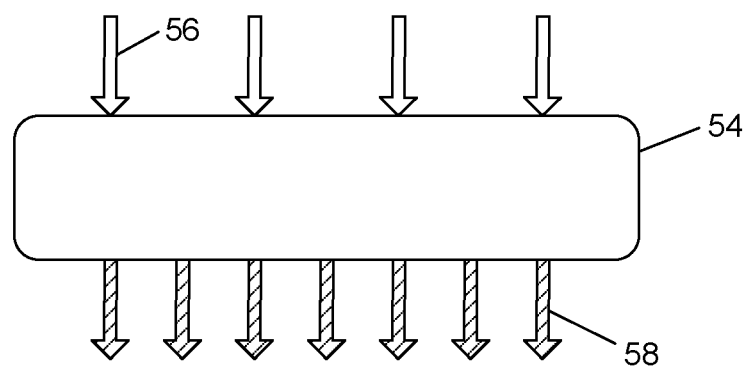
FIG. 5 illustrates a projection-shadow optical imaging process.

FIG. 5 illustrates a projection-shadow optical imaging process. Projection-shadow imaging involves collecting trans-illuminated light from the tissue object. Trans-illuminated light may refer to light that traverses a surface(s) of a tissue. In trans-illumination method, sources 56 and detectors 58 are placed on opposite sides of breast tissue 54. In this geometry, single/multiple sources may be deployed on an opposite plane that is parallel to the detector plane that has single/multiple detectors. Optical properties of the three dimensional tissue are obtained between the source and the detector planes. This method generally requires compression of the target tissue. The compressed tissue configuration may be analogous to x-ray mammography, and may be disadvantageous due to patient discomfort caused by tissue compression and due to limited information obtained for the entire breast tissue.

Figure 6:
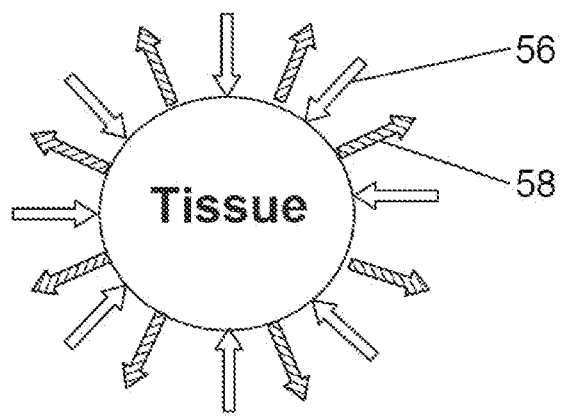
FIG. 6 illustrates a circular imaging process.

FIG. 6 illustrates a circular imaging process, wherein both the reflected and trans-illuminated light is collected along a circular circumference of the tissue. In this configuration, multiple sources 56 and detectors 58 are disposed about the circular circumference of the tissue. The circular configuration may be minimally uncomfortable to a patient, but is limited by the bulky and non-portable size of the apparatus.

Figure 7:
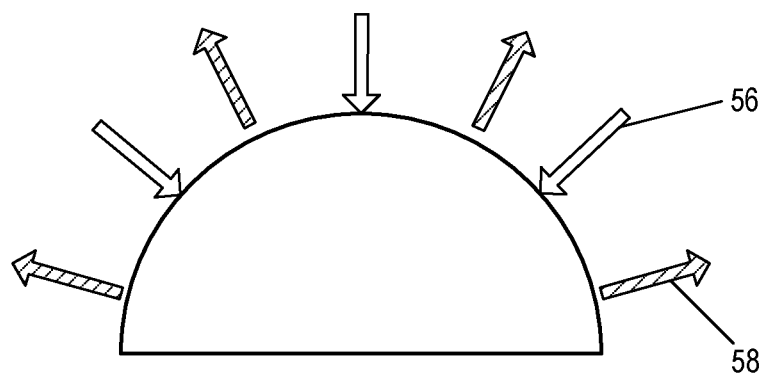
FIG. 7 illustrates general sub-surface imaging.

FIG. 7 illustrates sub-surface imaging, which may involve collecting reflected and/or trans-illuminated light using multiple sources 56 and detectors 58. This configuration requires no tissue compression, and may be designed to mimic a hand-held imaging probe. Many known commercial optical imaging systems and hand-held probes developed using the sub-surface imaging configuration are designed to only collect reflected light using flat measurement probe heads.

Three-dimensional tomography studies may be performed using the projection-shadow or the circular imaging configuration. However, 3D tomography studies have been limited by the sub-surface configuration because of the limited depth information obtainable in the absence of trans-illuminated measurements, and also from lack of co-registering the source and detector locations on the target tissue object that is imaged.

Illumination Area

There are essentially three methods of illuminating a tissue surface 60: (1) wide-area illumination as illustrated in FIG. 9A (2) sequential, single-point illumination as illustrated in FIG. 9B, and (3) sequential or simultaneous, multi-point illumination as illustrated in FIG. 9C. In each, one or more illumination sources 62 illuminate the tissue surface 60 and receive one or more trans-illumination, reflection, or fluorescence signals or NIR signals 64. In wide-area illumination such as that illustrated in FIG. 9A, the intensity of the illumination from the illumination source 62 is typically not uniform (e.g., the intensity may typically be relatively higher at the center than at the edges of the illuminated region 66). To date, most optical imaging studies have typically been performed using sequential single point illumination (FIG. 9C) and sequential or simultaneous multiple-point detection measurement techniques (FIG. 9B). Although the data acquisition rates are enhanced upon using simultaneous point detection techniques, in terms of illumination geometries, most optical imaging studies have been limited to using sequential single point illumination (FIG. 9C) of the tissue surface 60 during imaging. For sub-surface optical imaging, a point illumination system (FIGS. 9B and 9C) vastly reduces variations in intensity on the imaging surface overcoming one of the limitations posed by wide area illumination as shown in FIG. 9A. However, illumination by excitation light from a single point 62 (FIG. 9C) interrogates a relatively small portion 68 of tissue volume, thus increasing the total data acquisition times in order to image the entire tissue volume. In addition, use of simultaneous illumination has the potential to illuminate a larger area and potentially to illuminate to a greater depth, and may therefore provide relatively faster and/or more accurate tomographic reconstruction.

Probe Heads

Figure 10:
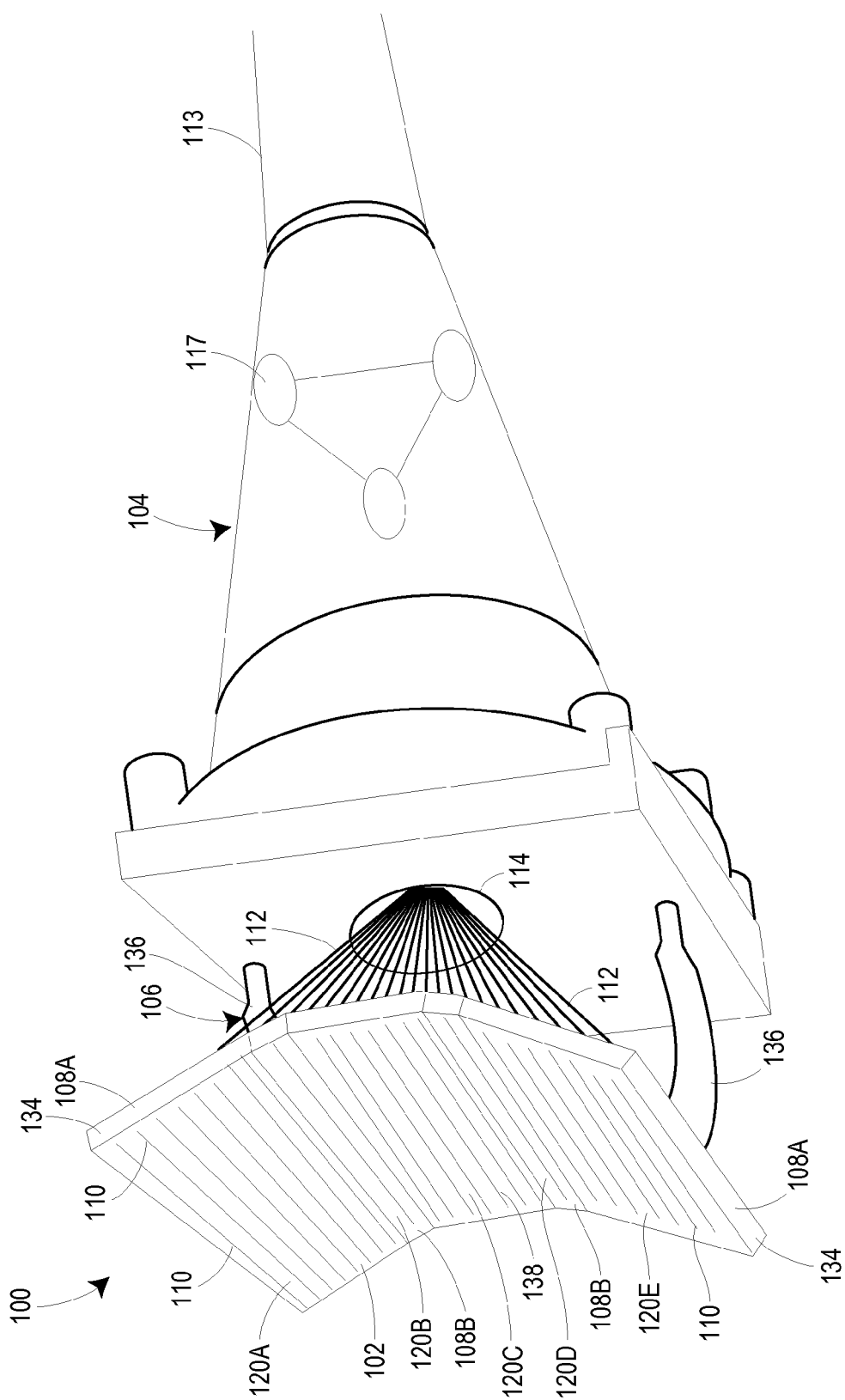
FIG. 10 illustrates a probe head in accordance with the presently described embodiments.

FIG. 10 depicts an embodiment of an improved probe head 100. The probe head 100 comprises a probe face 102, a handle portion 104, and an adjustment mechanism 106. The probe face 102 may be comprised of a number of separate surfaces 108A and 108B. For example, in FIG. 10, the probe face 102 is depicted as comprising three primary surfaces 108A and two connective surfaces 108B. Of course, the probe face 102 is not limited to the configuration depicted, and other arrangements of surfaces may be conceived without departing from the spirit of this disclosure. For example, the probe face 102 may have five or more surfaces 108A and no surfaces 108B. Alternatively, the probe face 102 may be formed from a number of smaller, tile-shaped surfaces (not shown) which would provide even greater contouring flexibility.

Each of the surfaces 108A, 108B of the probe face 102 includes a plurality of apertures 110. The apertures 110 allow the transmission of light through the probe face 102. Each of the apertures 110 may be coupled to an optical fiber 112 for carrying an optical signal to or from the probe face 102. Some of the apertures 110, for example, may be optically coupled to one or more illumination sources to illuminate a tissue sample, while others of the apertures 110 may be optically coupled to one or more imaging devices, such as a charge-coupled device (CCD) to transmit light received at the aperture 110 to the CCD, thereby capturing an image. Collectively, the optical fibers 112 may be bundled to form an optical fiber cable 113, which may pass through the handle portion 104 via a hole 114 therein. (Throughout the remainder of this description, the phrase "optical fiber cable(s)" is used interchangeably with the phrase "fiber optical cable(s).") The optical fiber cable 113 may include a first bundle of optical fibers for illumination (optically coupled to point illumination sources, such LEDs or laser diodes, as described below) and a second bundle of optical fibers for detection (optically coupled to the detector/CCD). Alternatively, optical fibers 112 coupled to one or more sources may pass through the handle portion 104 of the probe head 100 as individual fibers, while optical fibers 112 coupled to one or more detectors may be bundled to form the optical fiber cable 113.

Figure 11:
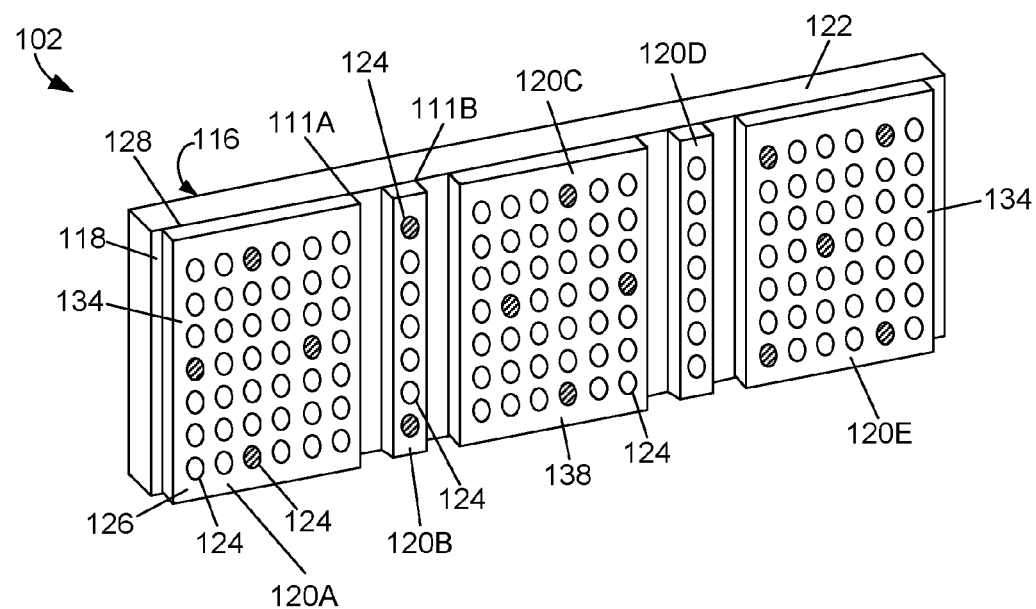
FIG. 11 is a rear perspective view of a probe face of the probe head of FIG. 10.

The probe face 102, comprising the surfaces 108A, 108B is preferably formed of a soft, flexible material, such as silicone, and contoured to smoothly cover the transitions between the surfaces 108A, 108B. FIG. 11 illustrates an embodiment of the probe face 102, viewed from the back. The probe face 102 includes a tissue contact surface 116, a support contact surface 118, and a plurality of termination structures 120A-E. The termination structures 120A-E provide a terminus for each of the optical fibers 112, and support the optical fibers as the probe face 102 contours to the shape of the tissue sample (e.g., to the shape of a breast being examined).

Each of the termination structures 120A-E may be formed of a rigid material such as, and without limitation, aluminum, acrylic, or a shape memory alloy. In some embodiments, each of the termination structures 120A-E may be coupled to one or more other of the termination structures 120A-E. In some or additional embodiments, each of the termination structures 120A-E may be fused to a material 122 (e.g., silicone) forming the tissue contact surface 116 and the support contact surface 118. In any event, each of the termination structures 120A-E has a plurality of apertures 124 extending therethrough from a first planar surface 126 to a second planar surface 128 in contact with the support contact surface 118. Each of the apertures 124 is configured to receive one of the optical fibers 112, and to support the optical fiber 112 as it extends into or through the material 122 to terminate at or near the tissue contact surface 116.

Figure 13:
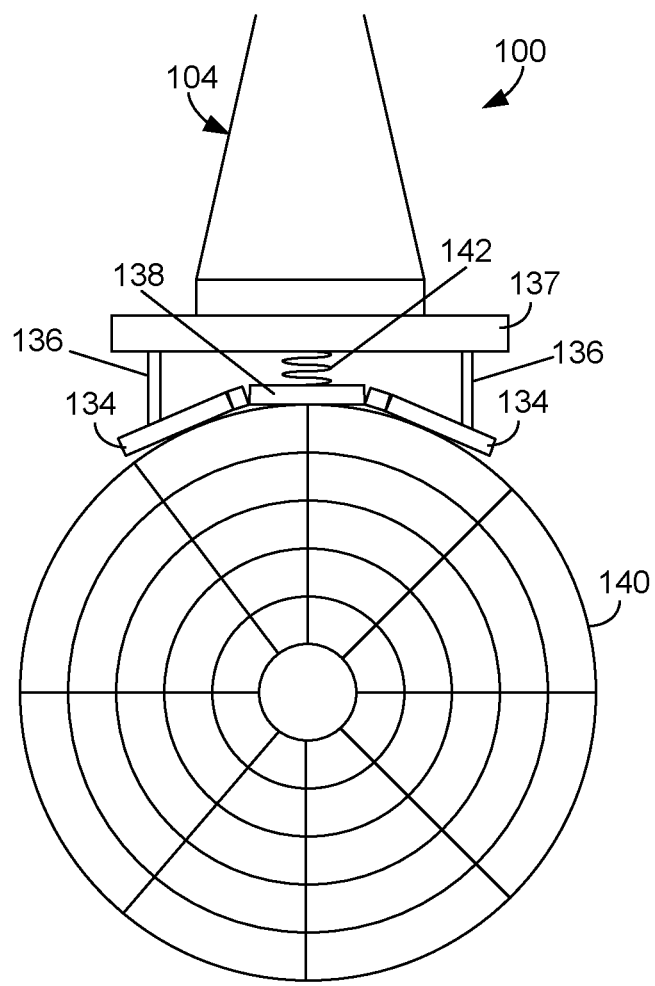
FIG. 13 is a schematic depiction of the probe head of FIG. 10.

As illustrated in FIG. 11, the multiple termination structures 120A-E may be pivotably coupled to one another. In the embodiment of FIG. 11, a first of the termination structures 120A may be pivotably coupled at an end 111A with a second of the termination structures 120B. The second termination structure 120B may be pivotably coupled at an end 111B to a third of the termination structures 120C, such that the termination structures 120A-E are all pivotably coupled to adjoining termination structures 120A-E by the flexible material 122. In this embodiment, surface 116 forming the probe face 102 may conform to a surface being probed, such as a breast tissue or any other body part, as illustrated in FIG. 13. This curved geometry of the optical probe embodiment enables improved contact of the source-detector array with the object being imaged, which may provide greater accuracy of the measured data.

In some embodiments, the optical fibers 112 may terminate at the material 122 without the need for one or more separate termination structures such as the termination structures 120.

Figure 12:
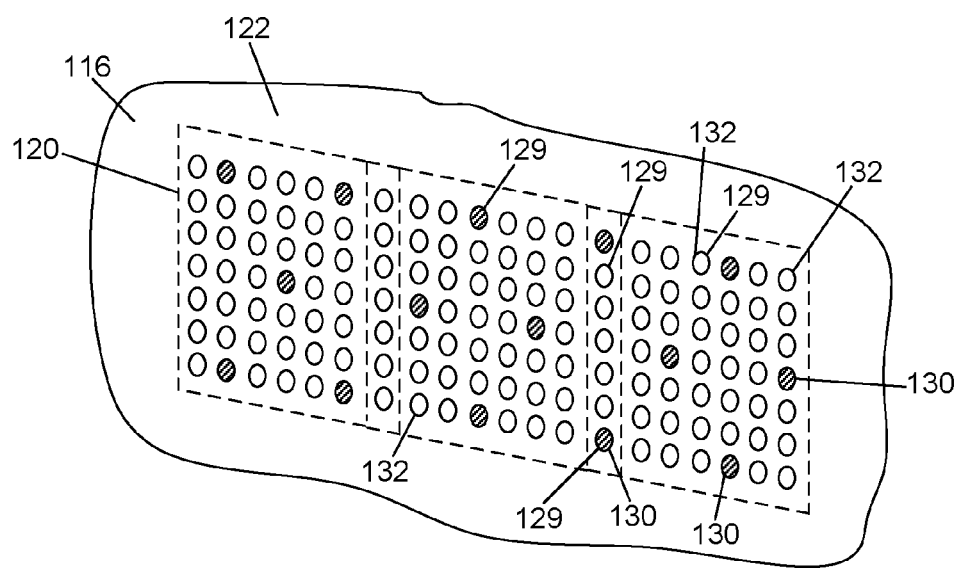
FIG. 12 is a front perspective view of the probe face of FIG. 11.

FIG. 12 illustrates a front view of the probe face 102. The material 122 may comprise the surface 116, which may be smooth and free of sharp edges for patient comfort. The material 122 may have formed in it a plurality of apertures 129 generally aligned with the apertures 124 of the structures 120. In FIGS. 11 and 12, the apertures 124, 129 are depicted as including illumination apertures 130 and detection apertures 132. Each of the illumination apertures 130 is optically coupled to an optical fiber 112 extending to an illumination source (described below). Each of the detection apertures 132 is optically coupled to an optical fiber 112 extending to a detection device (described below). Of course, the configuration of source and detector apertures depicted in FIGS. 11 and 12 is not intended to be limiting, and other embodiments may include different ratios of source and detector apertures. For example, in an embodiment, each of the structures 120A, 120C, and 120E includes a single source aperture, and 26 detection apertures. In some embodiments, the dimensions of the probe face 102 are approximately 4 cm×5 cm, and the tissue contact surface 116 has a surface area of approximately 20 cm$^2$.

Various mechanisms may allow the probe face 102 to conform to the sample tissue. For example, in an embodiment the outer portions 134 (or outer edges) (see FIGS. 10, 11, 13) may be supported by support structures 136 fixedly coupled to a plate 137 of the handle portion 104 of the probe head 100, while one or more central portions 138 may be movably (and, optionally, resiliently) coupled to the plate 137 of the handle portion 104 of the probe head 110 by a member 142, such that a pressure applied to the central portion 138 (e.g., by a breast tissue 140, as in FIG. 13) causes the central portion 138 to move relative to the outer portions 134 to conform to the contour of the tissue sample. In another embodiment, each termination structure 120 may be independently, movably coupled to the handle, portion 104 (possibly by multiple support structures 136, 142) such that the probe face 102 as a whole adjusts to the contour of the tissue sample. Other embodiments may employ arrangements of termination structures, sample contact materials (e.g., the material 122), and support structures, cooperating to effectuate a flexible probe face 102, without departing from the scope of this disclosure, and any probe head implementing an optical point-illumination and detection scheme and having a probe face adapted for smooth, contouring engagement with the sampled tissue may be used in the probe assemblies, systems, and methods described below.

Figure 8:
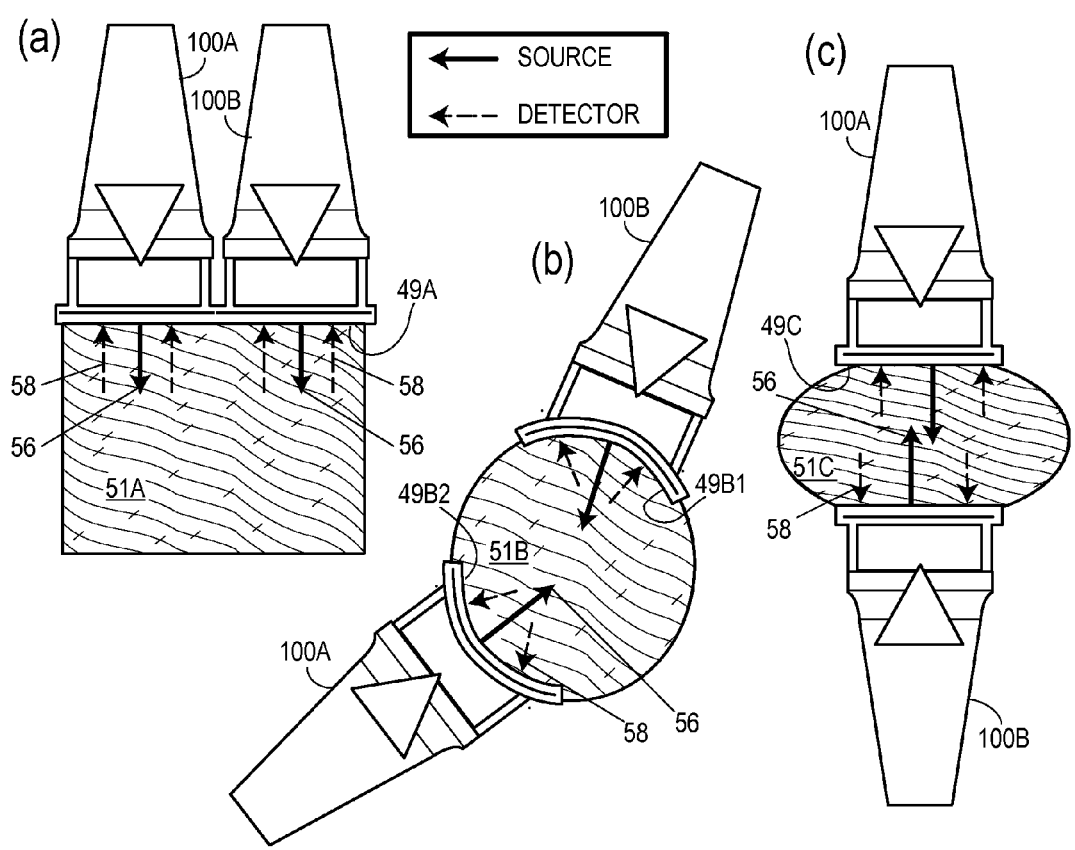
FIG. 8A illustrates a dual-probe configuration corresponding to the configuration depicted in FIG. 7.
FIG. 8B illustrates a dual-probe configuration corresponding to the configuration depicted in FIG. 6.
FIG. 8C illustrates a dual-probe configuration corresponding to the configuration depicted in FIG. 5.

With reference now to FIG. 8, a dual-probe configuration is depicted having source and detector configurations corresponding to those in FIGS. 5, 6, and 7. That is, in FIG. 8A, two probes 100A and 100B sit on a surface 49A of a tissue 51A and conduct sub-surface imaging as depicted in FIG. 7. Similarly, in FIG. 8B, the two probes 100A and 100B are disposed in an arrangement corresponding to FIG. 6, in which the probes, disposed on opposing surfaces 49B1 and 49B2, conduct circular imaging of the a tissue 51B. Likewise, in FIG. 8C, the two probes 100A and 100B are disposed on opposite sides of the surface 49C of a compressed tissue 51C, and conduct projection-shadow imaging as depicted in FIG. 5.

Each probe head 100A, 100B may also include an optical marker element 117 (as depicted in FIG. 10). In cooperation with a tracking system (described below), the optical marking element allows the position and orientation of the probe head 100A, 100B. The optical marking element 117 and the tracking and co-registration apparatus and processes cooperating with the optical marking element 117 to implement the system described herein are described below.

Probe Assembly and System

Figure 14:
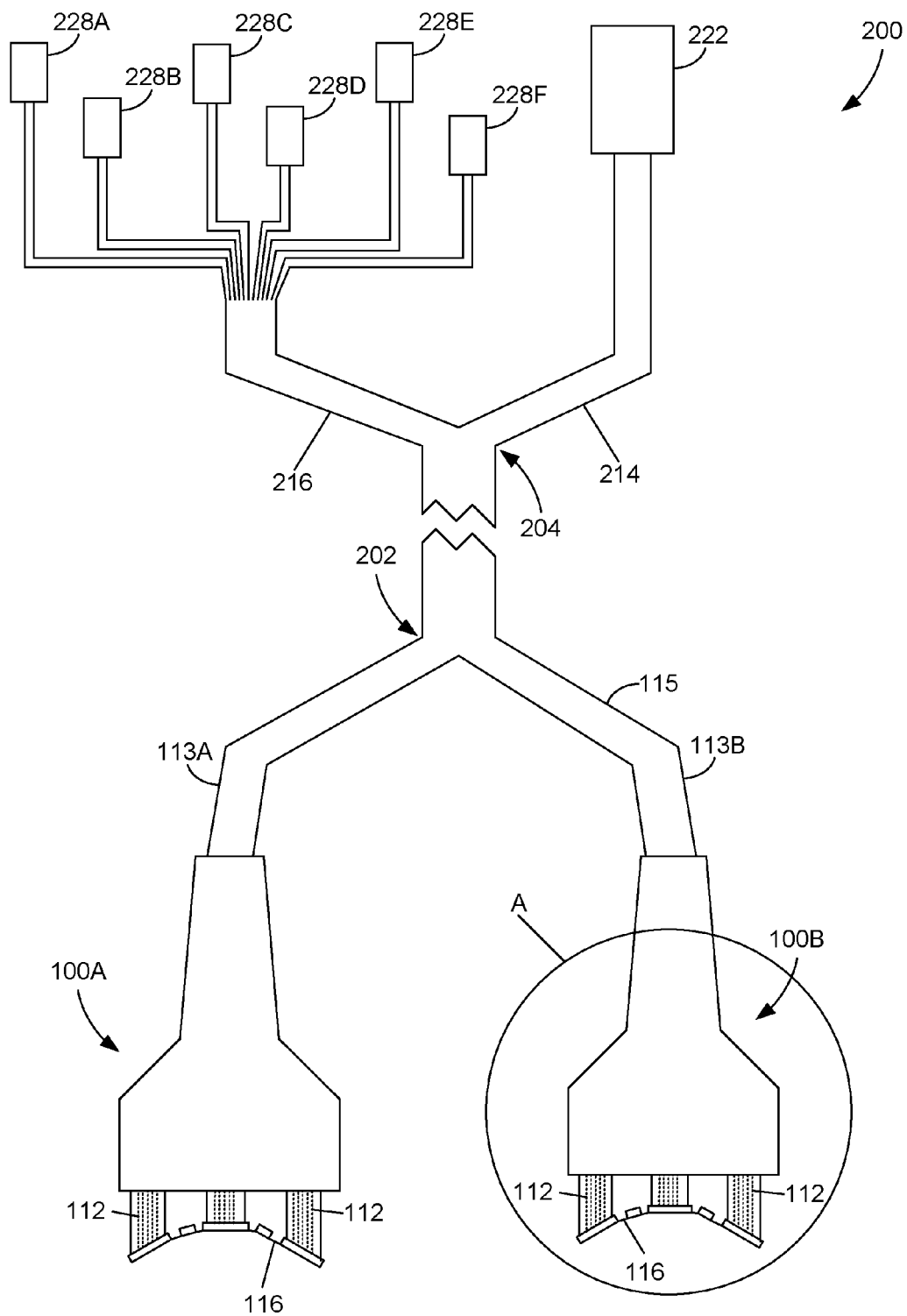
FIG. 14 depicts an exemplary probe assembly including dual probe heads.
Figure 17:
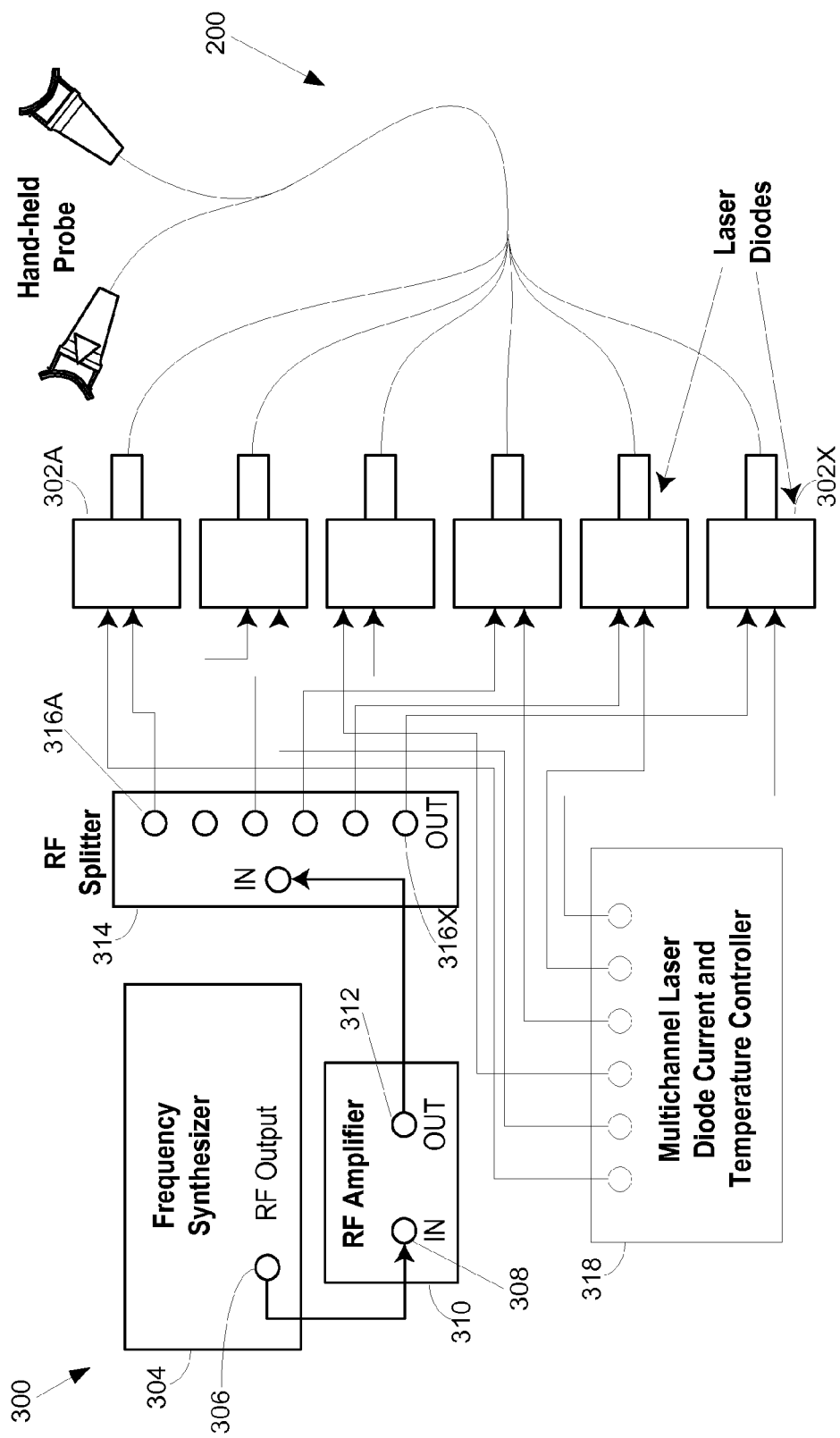
FIG. 17 depicts an exemplary illumination assembly.
Figure 19:
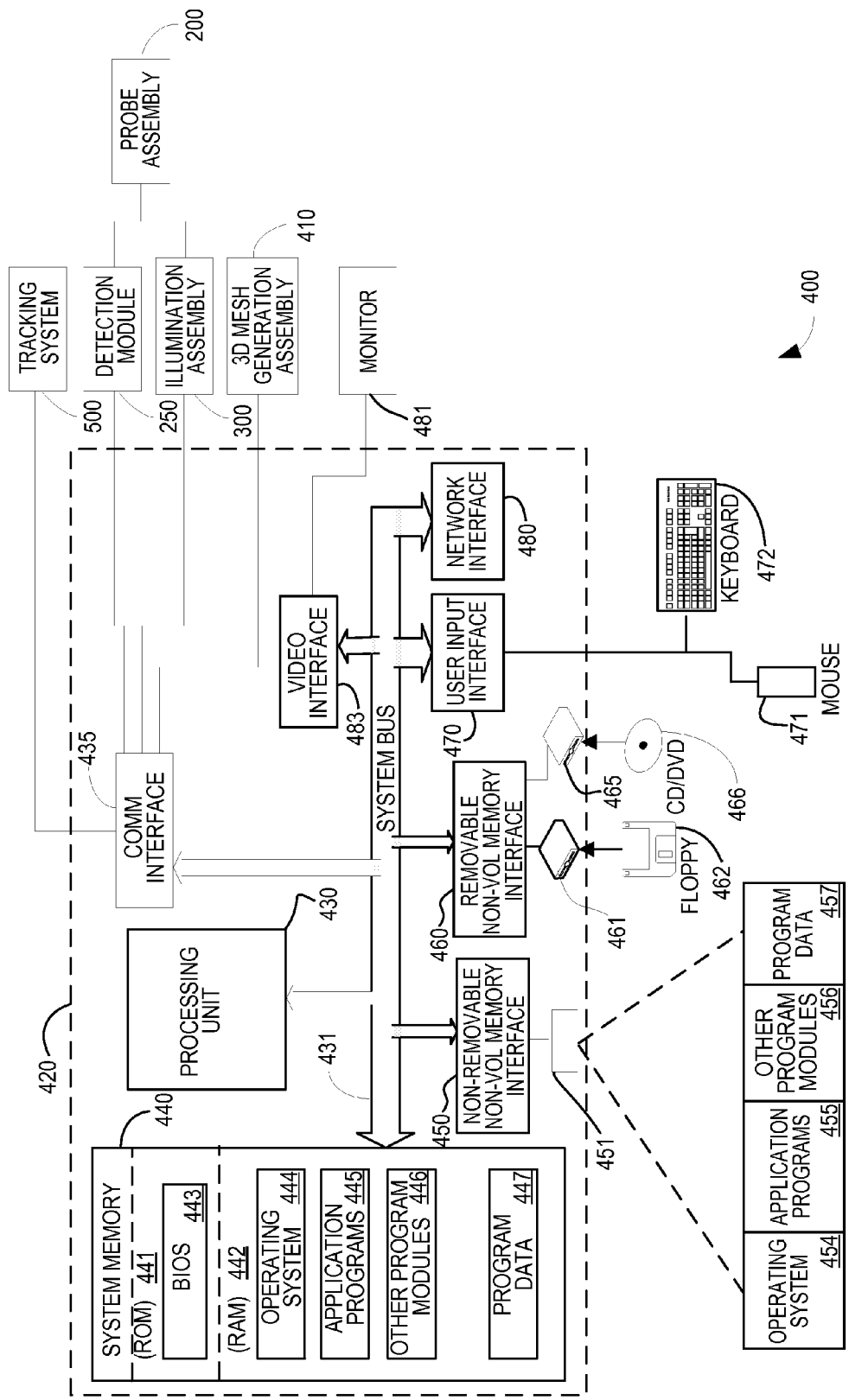
FIG. 19 is a block diagram of an imaging system in accordance with the presently described embodiments.

Regardless of the precise design of the probe head 100, the probe head 100 is part of a larger probe assembly, which, in turn, is part of a probe system 300 (described below with reference to FIGS. 17 and 19). FIG. 14 illustrates an exemplary probe assembly 200. The probe assembly 200 includes two probe heads 100A, 100B. Each of the probe heads 100A, 100B implements an optical point-illumination and detection scheme, wherein each of a plurality of optical fibers 112 terminates at the corresponding tissue contact surface 116 of the probe head 100A, 100B. As described above, some of the optical fibers 112 are illumination optical fibers and some of the optical fibers are detection optical fibers. In each of the probe heads 100A, 100B, the respective optical fibers 112 may be bundled into respective optical fiber cables 113A, 113B, which, in turn, may join to form a single optical fiber cable 115. The cable 115 (or the cables 113A, 113B) may continue from a probe end 202 to a connector end 204. In some embodiments, the detection optical fibers may be bundled into respective optical fiber cables 113A, 113B, while each of the source optical fibers may pass exit the probe heads 100A, 100B independently and connect separately to a respective optical source (not shown).

Figure 15:
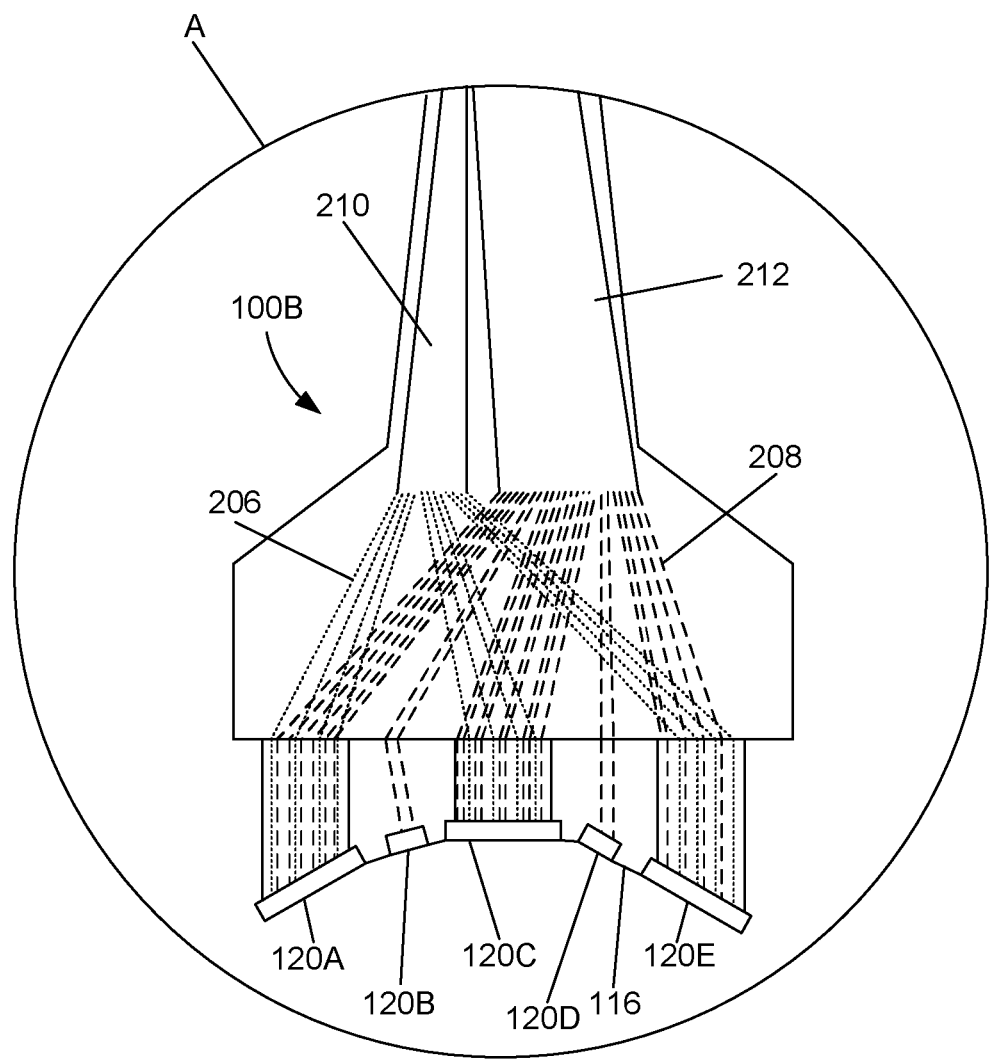
FIG. 15 illustrates the fiber optic connections to a probe face in an exemplary embodiment of the probe head.

FIG. 15 illustrates in greater detail the inset "A" indicated in FIG. 14 and, in particular, depicts a plurality of illumination optical fibers (indicated by the dotted lines 206) and a plurality of detection optical fibers (indicated by the dashed lines 208). In the embodiment depicted in FIGS. 14 and 15, the probe head 100B includes five termination structures 120A-E at which the optical fibers 206, 208 terminate. While FIG. 15 depicts four illumination optical fibers terminating at each of the termination structures 120A, 120C, and 120E, and no illumination optical fibers terminating at each of the termination structures 120B and 120D (as indicated by the lines 206), other embodiments of the probe head 100B may incorporate different numbers and/or different configurations of illumination optical fibers, including incorporating fewer or more illumination optical fibers to one or more of the structures 120A-E. For example, referring again to FIGS. 11 and 12, a probe head incorporating the probe face 102 depicted in FIGS. 11 and 12 has: four illumination optical fibers terminating at the apertures 124 corresponding to the illumination apertures 130 in termination structure 120A; two illumination optical fibers terminating at the apertures 124 corresponding to the illumination apertures 130 in termination structure 120B; four illumination optical fibers terminating at the apertures 124 corresponding to the illumination apertures 130 in termination structure 120C; no illumination optical fibers terminating at the apertures 124 in termination structure 120D; and five illumination optical fibers terminating at the apertures 124 corresponding to the illumination apertures 130 in termination structure 120E.

Likewise, while FIG. 15 depicts six, nine, and five detection optical fibers terminating, respectively, at each of the termination structures 120A, 120C, and 120E, and two detection optical fibers terminating at each of the termination structures 120B and 120D (as indicated by the lines 208), other embodiments of the probe head 100B may incorporate different numbers and/or different configurations of detection optical fibers, including incorporating fewer or more detection optical fibers to one or more of the structures 120A-E. For example, referring again to FIGS. 11 and 12, a probe head incorporating the probe face 102 depicted in FIGS. 11 and 12 would have: 38 detection optical fibers terminating at the apertures 124 corresponding to the detection apertures 132 in termination structure 120A; five detection optical fibers terminating at the apertures 124 corresponding to the detection apertures 132 in termination structure 120B; 38 detection optical fibers terminating at the apertures 124 corresponding to the detection apertures 132 in termination structure 120C; seven detection optical fibers terminating at the apertures 124 in termination structure 120D; and 37 detection optical fibers terminating at the apertures 124 corresponding to the detection apertures 132 in termination structure 120E.

In any event, referring once again to FIG. 15, the illumination optical fibers (indicated by the lines 206) may be grouped into a bundle 210 and the detection optical fibers (indicated by the lines 208) may be grouped into a bundle 212. The bundles 210 and 212 of illumination and detection optical fibers are preferably joined together to form the optical fiber cable 113B depicted in FIG. 14. Alternatively, as described above, each of the illumination optical fibers may remain unbundled between the contact surface 116 and the illumination source(s) or between the probe head 100A, 100B and the illumination source(s).

Referring again to FIG. 14, tt the connector end 204 of the optical fiber cable 115, the various optical fibers 112 may once again be grouped and separated from one another. For example, the detection optical fibers may be separated into a detection optical fiber sub-cable 214 and the illumination optical fibers into a corresponding illumination optical fiber sub-cable 216. Thus, for the probe assembly 200 including two probe heads 100A, 100B, the detection optical fiber sub-cable 214 would include two sets of optical fibers 112 (one set each from probe heads 100A and 100B) and the illumination optical fiber sub-cable 216 would include all of the illumination optical fibers.

The optical fibers 112 in the detection optical fiber sub-cable 214 may terminate at a coupling device 222 adapted to couple to a detection system which, in some embodiments, includes a CCD. Each of the optical fibers 112 in the detection optical fiber sub-cable 214 may be associated with a particular location on the contact surface 116 of a particular one of the probe heads 100A, 100B. The optical fibers 112 need not be arranged such that each optical fiber 112 maintains the same relationship with respect to the others as it does at the probe face 102. Instead, the detection system may be programmed to associate certain pixels with each of the optical fibers 112 and to reconstruct an image based on the known termination point of each optical fiber 112 on at the probe face 102. In some embodiments, the optical fibers 112 originating at the probe faces 102 of the respective probe heads 100A, 100B may terminate at respective coupling devices (not shown) for coupling to respective detection systems (i.e., the optical fibers 112 of each probe head 100A, 100B may be coupled to a respective detection system).

If bundled, the optical fibers 112 in the illumination optical fiber sub-cable 216 may terminate, respectively, at coupling devices 228A-F (for an embodiment having six illumination optical fibers—three per probe head), each of which may be adapted to couple, for example via an SMA or an FC connector, as generally known) to an illumination system as described below. In some embodiments, the optical fibers 112 in the illumination optical fiber sub-cable 216 may couple directly to a single coupling device (e.g., the device 230 depicted in FIG. 16) configured to connect all of the illumination optical fibers 112 for both probe heads 100A, 100B to the illumination source. In other embodiments, each of the illumination optical fibers 112 in the illumination optical fiber sub-cable 216 (or remaining unbundled from the probe heads 100A, 100B) may terminate at a respective optical source (e.g., a laser diode), as depicted in FIG. 17.

Figure 16:
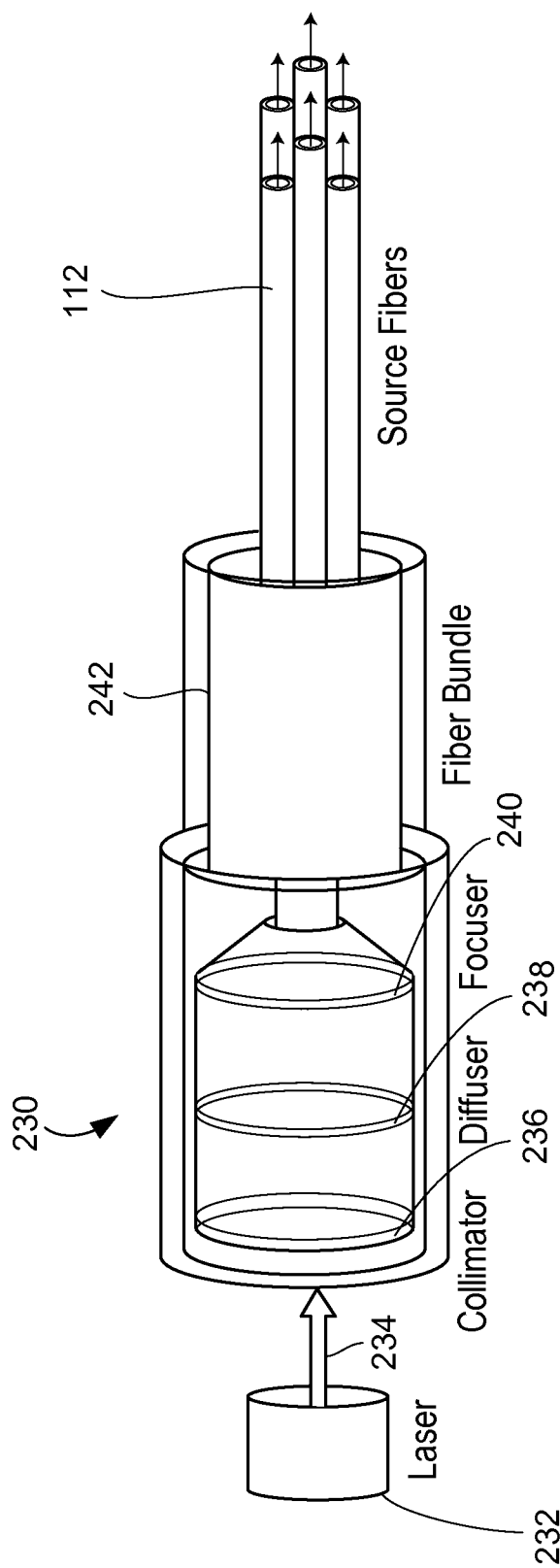
FIG. 16 depicts an exemplary fiber optic connector device for connecting the probe assembly to an embodiment of an illumination assembly.

FIG. 16 illustrates an embodiment of a coupling device 230 for coupling all or at least multiple illumination optical fibers to a single illumination source. In the illustrated embodiment, a laser or laser diode 232 may be used as a light source. Light 234 emanating from the laser 232 light may be collimated by a collimator 236. In some embodiments, the collimator 236 may be optional. Collimated light output from the collimator 236 may then be channeled to a diffuser 238 for evenly spreading the collimated light over a particular surface area. In this embodiment, the diffuser 238 spreads the collimated light over the input surface of a focuser 240. The focuser 240 may be selected to concentrate collimated light onto first ends of a bundle 242 of optical fibers 112. In some embodiments the diffuser 238 and/or the focuser 240 may be optional. Specifically, in some embodiments, the light 234 may be focused onto a first end of a particular optical fiber 112 which may be terminated at a second end at one of the apertures 120 of one of the termination structures 120A-E and, in particular, at one of the apertures 124 corresponding to an illumination aperture 130.

In other embodiments, each illumination optical fiber may be coupled to a respective illumination source. Turning now to FIG. 17, the probe assembly 200 may be connected by the coupling device 230 to an illumination assembly 300 for providing an optical signal, via the probe assembly 200, to the tissue to be imaged. In the depicted embodiment of the illumination assembly 300, a plurality of N (where N is a number of elements in the plurality of elements) laser diodes 302A-X (where 302X designates the Nth laser diode) is provided. Each of the laser diodes 302A-X is coupled to one of the illumination optical fibers (see lines 206 in FIG. 15). In an embodiment corresponding to a frequency domain embodiment, each of the N laser diodes is controlled by a simultaneous source. Specifically, a frequency synthesizer 304 generates a radio frequency (RF) signal and outputs the signal from an RF output 306. The RF signal is input into an input 308 of an RF amplifier 310, which amplifies the RF signal and outputs the RF signal from an RF output 312. The RF signal from the output 312 is input into an RF splitter 314 to generate, and output from outputs 316A-X, N simultaneous RF signals to drive the N laser diodes 302A-X. In an embodiment corresponding to a continuous wave embodiment, a multichannel laser diode current and temperature controller 318 drives the laser diodes 302A-X. An external optical switch (not shown) may, in some embodiments, be included to control the number of simultaneous sources used during an imaging study. The output of each of the laser diodes (i.e., a laser optical signal) is coupled to a respective illumination optical fiber in the probe assembly 200.

Figure 18:
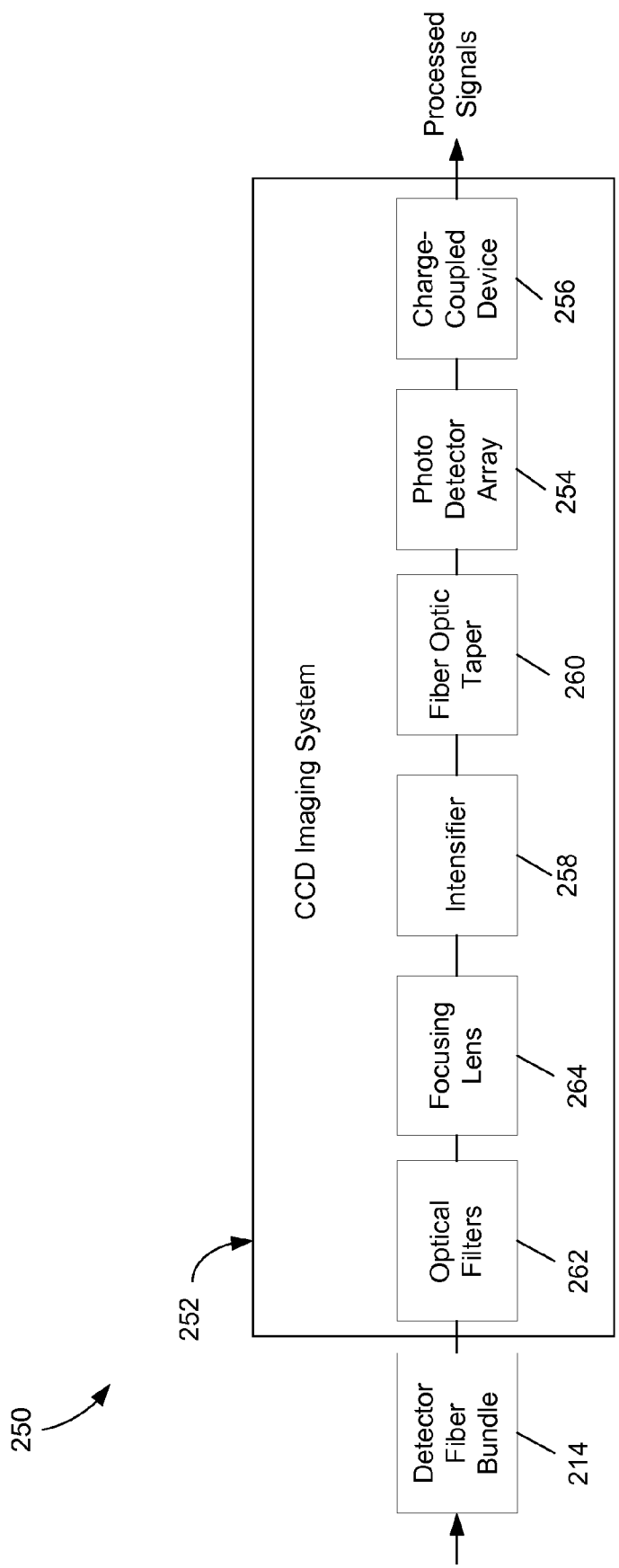
FIG. 18 is a block diagram of an exemplary detection system using a charge-coupled device.

The probe assembly 200 may be used with a fluorescence-enhanced or non-fluorescence diffuse optical imaging process and may also be coupled, for example by the coupling device 222, to a frequency-domain or CW intensified CCD (ICCD) detection module. FIG. 18 depicts a block diagram of an embodiment of a detection module 250. The detection module 250 may be any CCD sensor or other detector such as photo-multiplier tubes (PMT), avalanche photo diodes (APD), or silicon photo diodes. These detectors may be used individually or in a plurality to detect light. If a plurality of the detectors is used, the detectors may be activated sequentially or simultaneously. The detection module 250 may be configured to operate as a time-dependent (FD or TD) and/or as a time-independent (CW) detection system. The detector system may operate in conjunction with a light source using TDPM, FDPM, or CW approaches. The light source is a laser source, or any other light source capable of providing the appropriate light characteristics. Light from the light source(s) 232 (or 302A-X) may be projected on to a target tissue surface via the illumination optical fibers of the probe assembly 200. The probe assembly 200 may collect optical signals (including NIR, visible, or any other optical signals) from different points on a tissue boundary surface (e.g., on the surface of a breast or other tissue being imaged) via the detection optical fibers of the probe assembly 200, where the signals may be simultaneously processed using the gain-modulated ICCD detector for an enhanced data acquisition rate. A homodyne technique may be implemented in the system where the laser source and the detector are modified at the same frequency (e.g., in the MHz range). Data acquisition rates of the homodyned frequency domain measurements may depend on the number of phase delays between the frequency synthesizers modulating the image intensifier and the laser diode modulation, the number of repeated images averaged to acquire phase-sensitive images, the integration or exposure time of the CCD to obtain each image, and the degree of data binning downwards from a pixelated image in the CCD. The combination of the above variables may be assessed to determine the data acquisition scheme with minimal measurement time, reduced measurement errors, and maximum resolution of the optical images. In some embodiments, the frequency-domain measurements detected by the detection module 250 may be based on the heterodyne technique, where the modulation frequencies at the laser source and the detector are not the same.

Referring still to FIG. 18, the detection module 250 may be a CCD imaging system 252, and may be built using a custom 16-bit CCD camera that includes a photo-detector array 254 for transforming light signals into corresponding electrical signals and a charged-coupled device (CCD) 256 for processing the electrical signals. The photo-detector array 254 and charge-coupled device 256 may enable higher frame transfer capability to enhance image acquisition and storage rates. The photo-detector array 254 may be fiber optically coupled to a near infrared (NIR) sensitive image intensifier 258 via a fiber optic taper 260. The image intensifier 258 may be included in the CCD system 252 to amplify weak light signals at MHz range. The NIR-sensitive image intensifier 258 (e.g., a conventional filmed or filmless tube) may generally work to reduce image retention effect and to increase sensitivity to weak NIR (both fluorescence and non-fluorescence) signals. A custom-built fiber optic taper 260 may be used to interface the output of the intensifier 258 to the photo-detector array 254 to improve the coupling efficiency of image intensifier 258. In the absence of an image intensifier, it is not possible to implement a frequency-domain analysis because the image intensifier allows the signal from the CCD camera to be modulated.

The detection optical fibers in the bundle 214 may be coupled to optical filters 262 and a focusing lens 264, where the focusing lens 264 outputs light signals to the intensifier 258. Different optical filter combinations (e.g., interference, long pass, band pass, holographic, etc.) may be used to isolate and extract light signals at particular wavelengths of interest and to remove signals at other wavelengths. In the case of fluorescence-enhanced optical imaging, use of an appropriate optical filter combination may help minimize the excitation leakage that prevents the detection of weak and low intensity fluorescence signals arising from deep and/or small targets.

The detection module 250 and the illumination assembly 300 may, in addition to being optically coupled to the probe assembly 200, be communicatively coupled to a computing device. FIG. 19 is a block diagram depicting an embodiment 400 of a hand-held optical probe based imaging system with 3D tracking facilities. FIG. 30 depicts a logical view of a computing device in the form of a computer 420 that may be used in such a system. For the sake of illustration, the computer 420 is used to illustrate the principles of the instant disclosure. However, such principles apply equally to other electronic devices having sufficient computing power, including, but not limited to, cellular telephones, smart phones, tablet computers, netbook computers, workstations, and personal digital assistants, to name a few. Components of the computer 420 may include, but are not limited to a processing unit 430, a system memory 440, and a system bus 431 that couples various system components including the system memory 440 to the processing unit 430. The system bus 431 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, front side bus, and Hypertransport™ bus, a variable width bus using a packet data protocol.

Computer 420 may include one or more serial, parallel, or other communication interfaces 435, such as Universal Serial Bus (USB) interfaces, IEEE-1394 (FireWire) interfaces, RS-232 interfaces, RS-423 interfaces, RS-485 interfaces, IEEE-488 (HPIB or GPIB) interfaces, etc. The computer 420 may communicate through the communications interface 435 with, for example, the detection module 250, the illumination assembly 300, a 3D mesh generation assembly 410, and/or a tracking system 500 (as described in detail below).

Computer 420 typically includes a variety of computer readable media. Computer readable media can be any available media that can be accessed by computer 420 and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 420.

The system memory 440 includes computer storage media in the form of volatile and/or nonvolatile memory such as read only memory (ROM) 441 and random access memory (RAM) 442. A basic input/output system 443 (BIOS), containing the basic routines that help to transfer information between elements within computer 420, such as during start-up, is typically stored in ROM 441. RAM 442 typically contains data and/or program modules that are immediately accessible to and/or presently being operated on by processing unit 430. By way of example, and not limitation, FIG. 19 illustrates operating system 444, application programs 445 (such as one or more modules embodying part or all of the methods described herein), other program modules 446 (such as one or more modules embodying part or all of the methods described herein), and program data 447. By way of example, the application programs 445 and the other program modules 446 may implement control of and/or cause the processor 430 to process data received from the detection module 250, the illumination assembly 300, and the tracking system 500. For instance, with respect to the illumination system 300, the programs 445 and modules 446 may implement control of the frequency, output power, etc. of the frequency synthesizer 304, may implement control of the amplification factor of the RF amplifier 310, may implement control of the laser diode controller 318, may implement control of the external optical switch, etc. As another example, with respect to the detection module 300, the programs 445 and modules 446 may implement control of the CCD imaging system 252 and/or may process data (e.g., image information received from the probe assembly 200) received from the detection module 250. As yet another example, with respect to the tracking system 500, the programs 445 and modules 446 may process data received from the tracking system 500 to determine current position and/or orientation data of the probes 100A, 100B and/or of the subject of study, may process data received from the tracking system 500 and the detection module 250 to co-register image data and 3D mesh data, or may implement control of one or more aspects of the tracking system 500. As still another example, with respect to the 3D mesh generation assembly 410, the programs 445 and modules 446 may process data received from a 3D optical scanner, may implement a control function of the 3D optical scanner, may implement control of a positioning device associated with the 3D optical scanner, etc.

The computer 420 may also include other removable/non-removable, volatile/nonvolatile computer storage media. By way of example only, FIG. 19 illustrates a hard disk drive 451 that reads from or writes to non-removable, nonvolatile magnetic media, a magnetic disk drive 461 that reads from or writes to a removable, nonvolatile magnetic disk 462, and an optical disk drive 465 that reads from or writes to a removable, nonvolatile optical disk 466 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 451 is typically connected to the system bus 431 through a non-removable memory interface such as interface 450, and magnetic disk drive 461 and optical disk drive 465 are typically connected to the system bus 431 by a removable memory interface, such as interface 460.

The drives and their associated computer storage media discussed above and illustrated in FIG. 19, provide storage of computer readable instructions, data structures, program modules, and other data for the computer 420. In FIG. 19, for example, hard disk drive 451 is illustrated as storing operating system 454, application programs 455, other program modules 456, and program data 457. Note that these components can either be the same as or different from operating system 444, application programs 445, other program modules 446, and program data 447. Operating system 454, application programs 455, other program modules 456, and program data 457 are given different numbers here to illustrate that, at a minimum, they are different copies. A user may enter commands and information into the computer 420 through input devices such as a keyboard 472 and pointing device 471, commonly referred to as a mouse, trackball, or touch pad. Other input devices (not shown) may include a microphone, joystick, game pad, satellite dish, scanner, digital camera, or the like. These and other input devices are often connected to the processing unit 430 through a user input interface 470 that is coupled to the system bus 431, but may be connected by other interface and bus structures, such as a parallel port, game port or a universal serial bus (USB). A monitor 481 or other type of display device is also connected to the system bus 431 via an interface, such as a video interface 483.

The computer 420 may operate in a networked environment using logical connections to one or more remote computers (not depicted) over a network interface 480, such as broadband Ethernet connection or other known network. The computer 420 may communicate via the network interface 480 with one or more other computers executing one or more software modules embodying a portion of the methods described herein, for example to split the processing requirements for real-time data manipulation among multiple computers.

3D Mesh Generation

In both modeling and image reconstruction, a region of interest(s) (e.g. 2-D or 3D tissue object or phantom) may be divided into discrete 2-D or 3D elements. Due to the limited surface area of the probe heads 100A, 100B sensor data are captured only for a portion of the region of interest at one time. To obtain three-dimensional visualization of a large region of interest, each time the probes 100A, 100B are moved, the positions and orientations of each may be monitored and co-registered or mapped. As used herein, co-registration refers to the mapping of sensor data for a particular region onto to a map (e.g., a discretized mesh) of the entire region of interest(s). Generally, registration provides 3D location and orientation data for the sensor data. For example sensor data captured during a first period at first positions of the probes 100A, 100B may be mapped to corresponding first positions of a map of the entire region of interest. To implement self-registration or co-registration of the sensor data for the region of interest, a tracking system may be used to monitor the location of the probes 100A, 100B. An exemplary tracking system is described in detail below.

Figure 20:
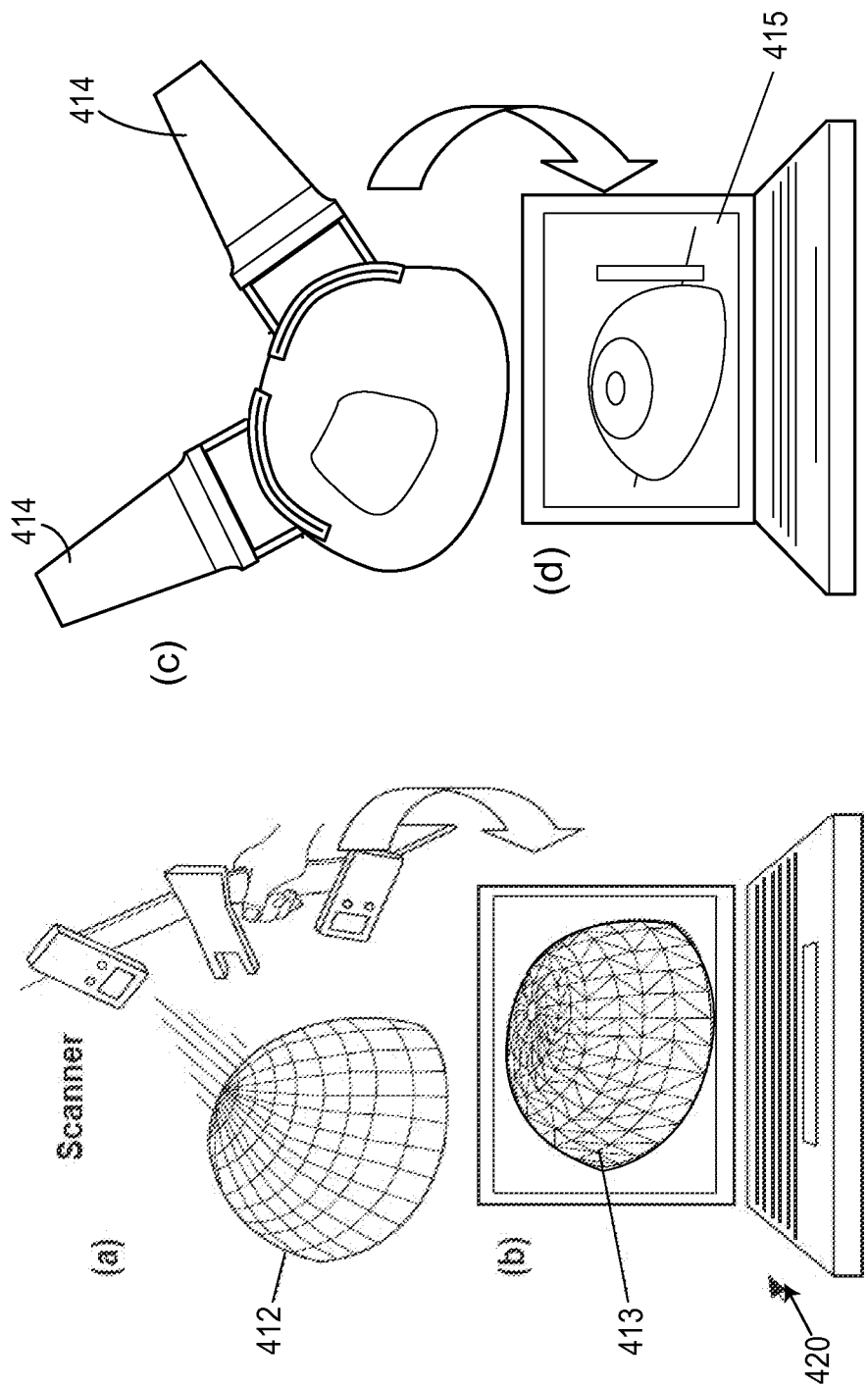
FIG. 20 depicts a scanning system for generating a 3D mesh.
Figure 21:
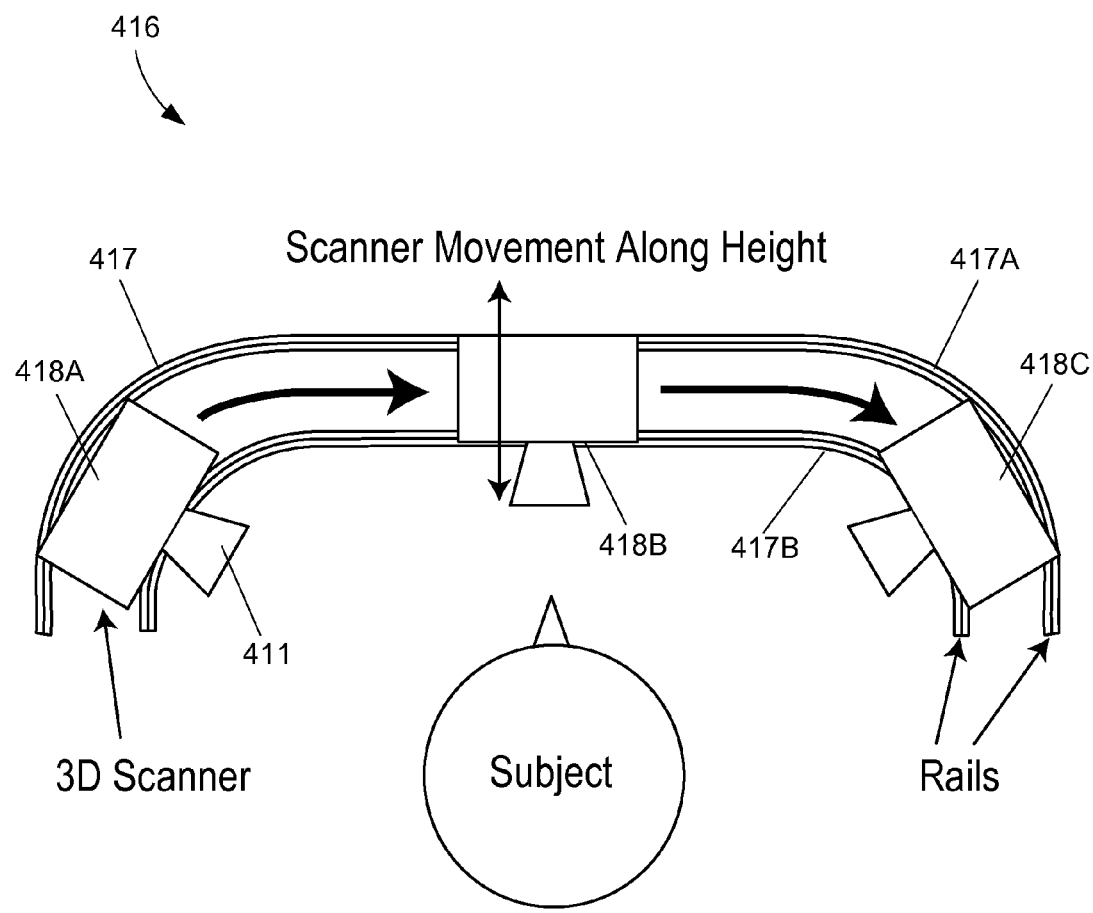
FIG. 21 illustrates an automatic component of a scanning system for generating a 3D mesh.

FIGS. 20 and 21 illustrate possible embodiments related to the obtaining 3D tomography-relevant sensor data using a self-registering (automatic registering) hand-held probe based imaging system. FIGS. 20 and 21 relate particularly to a 3D mesh generation assembly 410. A three-dimensional optical scanner 411, as known in the art, may be used on a target object 412 (without any contact) to provide a 3D surface image of the target object 412, which can be volume rendered and discretized using appropriate meshing software, as known in the art. In some embodiments, the volume rendering process may involve generating a three-dimensional (3D) mesh 413 of point coordinates or point locations sub-surface to the rendered 3D surface image (e.g., for the entire volume of the target object 412). This 3D mesh may be known as a "phantom mesh" because it serves as a structure over which the target data may be mapped or overlaid or with which the target data may be co-registered (as described below).

The 3D mesh 413 of the target object 412 may be displayed on the monitor 481 of the computing device 420. A probe or probes 414 for collecting sensor data, such as the optical imaging probes 100A, 100B described above, may then be traced over the target object 412 to obtain sensor data. The 3D location map of the probe 414 with respect to the 3D mesh 413 of the target object 412 may be obtained using the tracking system 500 (described below). In some embodiments, the computing system 420 may be programmed (e.g., using appropriate software and algorithms, such as those described herein) to receive sensor data from the probes 414 for a time period, receive probe position data and/or orientation data from the tracking system 500 for the time period, and co-register the received data with appropriate mesh locations on the 3D mesh 413 based on the position data. In this manner, the location data and the sensor data collected over a region may be mapped to the corresponding region on the 3D mesh 413 surface to generate co-registered map sensor data 415. The computing device 420 may co-register or map sensor data with respect to a reference position arbitrarily (or specifically) chosen on the 3D mesh 413 of the target object 412. The computing system 420 may be further programmed to process the sensor data before and/or after mapping/co-registering to the mesh 413 depending on a particular application of the sensor data. This co-registered sensor data may then be transformed into a 2D and/or 3D tomogram using appropriate algorithms. These tomograms may include reconstructions of subsurface structures within the target object. The subsurface structures may include abnormal tissue such as tumors.

In some embodiments, the 3D mesh generation assembly 410 may include an automatic scanning mechanism 416, such as that illustrated in FIG. 21. The automatic scanning mechanism 416 includes an optical scanner such as the optical scanner 411 movably mounted on a positioning device 417. The positioning device 417 may be one or more rails (such as rails 417A, 417B depicted in FIG. 21) upon which the optical scanner 411 may be mounted. A motor (not shown) on the optical scanner 411 or integrated with the rail(s) 417 may position and/or move the optical scanner 411 from an initial position 418A, around the subject to be imaged to a final position 418C, passing through intermediate positions such as a position 418B. The optical scanner 411 may scan the subject continuously or, at least, a plurality of times, as it moves from the initial position 418A to the final position 418C. The positioning device 417 is not limited to the rails depicted in FIG. 21, but instead may be a robotic arm, one or more cables, etc. In some embodiments, the movement of the optical scanner 411 via the positioning device 417 is controlled by the computing device 420. The positioning device 417 may scan the subject at each of a plurality of heights. For example, in one embodiment, the scanner 411 scans the subject by moving along the rails 417 at a first height, and then the height of the rails 417 (and the scanner 411 mounted thereon) is adjusted and the process repeated. This process may be iterated multiple times adjusting the height of the rails 417 each time by, for example, 0.5 inches, 1 inch, 3 inches, etc.

Probe Tracking

Some single-probe optical imaging systems have employed acoustic trackers, which may be commercially available, to track the position of the probe head while acquiring imaging data. As described in U.S. patent application Ser. No. 12/625,476, entitled "Hand-Held Optical Probe Based Imaging System with 3D Tracking Facilities," and incorporated herein in its entirety by reference, acoustic trackers that determine probe location via sound may be appropriate for an optical imaging system because acoustic receivers may be small, lightweight, and inexpensive. In some embodiments, two or more acoustic trackers could be used with the dual probe head design described herein.

Figure 22:
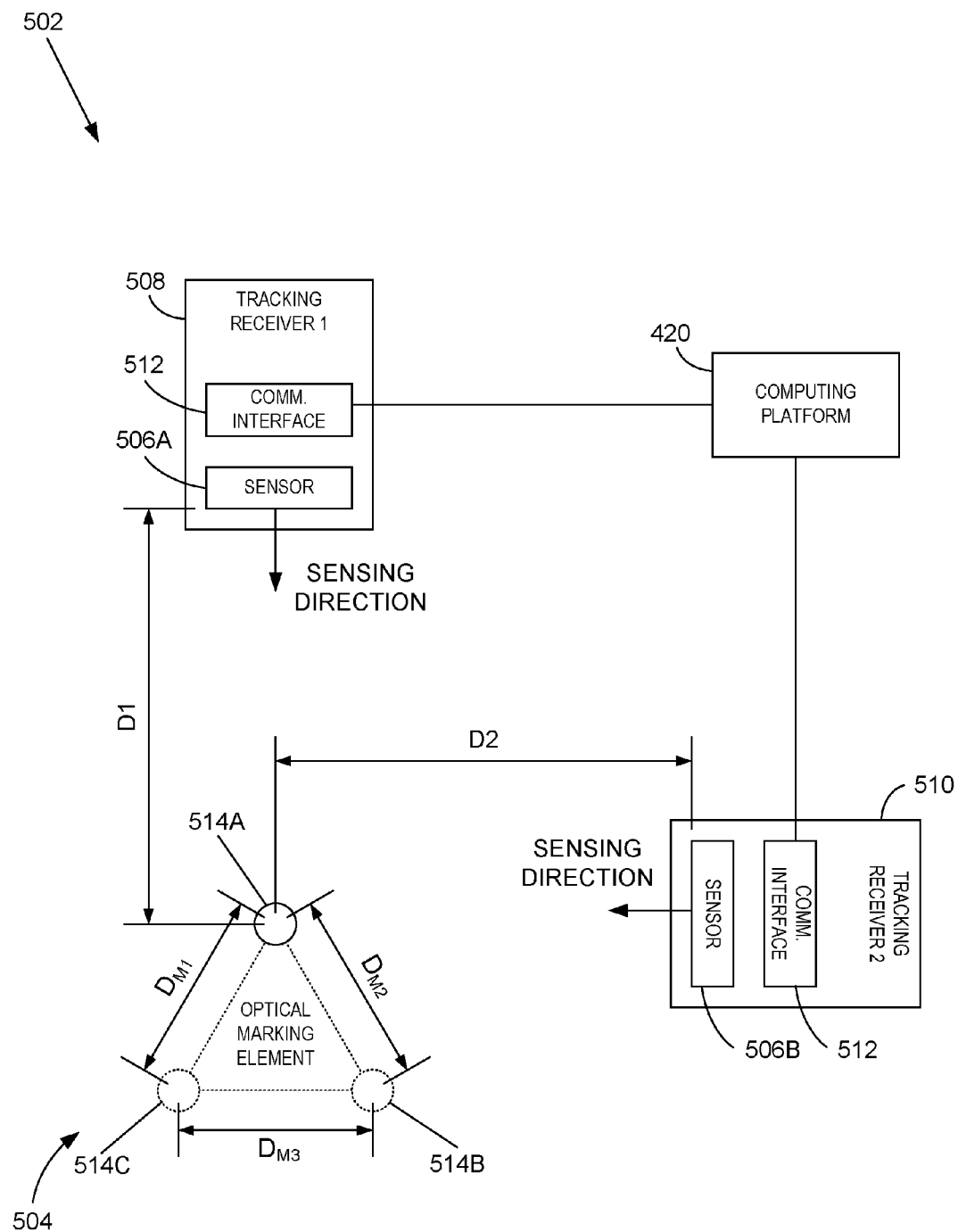
FIG. 22 depicts a block diagram of an optical tracking system for tracking a probe head in the presently described imaging system.

However, in some embodiments, the tracking system 500 (see FIG. 19) may employ an optical tracking method and devices instead of an acoustic tracking method and devices. FIG. 22 depicts, in block format, the basic elements of an optical tracking system 502. The optical tracking system 502 includes two or more optical marking elements 504 (one for each probe head; though only one optical marking element 504 is depicted in FIG. 22) and two or more sensors 506A, 506B. In some embodiments, the sensors 506A, 506B are disposed in separate, and potentially identical, tracking receivers 508, 510. Though the sensors 506A, 506B may be disposed in a single tracking receiver, the sensors 506A, 506B may nevertheless be separated by some distance and/or angle. For example, FIG. 22 depicts the two tracking receivers 508, 510 offset by a distance D1 in a first direction and by a distance D2 in a second direction with the sensors 506A, 506B having orientations 90 degrees offset from one another. The tracking receivers 508, 510 may collectively be tilted to achieve an optimal position for maintaining the optical marking elements 504 in the field of view of the sensors 506A, 506B. The tracking receivers 508, 510 each have a communication interface 512 employed to communicate with the computing platform 420 and/or with the other tracking receiver(s) 508, 510.

The sensors 506A, 506B may each be an image sensor such as a CCD image sensor and, in particular, may be an infrared CCD image sensor sensitive to a particular wavelength. One or more filters may optionally be included in the optical path of the sensors 506A, 506B to increase the selectivity of the CCD image sensor to the particular wavelength desired.

Each of the optical marking elements 504 includes two or more marker LEDs, which may be infrared LEDs and, specifically, may be LEDs of a particular wavelength. FIG. 22, for example, depicts the optical marking element 504 including three marker LEDs 514A, 514B, 514C. The marker LEDs 514A, 514B, 514C have a known geometric relationship to one another. Given the known geometric relationship between the marker LEDs and the known geometric relationship between the sensors 506A, 506B, the positions of the LEDs may be determined by triangulation and, therefore, the positions and orientations of the probe heads to which the LEDs are attached may be determined.

While two marker LEDs 514 per optical marking element 504 may be sufficient to track position (e.g., x, y, z) and orientation (e.g., pitch, roll, yaw) of in 3D space with one sensor (e.g., with the sensor 506A), additional degrees of freedom may be achieved by employing an optical marking element 504 implemented with three marker LEDs 514. This may require the use of dual sensors 506A, 506B for tracking each optical marking element 504 and, thus, may require four sensors to track optical marking elements 504 for two probe heads (i.e., 6 marker LEDs; three for each optical marking element 504).

Figure 23:
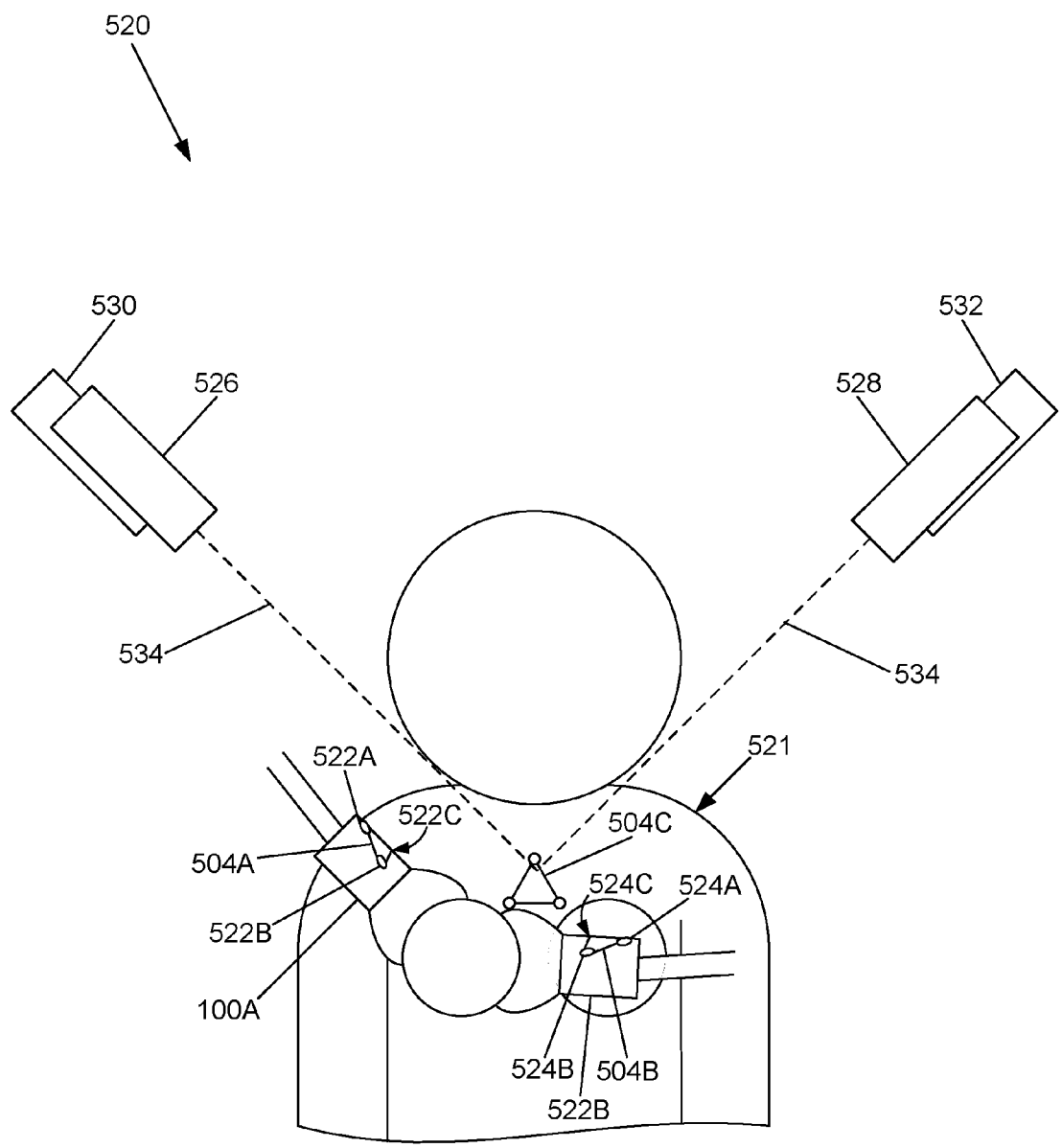
FIG. 23 illustrates the use of the tracking system of FIG. 22.

In an embodiment 520 depicted in FIG. 23, for example, each of the two probe heads 100A, 100B has an associated optical marking element 504A, 504B positioned thereon. Each of the optical marking elements 504A, 504B includes three marker LEDs. In some embodiments, an additional optical marking element 504C may be positioned on the target (e.g., on a patient 521). The marking element 504C may be used to track movement of the subject and to update a relative position of the 3D mesh with respect to the probe heads 100A, 100B. In any event, in the embodiment 520, the optical marking element 504A includes three marker LEDs 522A, 522B, 522C and the optical marking element 504B includes three marker LEDs 524A, 524B, 524C. In the embodiment 520, two tracking receivers 526, 528 are employed to track the optical marking element 504A and two tracking receivers 530, 532 are employed to track the optical marking element 504B. The tracking receivers 526 and 528 are offset from one another by 90 degrees (indicated by the lines 534) and the tracking receivers 530 and 532 are also offset from one another by 90 degrees.

Each of the tracking receivers 526-532 may have a filter (not shown) in the optical path between the corresponding sensors and the marker LEDs. For example, in an embodiment the first pair of tracking receivers 526, 528 includes a first optical filter configured to pass light of a wavelength A, which wavelength A corresponds to the wavelength of the marker LEDs 522A, 522B, 522C, so that the tracking receivers 526, 528 can track the marker LEDS 522A, 522B, 522C on the optical marking element 504A. Correspondingly, the second pair of tracking receivers 530, 532 includes a second optical filter configured to pass light of a wavelength B, which wavelength B corresponds to the wavelength of the marker LEDs 524A, 524B, 524C, so that the tracking receivers 530, 532 can track the marker LEDS 524A, 524B, 524C on the optical marking element 504B.

The 90-degree offset between the tracking receivers in each pair of tracking receivers provides a convenient way to calibrate a 3D coordinate space of each tracking receiver with a 3D coordinate space of the other tracking receiver. Specifically, each tracking receiver will have an independent two-dimensional (2D) coordinate system (X,Y). The planes defined by the independent 2D coordinate systems will be orthogonal to one another (because the tracking receivers are orthogonal to one another). Thus, by aligning a point (such as the origin) of each of the 2D coordinate systems with the same point (e.g., the origin) of the other 2D coordinate system, a finite 3D coordinate space can be defined.

Figure 24:
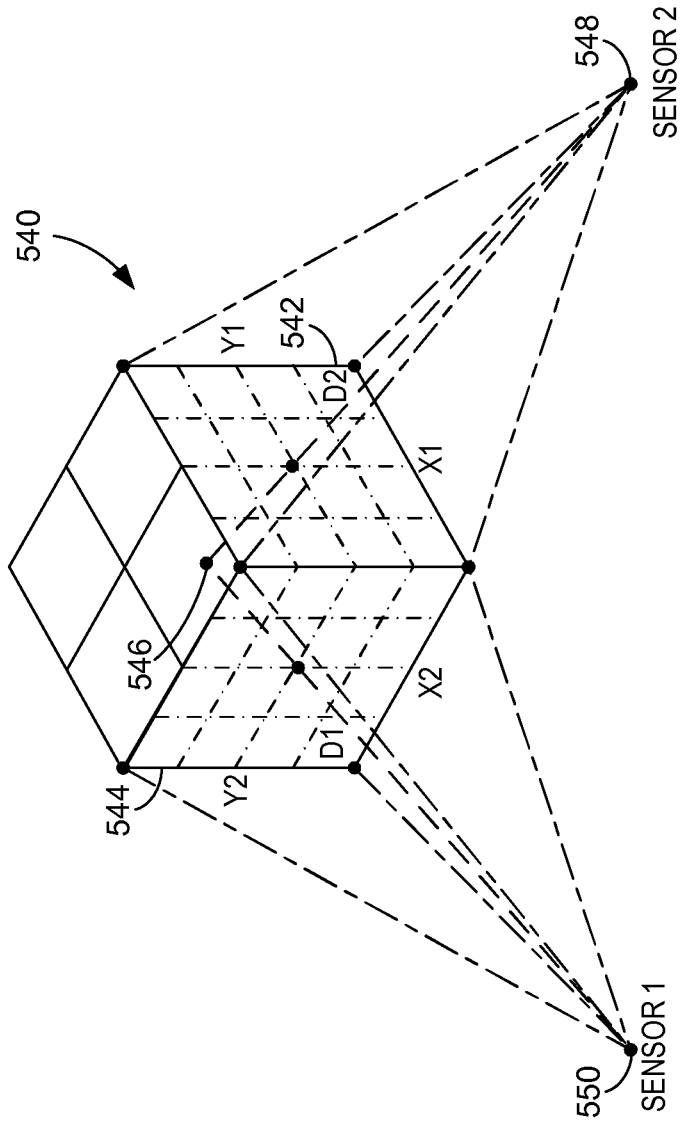
FIG. 24 illustrates a 3D coordinate space generated by the tracking system of FIG. 22 using two tracking receivers.
Figure 26A:
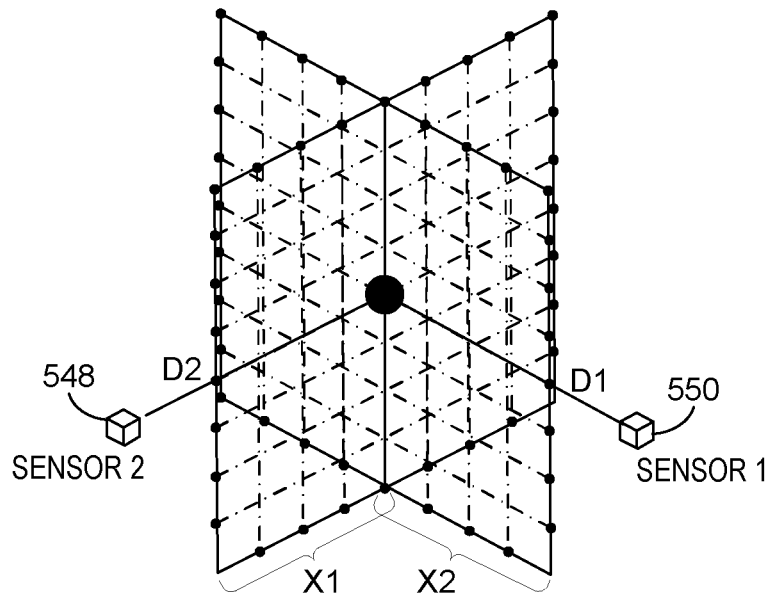
FIG. 26 illustrates the process of aligning the 2D coordinate spaces of FIG. 25 to create the 3D coordinate space of FIG. 24.
Figure 26B:
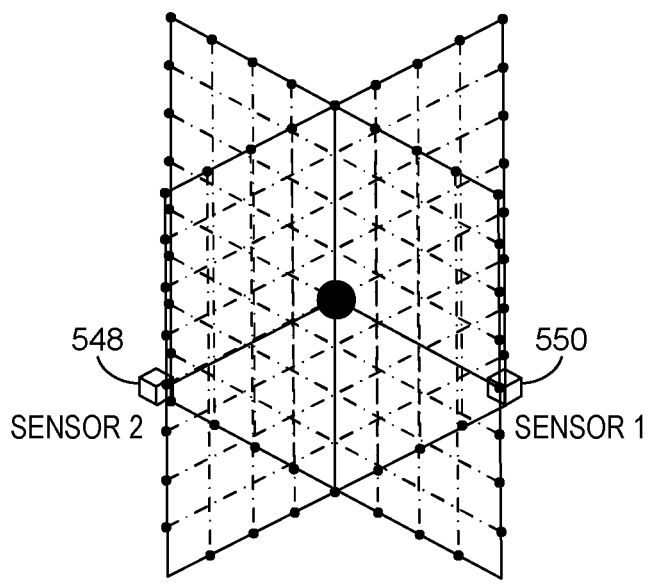

FIGS. 24-26A illustrate this principle. In FIG. 24, a 3D coordinate space 540 is defined by two orthogonal 2D coordinate spaces 542 and 544, corresponding respectively to tracking receivers 548 and 550. In the 2D coordinate space 542, for example, a source point 546 (e.g., the marker LED 522A) has coordinates (X1,Y1). In the 2D coordinate space 544, the same source point 546 has coordinates (X2,Y2). The distance of each of the tracking receivers 548, 550 from the source point 546 may be defined, respectively, as D1 and D2. Thus, by knowing the distances D1 and D2 of the respective tracking receivers 548 and 550 from the source 546, the coordinate spaces 542 and 544 may be aligned by using measurements from each of the tracking receivers 548 and 550. Specifically, the distance D1 between the tracking receiver 548 and the source 546 is equal to the value X2 plus a calibration value CAL2, and the distance D2 between the tracking receiver 550 and the source 546 is equal to the value X1 plus a calibration value CAL1 (see FIGS. 25, 26A). (Of course, in the depicted example, the value X2 is defined from an origin O2, while the value X1 is defined from an origin O1. If, instead, the origin of the 2D coordinate space 544 is defined as the point O2', the value X2 is determined by subtracting a value of X2' from the length of the coordinate system (X2'+X2).) The distances D1 and D2 between the respective tracking receivers 548 and 550 and the source 546 may be determined by, for example, placing the marker LED at a known position relative to the tracking receivers 546 and 550 during a calibration routine. This process is repeated for each of the marker LEDs 522 to obtain additional degrees of freedom.

In practice, each sensor creates the respective independent 2D coordinate space that is pixelated and, thus, the raw data provided by the sensors in the tracking receivers must be converted from pixel values to distance. This may be accomplished by the formula $$(N_x, N_y) = (F \times d) \cdot (P_x, P_y)$$

where $N_x$ and $N_y$ are the position of the optical marker, F is a conversion factor according to the size of the pixels and the units of distance, d is the distance between the sensor and the optical marker, and $P_x$ and $P_y$ are the raw x and y pixel values given for the location of the optical marker in the 2D coordinate system.

Once the coordinates $(N_x, N_y)$ for the optical marker's position have been determined, the corresponding values for X1 and X2 can be determined and, therefrom, the calibration values CAL1 and CAL2 can also be determined. From that point forward (until the coordinate system changes, e.g., during reset of the system) the system will add the calibration value CAL1 to every value X1 determined for the marker LED, and will add the calibration value CAL2 to every value X2 determined for the marker LED, effectively aligning the respective, orthogonal 2D coordinate systems to create a 3D coordinate system (see FIGS. 26A, 26B). When updating coordinates, the distance in the X direction between the one sensor and the optical marker is the value $N_x$ of the optical marker's position in the coordinate space of the other sensor (see FIG. 26B). That is, $N_x$ as determined from the viewpoint of the tracking receiver 548 is input as the value for d for the tracking receiver 550, and $N_x$ as determined from the viewpoint of the tracking receiver 550 is input as the value for d for the tracking receiver 548. Likewise, the distance in the Y direction between the one sensor and the optical marker is the value $N_y$ of the optical marker's position in the coordinate space of the other sensor. That is, $N_y$ as determined from the viewpoint of the tracking receiver 548 is input as the y offset value for the tracking receiver 550, and $N_y$ as determined from the viewpoint of the tracking receiver 550 is input as the y offset value for the tracking receiver 548.

Figure 27:
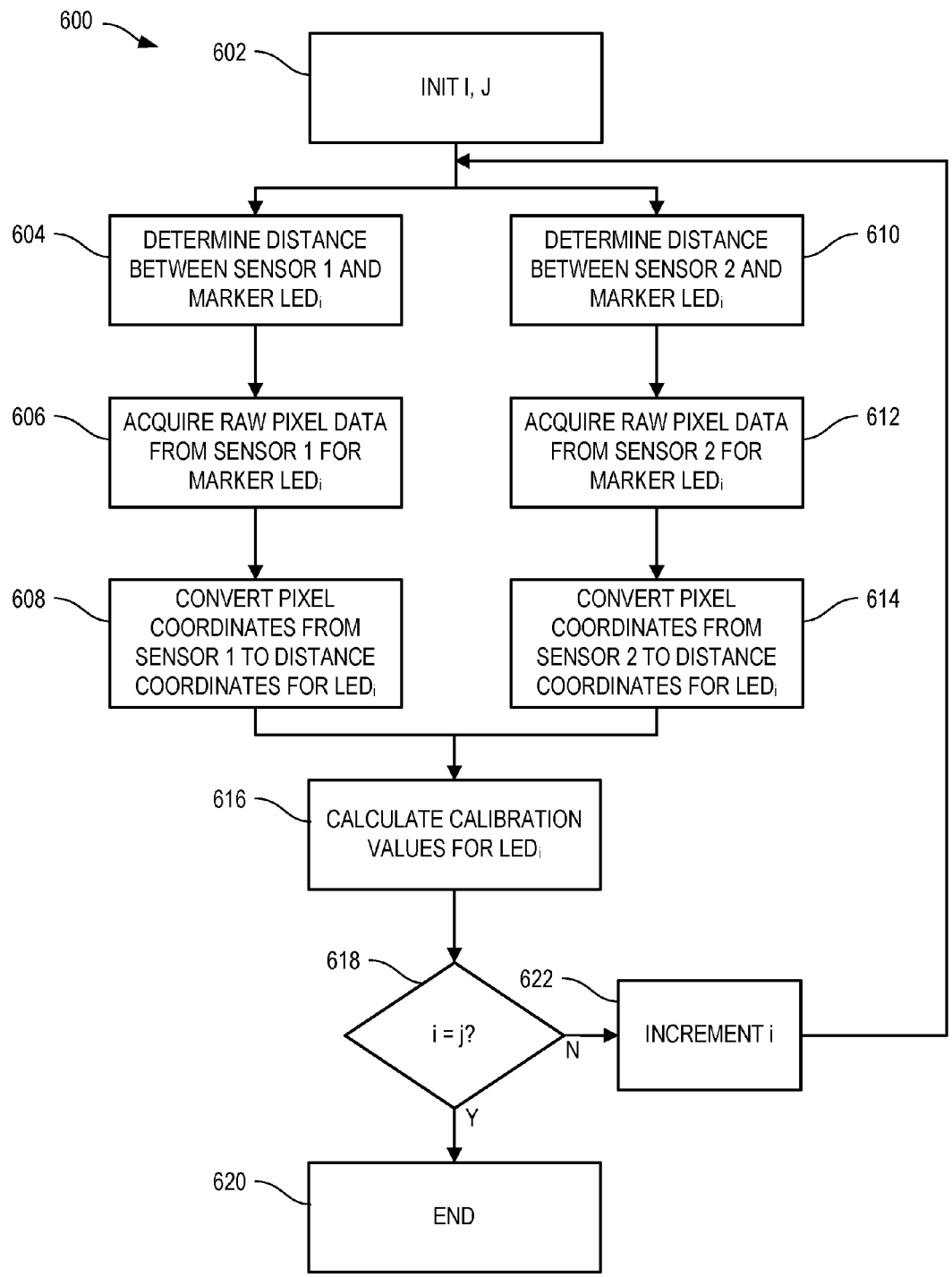
FIG. 27 depicts an exemplary method for calibrating the tracking system in accordance with FIG. 26.

FIG. 27 depicts an exemplary method 600 for calibrating the tracking system 500. A variable i is initialized to 0 (or any desired value) (block 602) and a variable j is initialized to be equal to the number of marker LEDs on each optical marking element, less one (i.e., for optical marking elements having three marker LEDs each, j is initialized to j=2). The distance between a first tracking receiver and a marking LEDi (where i indicates a one of the individual marking LEDs) is determined (block 604). The distance between a second tracking receiver and the marking LEDi is determined (block 610). Raw pixel data is acquired from the first tracking receiver (block 606) and from the second tracking receiver (block 612). The raw pixel data from the first tracking receiver for the marking LEDi is converted to a first distance value for the marking LEDi (block 608) and the raw pixel data from the second tracking receiver for LEDi is converted to a second distance value for the marking LEDi (block 614). The first and second distance values for the marking LEDi are used to calculate calibration values for the marking LEDi (block 616). If i=j (i.e., there are no additional marker LEDs) (block 618), the method 600 ends (block 620). If, on the other hand, i≠j (block 618), then i is incremented (block 622) and the method continues at blocks 604 and/or 610. While the method 600 is described as performing the calibration procedure serially for each of the marker LEDs on an optical marking element, the calibration procedure may also be performed in parallel for each of the marker LEDs on an optical marking element, in some embodiments. For example, the marker LEDs may be illuminated one-by-one in advance of the calibration routine and the pixel location of each (in each tracking receiver) noted. Or, alternatively, the marker LEDs may be modulated (by flashing, changing intensity, etc.) such that each marker LED is distinguishable from the others. As another alternative, the marker LEDs may be differentiated by using different wavelengths for each marker LEDs, or for the marker LEDs of each optical marking element 504. As described above, each optical marking element may be tracked by a corresponding pair of tracking receivers and, therefore, optical marking elements for each probe may be calibrated serially or in parallel.

Figure 28:
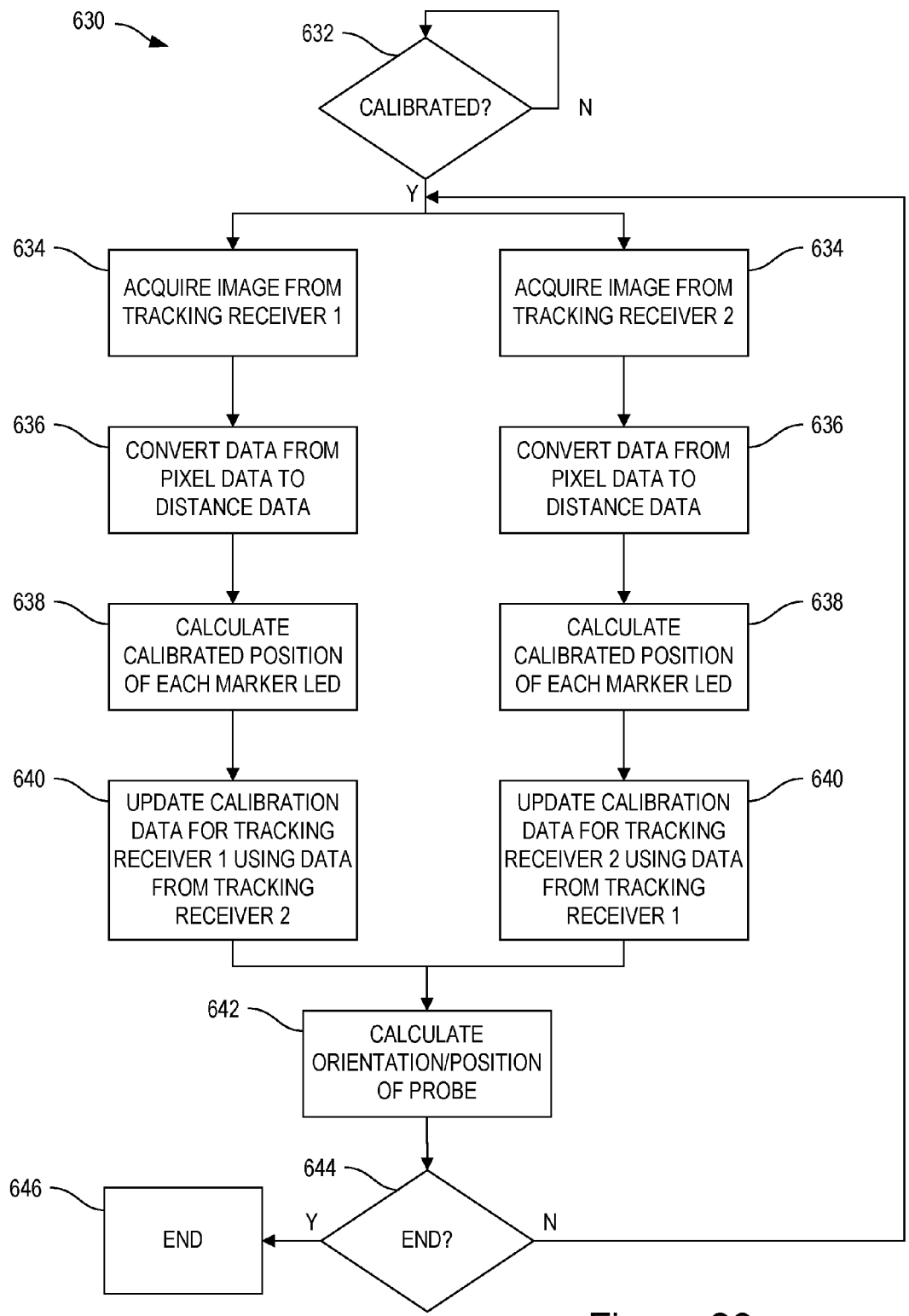
FIG. 28 is a block diagram of a method for tracking the location of a probe head.

FIG. 28 depicts a method 630 for tracking a probe head 100A, 100B or another optical marking element (e.g., the optical marking element 504C attached to the patient). The method 630 commences with a determination of whether the tracking system 500 has been calibrated (block 632). If calibration is completed, the method 630 proceeds to acquire sensor images from the tracking receivers (block 634) for the optical marking element. The data from the raw tracking receiver images is converted, for each of the marking LEDs, from pixel data to distance data (block 636), and the calibrated position of each of the marker LEDs is calculated (block 638). Calibration data for each tracking receiver is updated according to the data received from the other tracking receiver (block 640). That is, the current distance between each marking LED and the first tracking receiver is updated using data from the second tracking receiver, and the current distance between each marking LED and the second tracking receiver is updated using data from the first tracking receiver. Using as input the positions of each of the marker LEDs, and the known geometric relationships between the marker LEDs, the position and orientation of the optical marking element (and the corresponding probe head or 3D mesh) is calculated using triangulation and/or vectors of movement (block 642). If an "end" instruction has not been received (block 644), the method repeats from the block 634. Alternately, if an "end" instruction has been received, the method ends (block 646).

Of course, the method 630 is completed for each optical marking element with data received from a corresponding pair of tracking receivers. Thus, the method 630 may be executed, in parallel or series, for each optical marking element (i.e., for each probe head 100A, 100B) and, optionally, for an optical marking element corresponding to the 3D mesh. Executing the method 630 in parallel for each of the optical marking elements may result in improved performance.

Each of the tracking receivers may be in wired or wireless communication with the processing unit 430 via the communications interfaces 435 and 512. Accordingly, each of the calculating, determining, converting, and/or updating steps in the methods 600 and 630 may be performed by the processing unit 430. In some embodiments, the processing unit 430 performs the methods 600 and/or 630 in cooperation with one or more processors (not shown) in the tracking receivers.

Coregistration

Figure 29:
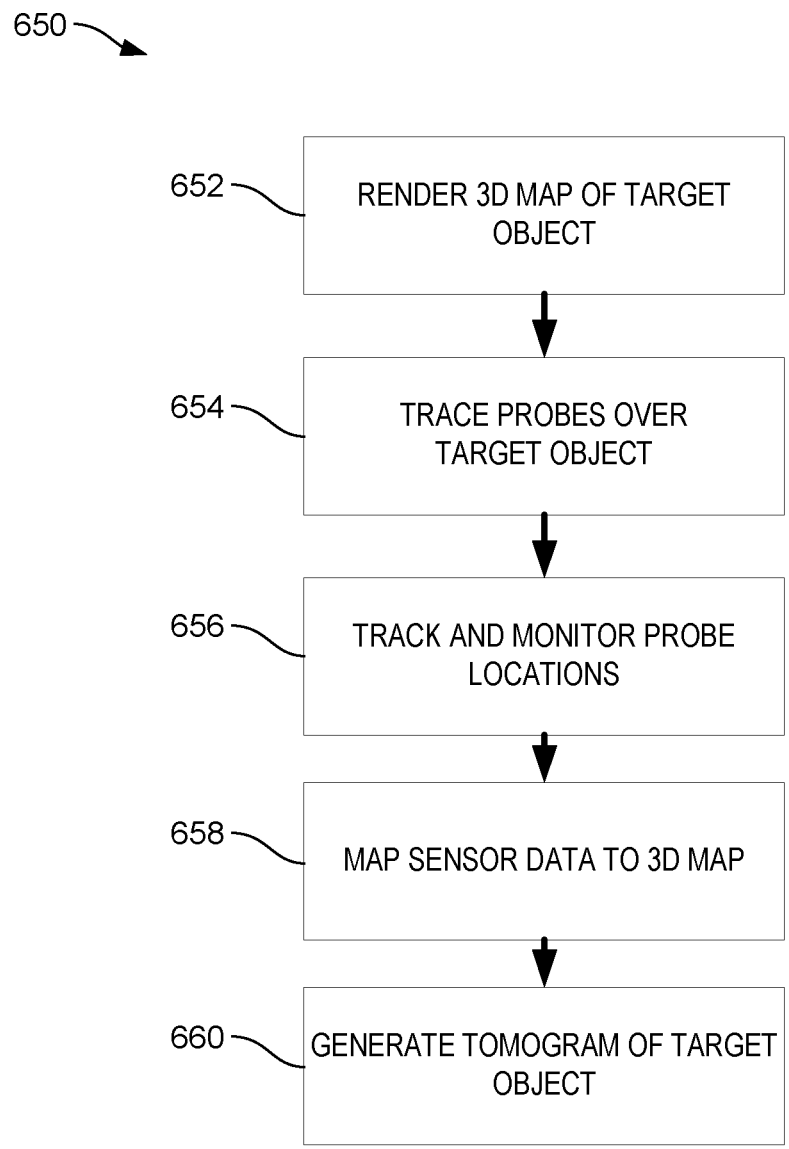
FIG. 29 is a block diagram of a method of producing tomograms of a target tissue object.

FIG. 29 illustrates an exemplary embodiment of a method 650 for coregistering tracking data with probe image data to produce tomograms of a target tissue object. A three-dimensional scanner and appropriate meshing software may be used to render a three-dimensional map (e.g., a mesh of point locations) of the target three-dimensional tissue object (block 652). Thereafter, imaging probes (e.g., the probe heads 100A, 100B of the probe assembly 200) may be traced over the target tissue object (block 654). As the probes are traced over the target tissue object and sensor data are recorded from each probe, the positions of the probes are tracked and recorded (block 656) using, for example, the tracking system 500 described above. Timed sensor data may then be mapped to a location on the 3D map (block 658). In some embodiments, a computer, such as the computer 420 may be programmed to receive sensor data from the probes 100A, 100B at a period of time, to receive location information from the tracking system 500 for the period of time, and to map this data to corresponding points on the 3D map or mesh of the target object. In this manner, a location or coordinate value is associated with the timed sensor data. At block 658 the sensor data may be processed along with the coordinate or location information associated with the sensor data to produce a tomogram of the three-dimensional tissue object using appropriate inverse algorithms (block 660).

In some embodiments, a Bayesian Approximate Extended Kalman Filter (AEKF) based inverse algorithm may be employed for image reconstruction (or tomogram generation) of 3D optical property maps using location registered sensor data from the 3D surface of the target object. In brief, the AEKF-based algorithm may employ measurements and system errors to iteratively reconstruct for unknown parameters. The AEKF algorithm may be modified and/or optimized to reflect unique simultaneous illumination and detection measurement geometry of the imager described above, to apply noise filtration techniques to minimize artifacts during inversions; and/or to synchronize the mesh with the real-time co-registered measurements. These modifications may provide computationally efficient reconstructions. Various inverse algorithms have been developed by other researchers, and any one of them may be used instead of AEKF based algorithm.

The embodiments of the optical imaging system and method described above may use multiple sequential and/or simultaneous illuminating point sources with corresponding sequential/simultaneous multiple point detectors to maximize tissue volume illumination and reduce data acquisition times. In some embodiments, individual ones of the illumination sources may be programmed to illuminate sequentially, simultaneously, or not at all. That is, the system may be programmable to utilize all or fewer than all of the available illumination sources and, accordingly, to illuminate more or fewer points on the surface of the subject being imaged, sequentially or simultaneously, or not at all. The measurement geometry may be implemented as a sub-surface imaging geometry, which allows flexible imaging of large tissue volumes with minimal patient discomfort. The optical imaging system and method may have applications not only in breast imaging, but also for any other tissue or phantom imaging.

Moreover, the optical imaging system using tracking facilities and the location/sensor data registration process (FIG. 29) may provide a highly efficient method of reconstructing the optical property maps of 3D tissue structures including 3D sub-surface structures. Existing optical tomography towards breast cancer diagnostics is generally restricted to slab geometries representing compressed breast tissues or to cup-shaped breast phantoms of fixed volumes, wherein single point illumination configurations are typically employed. Compression of breast tissue is generally uncomfortable to patients and non-compressive techniques are usually preferred.

As described above, co-registration is the process of aligning image data (of a plane or volume) with other image data and/or location data within the same coordinate space. Two types of co-registration techniques exist: intermodality and intramodality. Intermodality co-registration aligns image data of different modalities, whereas intramodality co-registration aligns image data from the same modality. Intermodality co-registration is beneficial because it enables the combination of multiple images (i.e., multiple image types) such that the advantageous characteristics of each are combined into a single image, enhancing the quality of the final image. Intramodality co-registration is beneficial because it enables the alignment of image data at different locations from the same modality such that the data can be used to determine the three-dimensional location of a point of interest or to reconstruct a volume. The disclosed method and system use intramodality co-registration to obtain co-registered, three-dimensional surface images from two-dimensional surface data, which three-dimensional surface images may be used for three-dimensional tomography. Of course, as used herein, the term "real-time" does not necessarily indicate that data and/or images are updated at the same rate or greater rate as the data and/or images are received. As used herein, use of the term "real-time" indicates a lack of significant delay or lag time, and may include embodiments in which data and/or images are updated at the same rate or greater rate as the data and/or images are received. For example, the term "real-time" may indicate that an action (e.g., data processing) or event (e.g., display of an image) occurs within as much as several seconds from acquisition of the data, or may indicate that the action or event occurs within a second, or less than a second, from the data acquisition.

Co-registration of probe image data with a discretized 3D mesh mandates that the geometry of the probed 3D geometry (with which the image data is being co-registered) be known. The 3D geometry can be determined by a user's previous knowledge of the 3D geometry or by using a three-dimensional laser scanner (e.g., the 3D mesh generation assembly 410), which may automatically acquire the 3D geometry. Once the tracking system 500 provides the locations of the probes 100A, 100B, and the optical image data (from both probes) are obtained using the optical imaging system, the image data from each probe head 100A, 100B can be co-registered onto a discretized 3D mesh at the true location of the data for each respective probe.

Figure 30A:
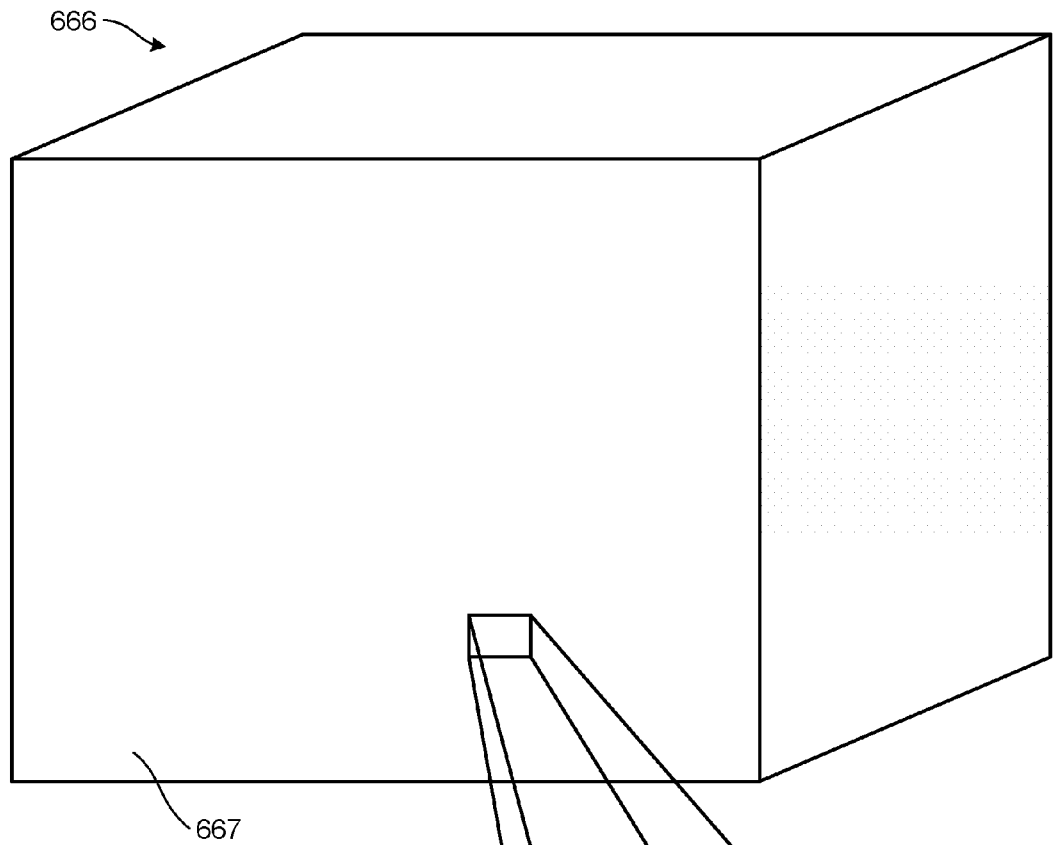
FIG. 30A depicts an exemplary 3D mesh in accordance with the presently described system.
Figure 30B:
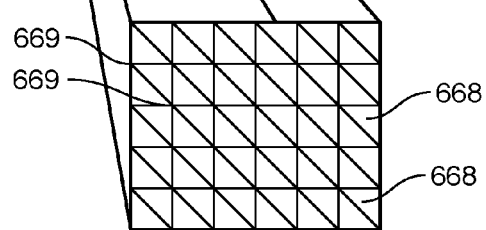
FIG. 30B depicts an enlarged view of a portion of the exemplary 3D mesh of FIG. 30A.

FIGS. 30A and 30B depict, respectively, a 3D mesh 666 having a surface 667, and an enlarged portion of the 3D mesh 666, showing the surface 667 discretized into a plurality of triangular faces 668 and vertices 669. To co-register optical image data with the 3D mesh 666, each data point (i.e., data from each of the detectors on the probe) is co-registered with a vertex 669 that is nearest to the detection point on the 3D mesh's surface 667, and the corresponding face 668 is assigned an appropriate optical intensity-equivalent color value based on the data. Prior to co-registration of current data with the 3D mesh 666, the color on the surface 667 of the 3D mesh 666 will be dependent on whether or not previous image data have been co-registered onto the 3D mesh 666.

Figure 31:
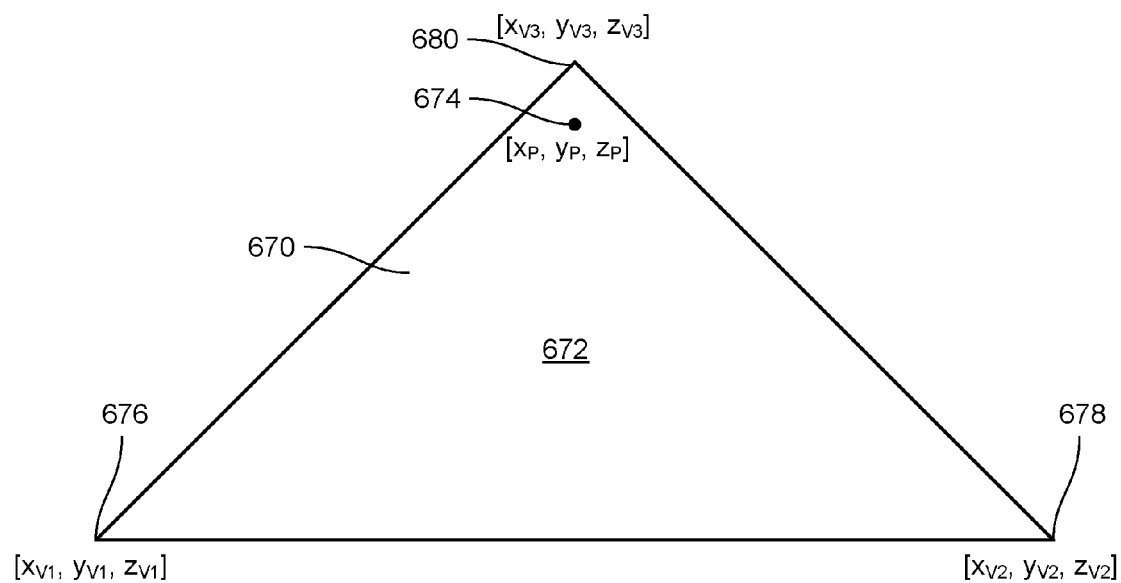
FIG. 31A illustrates a single fiber optic point placed randomly on a triangular face of the 3D mesh surface illustrated in FIG. 30B.

With reference to FIG. 31, when a single triangular face 672, such as the triangular face 670, defines a surface 672 of a 3D mesh (such as the 3D mesh 666), the triangular face 670 is defined by three vertices 676, 678, 680, at points $[x_V, y_V, z_V] = [x_{V1}, y_{V1}, z_{V1}; X_{V2}, y_{V2}, z_{V2}; X_{V3}, y_{V3}, z_{v3}]$, respectively. A single fiber optic point 674 is placed randomly on the surface 672 of the triangular face 670 at a point $[x_P, y_P, z_P]$. By determining the distance $V_D$ from each vertex 676, 678, 680, the closest vertex to the point 674 can be calculated by finding the minimum value from a set of $V_D$ values.

The algorithm (described below) implemented to calculate optical intensity-equivalent color values detected at each point of the 3D mesh 666 may be a vertex-by-vertex implementation in which a distance $V_D$ of a fiber optic point from every vertex 669 on the 3D mesh 666 is calculated by a computer (not shown). $V_D$ may be determined according to the equation:

$$V_D = \sqrt{dx^2 + dy^2 + dz^2} = \sqrt{(x_V - x_P)^2 + (y_V - y_P)^2 + (z_V - z_P)^2}$$

The minimum distance from the set of values may be determined by the computer and the point correlating with that minimum distance is assigned the optical intensity-equivalent value of the point on the probe. The colors of the triangular faces 668 are determined by interpolation of each vertex 669 of the triangular faces 668 via the software. It should be noted that, while the algorithm is described in terms of optical intensity data and color values, any optical data may be mapped to the 3D mesh 666, including AC data, DC data, modulation data, phase shift data, etc.

Once a minimum for $V_D$ is found by the computer 420, the optical intensity-equivalent color value at the single fiber optic point 674 can be assigned to the nearest vertex (e.g., the vertex 680) and the values of all other vertices 676, 678 can be interpolated to enable shading of the triangular face 670. In FIG. 31, the fiber optic point 674 is near the top vertex 680 of the triangular face 670. Accordingly, the vertex 680 is assigned a color, corresponding to an optical intensity at the fiber optic point 674.

For 3D meshes with a small number of vertices, the aforementioned algorithm is sufficient. However, as the complexity of the geometry of a 3D mesh increases, the number of vertices 669 and faces 668 must be increased to better resolve intricate patterns of curvature in the geometry. This amounts to a 3D mesh with many more vertices and faces than a simple case. The aforementioned algorithm implements a vertex-by-vertex search over the entire 3D mesh, making it computationally inefficient in cases where high mesh resolution is required.

To address this problem, exclusion code logic is implemented whereby only 3D mesh vertices 669 within a certain range 'b' (buffer zone) of the probe face are incorporated into minimum distance calculations. This buffer zone can range from b=0, where only the 3D mesh vertices in direct contact with the probe are searched, to b=the maximum length of 3D mesh, in which case all vertices of the 3D mesh are included in the search. This significantly decreases processing time for large 3D meshes depending, of course, on the processing hardware on which the software embodiment of the algorithm is running.

As much as the processing hardware may affect the processing time for large 3D meshes, achieving automated real-time co-registered imaging requires minimal time delay between data acquisition and display. A major concern during automated real-time co-registration is that several processes need to be running simultaneously, some of which may demand considerable processing time and thereby increase the time lag between the time the image is acquired and the time the image is displayed. These processes are (in descending order of computational demand): (i) co-registration of image data from each probe onto the correct location of a corresponding 3D mesh; (ii) real-time image data acquisition from each probe; (iii) the saving/display of data; (iv) real-time tracked location of each probe; and (v) miscellaneous background processes (e.g., antivirus, web browser, etc.). The simplest solution resulting in decreased time lag and, thereby, increased processing speed, is to implement one or all of the following: (i) close all unnecessary background processes; (ii) increase random access memory (RAM); and (iii) increase processing capabilities (i.e., faster central processing unit (CPU) and increased RAM). In the disclosed embodiment, the issue is addressed by using a state of the art workstation computer dedicated strictly to this system.

Implementing efficient programming code is also important in a well-built co-registration program. Moreover, an intuitive graphic user interface (GUI) facilitates the process by providing users with a dynamic array of options meant to enhance visualization and display schemes as well as optimize data processing techniques. Some of the features of the developed co-registration software are its powerful ability to: (i) upload any set of face and vertex data corresponding to a 3D mesh; (ii) adjust the on-screen position/orientation of a 3D mesh to match its real-time location; (iii) use simulated or real-time image data in co-registration; (iv) auto-normalize color data over the range of intensities of an entire co-registered 3D mesh; (v) retain/erase image data acquired during a previous scan; (vi) acquire and display real-time probe location/orientation; (vii) adjust the on-screen angle of the probe's outer plates to match its real-time angles; and (viii) save all displayed information into a single file (e.g., a MATLAB .mat file) for post-process analysis.

Figure 32:
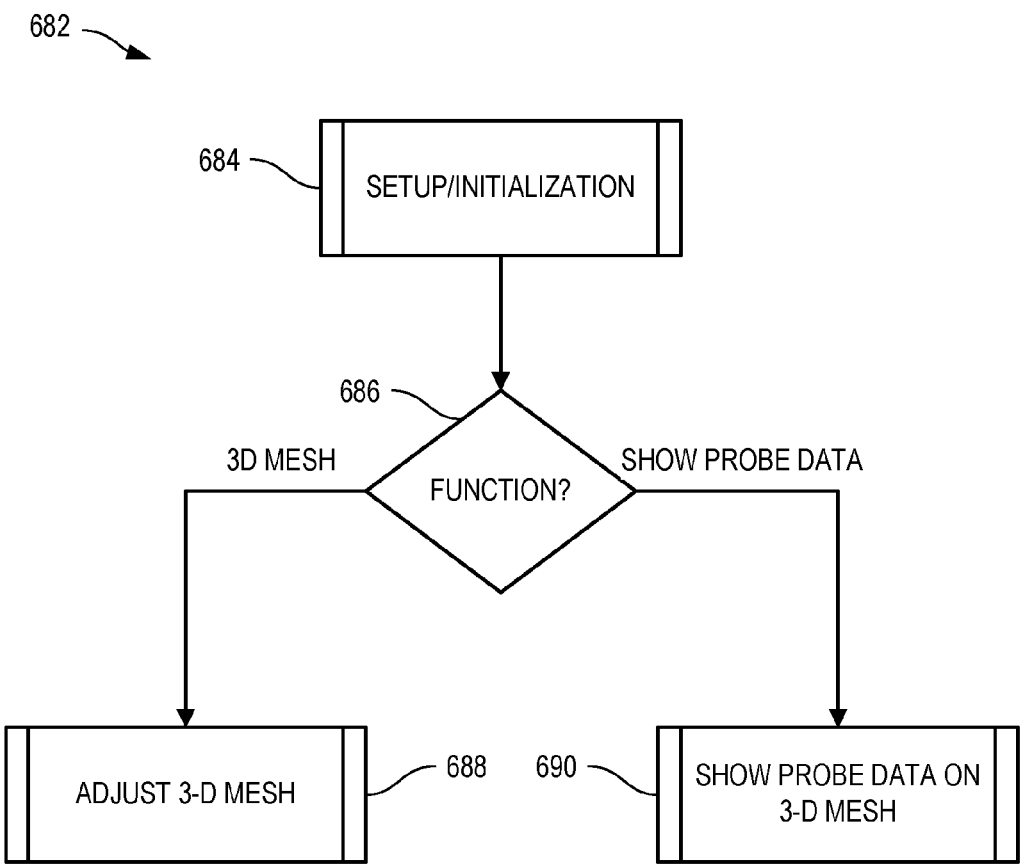
FIG. 32 is a block diagram of a method for performing co-registration in accordance with the presently described system.

Real-time co-registration software processes and displays the image data received from the probes, using the data of the 3D mesh and the data of the probes' locations. The software may be implemented in any suitable high-level programming language such as, for example, MATLAB, LabVIEW, C, C++, etc., or in a combination of high-level programming. In some embodiments, the software is implemented in a combination of MATLAB and LabVIEW. In particular, a disclosed embodiment implements MATLAB code included in a program written in the LabVIEW programming language to automate the process of image data and probe location data acquisition such that as the tracker changes the location coordinates and orientation, the software updates the location and orientation of the probe—and thus the location of the corresponding image data—accordingly, with minimal lag in real-time. The software, stored on a tangible, non-transitory media as computer-readable instructions, implements a method, similar to a method 682 in FIG. 32, the software including one or more routines and/or sub-routines. The method 682 begins with setup/initialization (block 684). The software may determine (block 686) what the user wants to display in accordance with an input from a graphical user interface (GUI). The software may then run a routine to adjust the 3D mesh (block 688) or a routine to show the probe data on the 3D mesh (block 690).

Prior to initiating the method 682, the software may display the GUI to collect information from the user, including parameters such as a file name, the parameters (e.g., vertices and faces) of the 3D mesh (or directories where files containing the parameters are stored), a COM port number from which to read the probe data and/or the locations of the probe 100A, 100B, calibration values for CCD hardware on the probes, distances between the tracking receivers and the optical marking elements (or the marker LEDs of the optical marking elements), a relative position of the 3D mesh, viewing angles, probe reference location(s), 3D mesh resolution, etc. The user may place each probe head 100A, 100B such that the corresponding optical marking element is located at a fixed (or at least known) reference point. Upon execution of the method 682, the software setup/initialization (block 684) reads the parameters defined by the user and initializes the probe locations according to the methods described previously and, for example, according to the calibration method 600 of FIG. 27.

Figure 33:
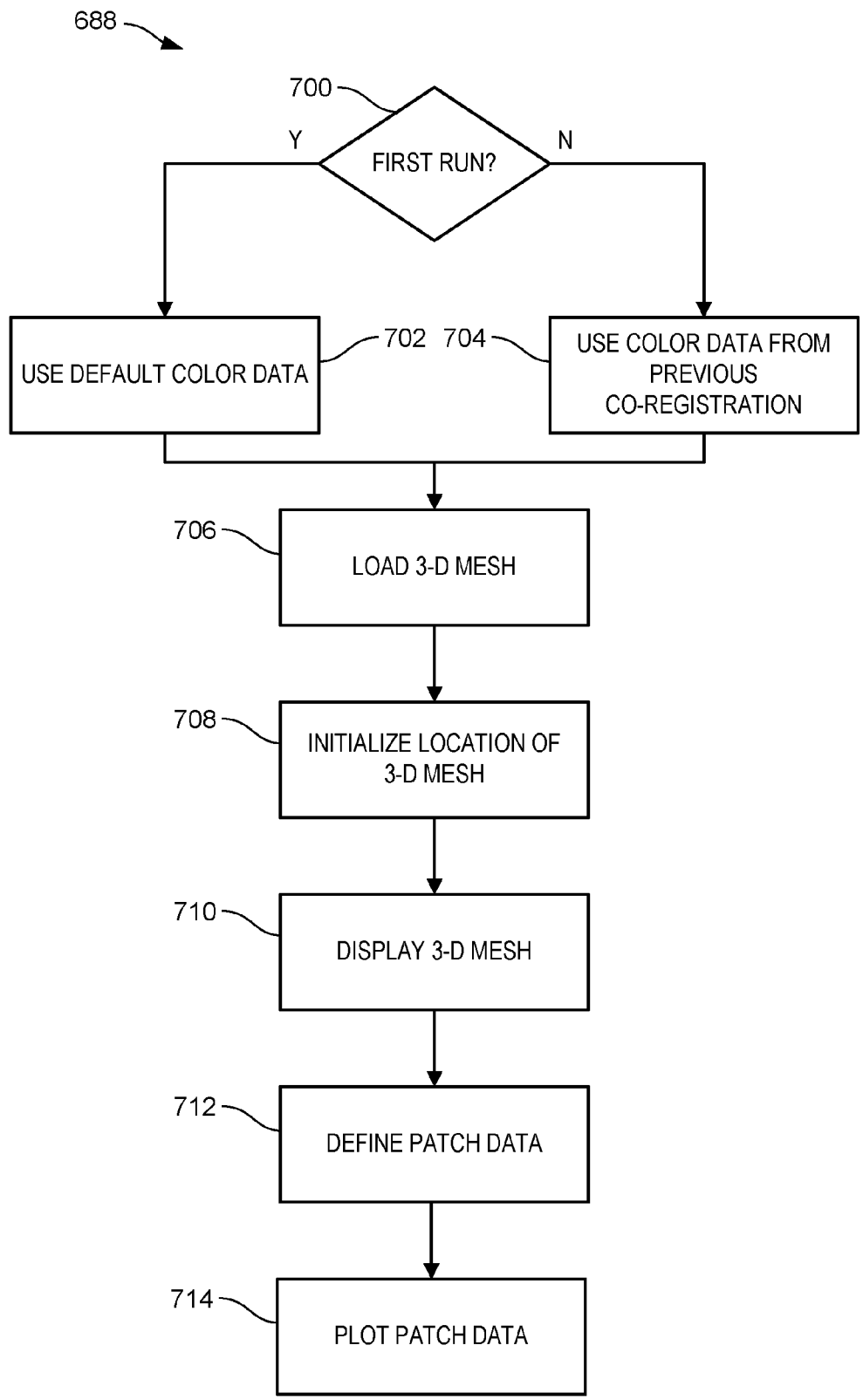
FIG. 33 is a block diagram of a method of adjusting a 3D mesh in accordance with an embodiment of the presently described system.

If the software determines (at block 686) that the user has indicated through the GUI to show the 3D mesh and allow adjustments (block 688), the software may proceed as illustrated in FIG. 33 (blocks 700-714). If the software is executing the block 688 for the first time since the software was executed (i.e., no co-registration has yet been performed) (determined at block 700), the software may use the default color data for the vertices and faces of the 3D mesh (block 702). Alternatively, if the software is not executing the block 688 for the first time since the software was executed (i.e., if the option is selected so that the user may adjust the position of the 3D mesh), the software may use color data from previous co-registration (block 704).

In any event, in a disclosed embodiment the software loads the 3D mesh (block 706), for example from the files specified in the GUI by the user. It is worth noting that, because the co-registration process is executed for each of the probes independently, the 3D mesh is loaded as a separate instance for each of the probes. The location of the 3D mesh is locked to the origin (block 708) determined previously. The 3D mesh may be displayed at this point (block 710). In some embodiments, the software creates a visual display of the 3D mesh that depicts the entire 3D mesh as having a single color because no color data have yet been overlaid on the 3D mesh. In some embodiments, the software will depict the 3D mesh as having the colors associated with the data from the previous measurements. The software may then define, by patch data, a patch (i.e., may specify the coordinates that define the vertices of each face and the elements that define the connectivity of each face) (block 712) of a probe mesh (not to be confused with the 3D mesh representing the surface of the subject being imaged) for each probe, representing the respective probe face and with which probe optical data collected by the respective probe may be aligned.

The software next may plot the patch data for the probe (block 714) as a three-dimensional probe mesh with respect to the 3D mesh. The points on the probe mesh correspond to the ends of the detector fibers for that probe. The location of each detector fiber is specified by a set of x, y, and z coordinates. In some embodiments, plotting the patch data includes getting the vertices data, adding values of dx, dy, and dz (which may be received via the GUI) to the data so that the 3D mesh and the probe mesh can be moved in real time according to inputs via the GUI from the user, and/or getting the pitch, yaw, and roll data. In some embodiments, getting the pitch, yaw, and roll data may include defining an x-axis of the 3D mesh, defining a y-axis of the 3D mesh, defining a z-axis of the 3D mesh, and/or defining a center of the 3D mesh. In at least one embodiment, the 3D mesh may be symmetrical about the defined x- and y-axes so that the software may rotate the 3D mesh around the center point of the 3D mesh. In some embodiments, the z-axis remains fixed so that the 3D mesh remains constant on the z-plane.

Figure 34:
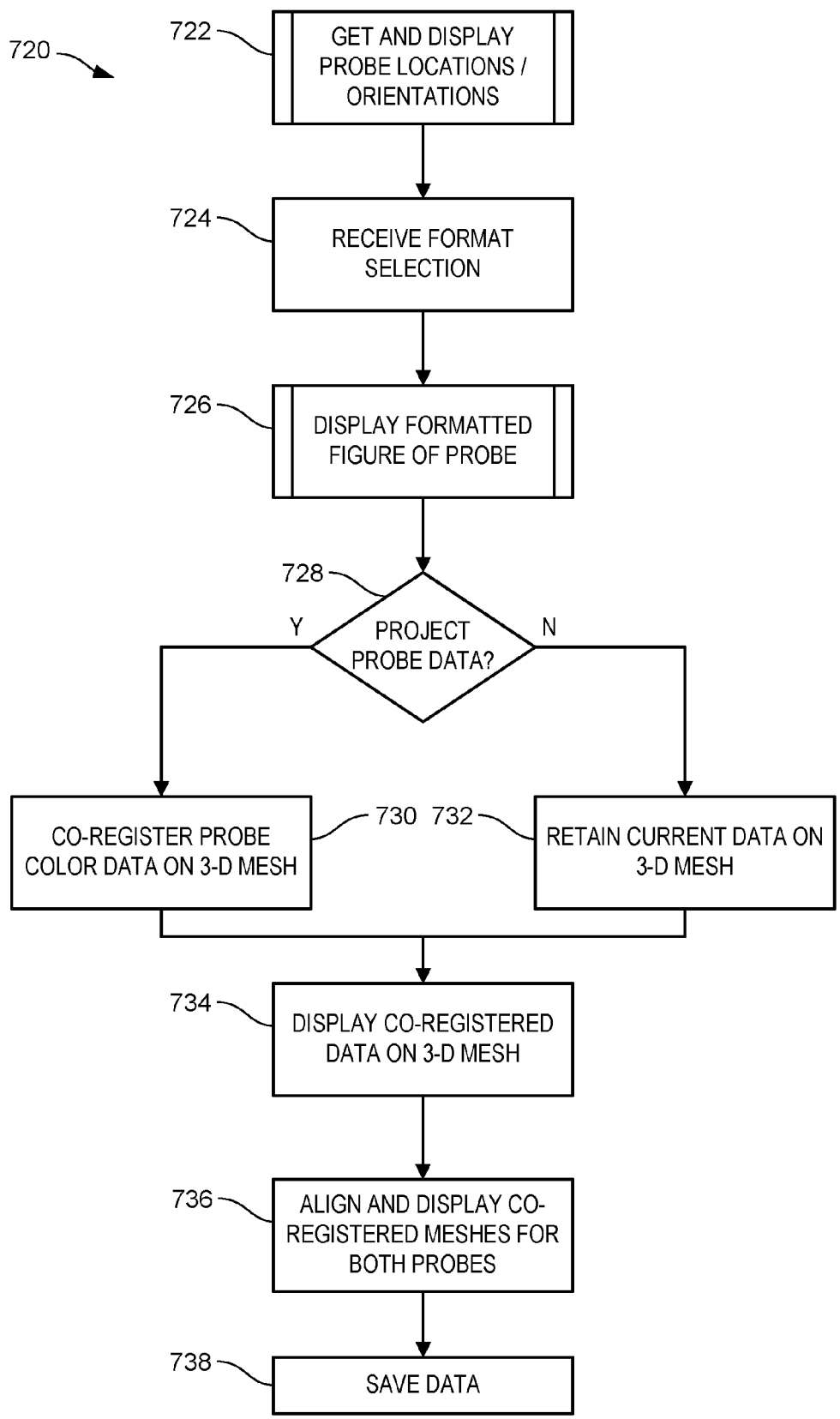
FIG. 34 depicts a method of displaying probe data on a 3D mesh in accordance with an embodiment of the presently described system.
Figure 35:
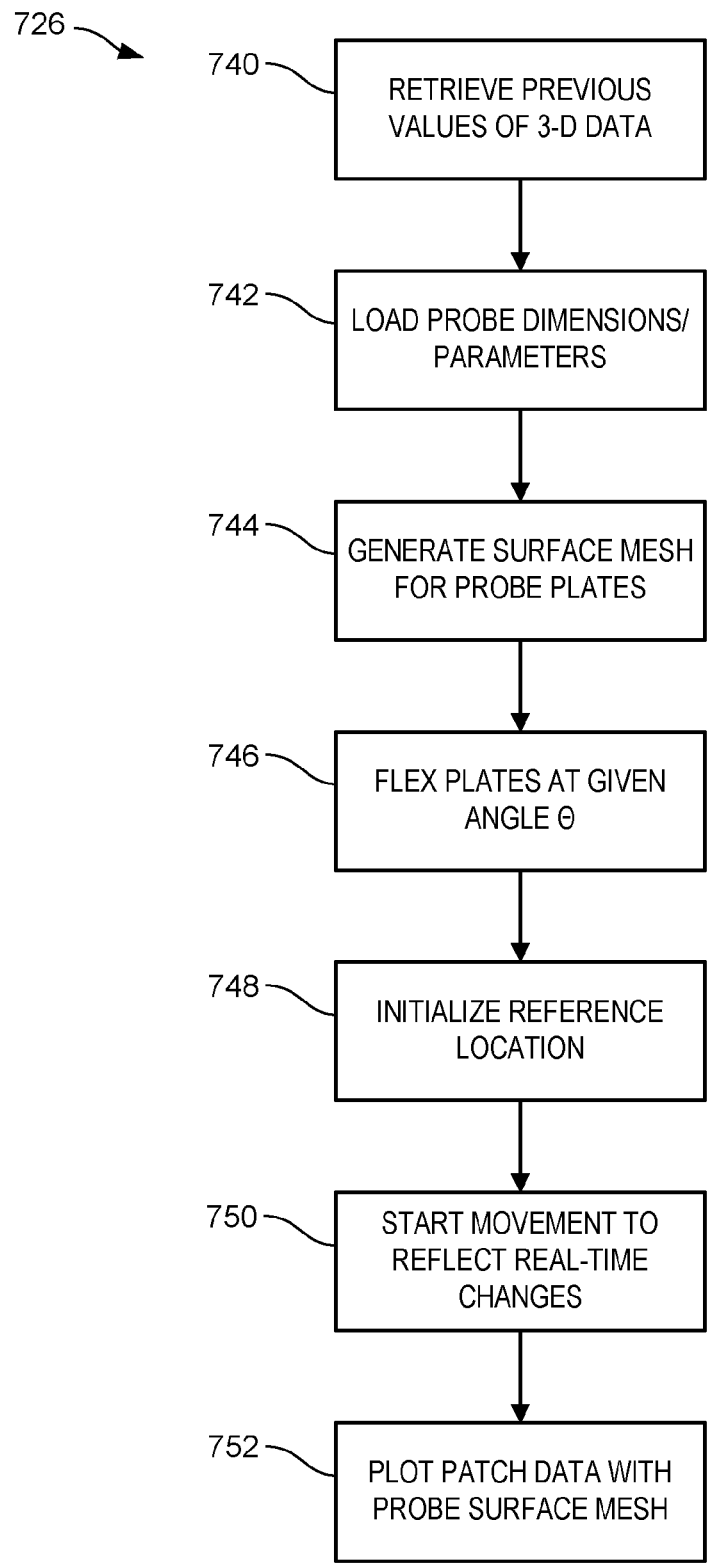
FIG. 35 depicts a method of displaying probe location and orientation in accordance with an embodiment of the presently described system.

If instead the software determines (at block 686) that the user has indicated through the GUI to show the probes relative to the 3D meshes (block 690), the software may proceed with a method 720 as illustrated in FIG. 34 (blocks 722-736). The software may first determine and display the position and orientation of the probe 100 (block 722), which may proceed according to the method 630 of FIG. 28. The software may determine one or more parameters related to the probe and/or the 3D mesh format received from the user through the GUI (block 724). When the one or more parameters have been received, the software displays the formatted figure of the 3D mesh with the probe (block 726). With reference now to FIG. 35, displaying the formatted figure of the 3D mesh with the probe may include retrieving previous values of 3D mesh data (block 740). The 3D mesh data may be used at a later point when the user selects to adjust the 3D mesh 688. The software may also load information about probe dimensions and/or parameters (block 742), including information about probe width, information about probe height, real-time image color data, resolution factor of the 3D mesh, point locations along the width of the probe of the hinges where the plates of the probe flex, angles theta (θ) of the structures 120A and 120E with respect to the structure 120C, etc. The software next generates a 3D probe mesh for the probe plates (block 744). That is, the software will determine the position of each of the detector fiber ends on the probe plates, and generate a corresponding 3D probe mesh, according to the information and/or parameters determined (block 742). Once the 3D probe mesh for the probe face has been generated (block 744), the software adjusts the position of the detector fiber ends according to the given angle theta (θ) (block 746) as determined from the information specified by the user through the GUI (block 742). In alternate embodiments, the software may adjust the position of the detector fiber ends by assuming that the probe face 102 contours close to 100 percent with the surface of the subject being imaged and, therefore, that each of the detectors can be projected onto the 3D mesh.

Following the generation of the 3D probe mesh corresponding to the probe plates with the appropriate plate angles, the software may initialize reference location (block 748). This may include one or more of retrieving the initial positional data (x, y, and z locations) for each of the points on the probe (obtained during setup (block 684)), setting the new positional data for each point on the probe by adding the current data to the initial data, and saving the new positional data for each of the points on the probe faces. It may also include defining the x, y, and z axes of the probe, defining the rotation of the probe about each of the x, y, and z axes (i.e., the pitch, yaw, and roll values for the probe), and rotating the probe image about each of the axes according to the rotation of the probe. The surface mesh corresponding to the probe surface may be updated in real time.

After initializing the reference location (block 748), the software may begin real-time tracking and movement of the probe location (block 750). The real-time tracking and movement of the probe location may include updating the surface mesh for the probe (i.e., the probe mesh) to reflect changes to the location and orientation of the probe. Lastly, the software may process the color data of the patch currently imaged by the probe, and combine the patch color data with the probe surface mesh (block 752). This results in a real-time image of the surface imaged by the probe.

Referring again to FIG. 34, the software may next determine (block 728) whether the user has, through the GUI, indicated a desire to project the image of the current probe data (color data) onto the 3D mesh of the object being probed. If the software determines that the user has selected for the projection of the color data onto the 3D mesh, the software may co-register current probe color data on the 3D mesh (block 730) (i.e., may co-register the probe mesh with the 3D mesh). This may require rounding of location data, or other similar mechanisms, to allow the software to superimpose the color data for the probe patch onto the 3D mesh vertices. For example, if a 3D mesh vertex location is 23.124 and a probe patch vertex location is 23.125, then the values for the "two" vertices are obviously the indicative of the same vertex. The software may allow for rounding the numbers so each reflects a value 23.12 and allows the software to reassign the color data accordingly. Alternatively, if the software determines that the user has not selected for the projection of the data onto the 3D mesh, the software may co-register default or previous probe color data on the 3D mesh (block 730). The software then displays the co-registered data on the 3D mesh (block 734). When the probe data for each probe have been coregistered with the 3D mesh (according to the blocks 722-734), the 3D mesh loaded for each probe maybe aligned and displayed so as to display simultaneously on a single 3D mesh the image data from both probes (block 736). Optionally, the software may save the data (block 738). Alternatively, the probe data for each probe may be displayed on a respective 3D mesh adjusted to have a corresponding 3D orientation.

Of course, it will be apparent that the imaging data (i.e., color data) obtained at each of the detector point locations on each probe may be co-registered with the 3D mesh of the object being imaged, instead of first co-registering the imaging data from each detector point location with a 3D mesh of the probe (i.e., the probe mesh) and then co-registering the probe mesh along with the imaging data on to the 3D mesh. Thus, in some embodiments, the probe color data may be projected directly onto the 3D mesh of the imaged object, while in some other embodiments the probe color data may be projected onto a probe mesh representative of the probe face, which may, in turn, be co-registered (i.e., aligned) with the 3D mesh of the imaged object. Additionally, in a disclosed embodiment the probe may be displayed (with or without the probe mesh) in some embodiments, the probe may not be displayed at all, or the probe mesh may be displayed without the probe.

Figure 36:
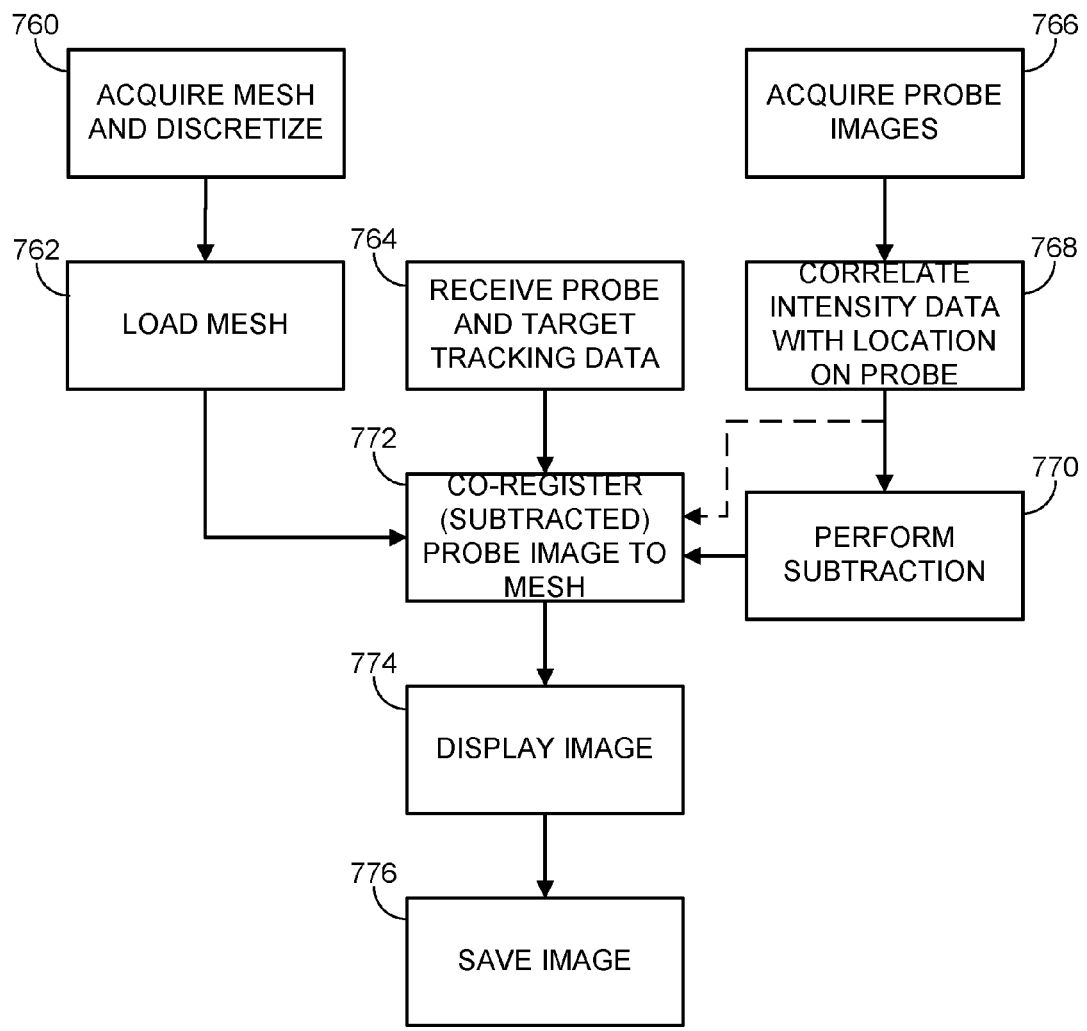
FIG. 36 a block diagram of an exemplary embodiment of broadly encompassing the methods depicted in FIGS. 27-29 and 32-35.

FIG. 36 broadly depicts, in an exemplary embodiment, the methods described herein with reference to FIGS. 27-29 and 32-35. Specifically, a 3D mesh is acquired via the 3D mesh generation assembly 410 and the computer 420, and the 3D mesh is discretized (block 760). The discretized 3D mesh is loaded as a separate instance for each probe head (block 762). Tracking data for each probe is acquired from the tracking system 500 (block 764). Imaging data are acquired from each probe (block 766) and the computer system 420 correlates intensity data (or AC or DC or modulation or phase shift data, i.e., any optical data) with the location on the corresponding probe (block 768). In an optional step, background image data common to images acquired from a probe or common to both probes may be subtracted from one another to obtain a subtracted image to improve contrast between a target (e.g., a tumor) and the background tissue (block 770). The probe image (or the subtracted probe image) is co-registered to the 3D mesh using the tracking data (block 772). Optionally, the co-registered image may be displayed (block 774) and/or saved (block 776).

The methods described herein with reference to FIGS. 27-29 and 32-35 may include more and/or additional processes and/or data manipulation, may omit processes and/or data manipulation described herein, and may, in some instances, execute processes and/or data manipulation in an order different than described herein. For example, in some embodiments, one or more software modules for acquiring and/or interpreting data from the tracking system 500 may be separate from one or more software modules for acquiring and/or interpreting data received from the probe ends of the detector optical fibers. Similarly, some embodiments may have one or more software modules for co-registering location data and detector data. Of course, various functions may be combined into one or more software modules, which may provide advantages with respect to processing speed, memory allocation and/or memory requirements, system responsiveness, algorithm efficiency (i.e., changing the order of the executed instructions), etc. Additionally, while methods described with reference to FIGS. 27-29 and 32-35 are described as embodied in one or more software applications, a person of ordinary skill in the art will readily appreciate that specialized hardware may be programmed and/or fabricated to replace any aspect otherwise embodied as software.

Reference throughout this specification to "one embodiment", "an embodiment", or a specific "embodiment" means that a particular feature, structure, or characteristic described in connection with the embodiment is included in at least one embodiment and not necessarily in all embodiments, and further, are not necessarily referring to the same embodiment. Furthermore, the particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention. By way of example, and not limitation, the present disclosure contemplates at least the following aspects:

1. A method for performing co-registered optical imaging, the method comprising:

acquiring a three-dimensional (3D) surface outline of the subject to be imaged;

representing the three-dimensional surface outline as a discretized mesh;

using two or more probes of a probe assembly to acquire an optical signal at a surface of the subject;

tracking one or more markers on each probe of the probe assembly;

receiving, via an imaging system coupled to the probe assembly, the optical signal captured by the probe assembly;

converting the optical signal to image data; and co-registering to the mesh the image data to form an image.

2. The method according to aspect 1, wherein acquiring a 3D surface outline comprises:

scanning the subject by moving a scanning device around the subject at a fixed height, the scanning device remaining directed toward the subject while the scanning device moves around the subject.

3. The method according to any of the preceding aspects, representing the three-dimensional surface outline as a discretized mesh comprises creating from data of the 3D surface outline a 3D volume mesh.

4. The method according to any of the preceding aspects, wherein moving the scanning device around the subject comprises:

mounting the scanning device on one or more rails arranged to have curvilinear shape extending at least partially around the subject;

positioning the scanning device to maintain a view toward the subject;

positioning the subject within the curvilinear shape of the one or more rails; and moving the scanning device along the one or more rails to capture a plurality of measurements of the surface of the subject at each of a plurality of heights.

5. The method according to any of the preceding aspects, wherein using two or more probes of a probe assembly to acquire an optical signal at a surface of the subject comprises:

placing a first probe at a first point on a surface of the subject;

illuminating one or more first points on a face of the first probe;

receiving, via a first detector, data of a first optical signal from the subject; and receiving first tracking data, the first tracking data indicating a first 3D position and a first 3D orientation of the first probe, the first position and the first orientation corresponding to the data of the first optical signal.

6. The method according to any of the preceding aspects, wherein using two or more probes of a probe assembly to acquire an optical signal at a surface of the subject comprises:

placing a second probe at a second point on the surface of the subject;

illuminating one or more second points on a face of the second probe;

receiving, via a second detector, data of a second optical signal from the subject;

receiving second tracking data, the second tracking data indicating a second 3D position and a second 3D orientation of the second probe, the second position and the second orientation corresponding to the data of the second optical signal.

7. The method according to any of the preceding aspects, wherein co-registering to the mesh the image data to form an image comprises:
co-registering the data of the first optical signal and the first tracking data to the mesh.

8. The method according to any of the preceding aspects, wherein co-registering to the mesh the image data to form an image comprises:
co-registering the data of the second optical signal and the second tracking data to the mesh.

9. The method according to any of the preceding aspects, further comprising:
relocating a probe of the probe assembly to probe a second area of the subject to be imaged;
acquiring an optical signal from the second area of the subject;
receiving, via the imaging system, the optical signal acquired at the second area;
converting the optical signal acquired at the second area to image data of the second area; and
co-registering to the mesh the image data of the second area to form an image of the second area.

10. The method according to any of the preceding aspects, wherein acquiring an optical signal from the second area of the subject comprises:
placing the first probe at a third point on the surface of the subject;
illuminating one or more third points on the face of the first probe;
receiving, via the first detector, data of a third optical signal from the subject; and
receiving third tracking data, the third tracking data indicating a third 3D position and a third 3D orientation of the first probe, the third position and the third orientation corresponding to the data of the third optical signal.

11. The method according to any of the preceding aspects, wherein acquiring an optical signal from the second area of the subject comprises:
placing the second probe at a fourth point on the surface of the subject;
illuminating one or more fourth points on the face of the second probe;
receiving, via the second detector, data of a fourth optical signal from the subject; and
receiving fourth tracking data, the fourth tracking data indicating a fourth 3D position and a fourth 3D orientation of the second probe, the fourth position and the fourth orientation corresponding to data of the fourth optical signal.

12. The method according to any of the preceding aspects, wherein co-registering to the mesh the image data to form an image comprises:
co-registering the data of the third optical signal and the third tracking data to the mesh.

13. The method according to any of the preceding aspects, wherein co-registering to the mesh an image received from the probe comprises:
co-registering the data of the fourth optical signal and the fourth tracking data to the mesh.

14. The method according to any of the preceding aspects, wherein tracking one or more markers on each probe of the probe assembly comprises:
positioning on the first probe a first optical marking element having a first plurality of markers, each of the markers in the first optical marking element having a pre-determined, fixed relationship to one another;
positioning on the second probe a second optical marking element having a second plurality of markers, each of the markers in the second optical marking element having a predetermined, fixed relationship to one another; and
providing a tracking receiver to determine a position of each marker in each of the first and second optical marking elements.

15. The method according to any of the preceding aspects, further comprising tracking a marker on the subject.

16. The method according to any of the preceding aspects, wherein tracking a marker on the subject comprises positioning on the subject a third optical marking element having a third plurality of markers, each of the markers of the third optical marking element having a predetermined, fixed relationship to one another.

17. The method according to any of the preceding aspects, wherein providing a tracking receiver comprises providing a plurality of sensors having a pre-determined, fixed relationship to one another, each of the plurality of sensors operable to receive an optical signal from each marker of the optical marking element.

18. The method according to any of the preceding aspects, wherein tracking a marker comprises:
capturing on each of the plurality of sensors an image of each of the markers; and
determining, for each of the markers, using data from two or more of the plurality of sensors, a 3D location of the marker.

19. The method according to any of the preceding aspects, wherein determining a 3D location of the marker comprises determining the location with six degrees of freedom.

20. The method according to any of the preceding aspects, wherein receiving data of a first optical signal from the subject comprises receiving data generated by detecting, at an detector associated with a second probe, (i) illumination emitted from the first probe, or (ii) illumination emitted within the subject as a result of illumination emitted from the first probe.

21. The method according to any of the preceding aspects, wherein receiving data of a first optical signal from the subject comprises receiving data generated by detecting, at an detector associated with the first probe, (i) illumination emitted from the first probe, or (ii) illumination emitted within the subject as a result of illumination emitted from the first probe.

22. The method according to any of the preceding aspects, wherein tracking one or more markers on each probe of the probe assembly comprises:
capturing on a first sensor a first image of a first marker;
capturing on a second sensor positioned orthogonally to the first sensor a second image of the first marker;
determining a first set of coordinates specifying for the first image the location of the marker in the first image; and
determining a second set of coordinates specifying for the second image the location of the marker in the second image.

23. The method according to any of the preceding aspects, wherein tracking one or more markers on each probe of the probe assembly further comprises calculating for each sensor an offset parameter.

24. The method according to any of the preceding aspects, wherein calculating an offset parameter for one of the sensors comprises determining a distance, d, between the other of the sensors and the first marker, and subtracting from the distance, d, a value of one of the set of coordinates specifying the location of the first marker in the image for the one of the sensors, such that:

$$D1 = X2 + CAL2 \text{ and}$$

$$D2 = X1 + CAL1$$

where D1 is the distance between the first sensor and the first marker, D2 is the distance between the second sensor and the second marker, X1 is a first coordinate specifying the location of the first marker in the first image, X2 is a first coordinate specifying the location of the first marker in the second image, and CAL 1 and 2 are offset parameters for the first and second images, respectively.

25. A system for performing co-registered optical imaging, the system comprising:
an illumination assembly operable to output one or more optical signals;
a probe assembly optically coupled to the illumination assembly and operable to receive the one or more optical signals and to transmit the one or more optical signals into a subject tissue;
a tracking system comprising an optical marking element and a tracking receiver operable to detect the optical marking element, the tracking system communicatively coupled to a computing platform;
an imaging system coupled to the probe assembly and to the computing platform, the imaging system comprising an imaging sensor operable to receive an optical signal from the subject tissue;
a module executable by the computing platform to co-register tracking data received from the tracking system and image data received from the imaging system with a 3D mesh representing the subject tissue.

26. The system according to any of the preceding aspects, wherein the illumination assembly comprises:
a frequency synthesizer having a radio frequency (RF) output;
a radio frequency (RF) amplifier receiving a signal from the RF output of the frequency synthesizer and outputting an amplified signal; and
a RF splitter receiving the amplified signal and transmitting signals to each of a plurality of sources.

27. The system according to any of the preceding aspects, wherein the illumination assembly comprises:
a controller operable to control individually for each of a plurality of sources, the current and temperature of the source.

28. The system according to any of the preceding aspects, wherein each of the plurality of sources comprises a laser diode.

29. The system according to any of the preceding aspects, wherein the probe assembly comprises an optical coupling head operable to optically couple the probe assembly to the illumination assembly, such that each of a plurality of optical outputs disposed on a surface of a probe is optically coupled to an output of a corresponding one of the plurality of sources.

30. The system according to any of the preceding aspects, wherein the probe assembly comprises a first plurality of optical fibers arranged to deliver the one or more optical signals to a surface of the subject tissue.

31. The system according to any of the preceding aspects, wherein the probe assembly comprises first and second probes.

32. The system according to any of the preceding aspects, wherein the probe assembly comprises a second plurality of optical fibers arranged to deliver the optical signal from the subject tissue to the imaging sensor.

33. The system according to any of the preceding aspects, wherein the optical marking element of the tracking system comprises:
a plurality of light emitting diodes (LEDs) arranged such that each of the LEDs has a fixed, pre-determined positional relationship to each of the other LEDs in the plurality of LEDs.

34. The system according to any of the preceding aspects, wherein the tracking system comprises:
a first optical marking element disposed on the first probe; and
a second optical marking element disposed on the second probe.

35. The system according to any of the preceding aspects, wherein the tracking receiver comprises a plurality of tracking sensors, each of the tracking sensors having a fixed, pre-determined positional relationship to the other tracking sensors.

36. The system according to any of the preceding aspects, wherein the tracking receiver comprises a plurality of tracking sensors disposed orthogonally to one another.

37. The system according to any of the preceding aspects, wherein the tracking system comprises an optical marking element disposed in fixed positional relationship to the subject tissue.

38. The system according to any of the preceding aspects, wherein the module executable by the computing platform is further operable to receive data from the tracking receiver to determine one or both of a position and an orientation of the optical marking element.

39. The system according to any of the preceding aspects, wherein each probe of the probe assembly comprises a respective probe surface having an adjustably curvilinear contour.

40. The system according to any of the preceding aspects, wherein each probe of the probe assembly comprises a probe surface having disposed thereon a plurality of fiber ends coupled to the imaging system and a plurality of fiber ends coupled to the illumination assembly.

41. The system according to any of the preceding aspects, wherein each probe of the probe assembly comprises:
a plurality of planar probe surfaces coupled to one another, each of the probe surfaces having disposed thereon a plurality of fiber ends coupled to the imaging system and a plurality of fiber ends coupled to the illumination assembly;
an adjustment mechanism for adjusting the angles of the planar probe surfaces relative to one another, thereby allowing a contour of the probe to conform to subject tissue.

42. The system according to any of the preceding aspects, wherein a pliable material is attached to the plurality of planar probe surfaces to form a smooth contour over the plurality of planar probe surfaces 43. The system according to any of the preceding aspects, further comprising a contour scanning device operable to scan the subject tissue and to generate data of the surface of the subject tissue.

44. The system according to any of the preceding aspects, wherein the contour scanning device is movably mounted on a mechanical positioning device, the mechanical positioning device operable to move the contour scanning device along a predetermined path to scan the surface of the subject tissue from a plurality of angles.

45. The system according to any of the preceding aspects, wherein each of the contour scanning device and the mechanical positioning device is coupled to the computing platform.

46. The system according to any of the preceding aspects, wherein the module executable by the computing platform is further operable to receive data of the surface of the subject tissue and to generate a 3D mesh corresponding to the data.

47. The system according to any one of the preceding aspects, wherein each probe can contour to any tissue curvature.

48. The method or system according to any one of the preceding aspects, further comprising tracking the position of the subject to calibrate the probe's location during coregistration.

49. The method according to any one of the preceding aspects, further comprising keeping the first probe in the first position and moving the second probe to the second position.

50. The method or system according to any one of the preceding aspects, wherein each of the first and second detectors comprises a plurality of individual pixel sensors, and wherein the first and second detectors are disposed on a single integrated circuit device.

51. The method according to any one of the preceding aspects wherein the position of the first probe on the subject is static, and the position of the second probe on the subject is adjusted to acquire data from multiple locations.

52. The method according to any of the preceding aspects, further comprising calibrating a location of the probes relative to the 3D mesh using tracking data related to the position of the third optical marking element.

53. The method according to any of the preceding claims, wherein using two or more probes of a probe assembly to acquire an optical signal at a surface of the subject comprises using at least one probe having a probe surface with an adjustable contour.

We claim:

1. A method for performing co-registered optical imaging, the method comprising:
    acquiring a three-dimensional (3D) surface outline of a subject to be imaged;
    representing the 3D surface outline as a discretized mesh;
    using two or more probes of a probe assembly to acquire an optical signal at a surface of the subject, the two or more probes including a first probe and a second probe;
    tracking one or more markers on each of the two or more probes of the probe assembly to track a position and orientation of each of the two or more probes as the optical signal is acquired by (i) positioning on the first probe a first optical marking element having a first plurality of markers, each of the first plurality of markers having a predetermined, fixed relationship to one another, (ii) positioning on the second probe a second optical marking element having a second plurality of markers, each of the second plurality of markers having a predetermined, fixed relationship to one another, and (iii) providing a tracking receiver to determine a position and orientation of each marker in each of the first and second optical marking elements;
    receiving, via an imaging system coupled to the probe assembly, the optical signal acquired by the probe assembly;
    converting the optical signal to image data; and
    co-registering the image data to the discretized mesh in accordance with the tracked position and orientation of each of the two or more probes to form an image of the subject.

2. The method according to claim 1, further comprising:
    mounting a scanning device on one or more rails arranged to have curvilinear shape extending at least partially around the subject;
    positioning the scanning device to maintain a view toward the subject;
    positioning the subject within the curvilinear shape of the one or more rails; and
    moving the scanning device along the one or more rails to capture a plurality of measurements of the surface of the subject at each of a plurality of heights.

3. The method according to claim 1, wherein using the two or more probes of the probe assembly to acquire the optical signal at the surface of the subject comprises:
    placing a first probe at a first point on the surface of the subject;
    illuminating one or more first points on a face of the first probe; and
    receiving, via a first detector, data of a first optical signal from the subject, and wherein tracking one or more markers on each probe of the probe assembly further comprises:
    receiving first tracking data, the first tracking data indicating a first 3D position and a first 3D orientation of the first probe.

4. The method according to claim 3, wherein using the two or more probes of the probe assembly to acquire the optical signal at the surface of the subject comprises:
    placing a second probe at a second point on the surface of the subject;
    illuminating one or more second points on a face of the second probe; and
    receiving, via a second detector, data of a second optical signal from the subject, and wherein tracking one or more markers on each probe of the probe assembly further comprises;
    receiving second tracking data, the second tracking data indicating a second 3D position and a second 3D orientation of the second probe.

5. The method according to claim 3, wherein the first detector is associated with a second probe, and
    wherein receiving data of the first optical signal from the subject comprises receiving data generated by detecting, at the first detector, illumination emitted through the subject as a result of illumination emitted from the first probe.

6. The method according to claim 3, wherein the first detector is associated with the first probe, and
    wherein receiving data of the first optical signal from the subject comprises receiving data generated by detecting, at the first detector, illumination emitted through the subject as a result of illumination emitted from the first probe.

7. The method according to claim 1, further comprising:
    relocating one of the two or more probes of the probe assembly to probe a second area of the subject;
    receiving, via the imaging system, a second optical signal acquired at a second area of the subject;
    converting the second optical signal to second image data of the second area; and
    co-registering the second image data to the discretized mesh in accordance with the tracked position and orientation of the relocated one of the two or more probes to form an image of the second area.

8. The method according to claim 1, wherein providing a tracking receiver comprises:

providing a plurality of sensors having a pre-determined, fixed relationship to one another, each of the plurality of sensors receiving a tracking optical signal from each marker in each of the first and second optical marking elements.

9. The method according to claim 8, further comprising:
determining, for each of the markers, a 3D location and orientation of the markers in each of the first and second optical marking elements using the tracking optical signal from each of the markers.

10. The method according to claim 1, wherein tracking the one or more markers further comprises:
tracking the one or more markers on the subject.

11. The method according to claim 10, wherein tracking the one or more markers on the subject comprises:
positioning on the subject a first optical marking element having a first plurality of markers, each of the first plurality of markers having a predetermined, fixed relationship to one another;
positioning on the subject a second optical marking element having a second plurality of markers, each of the second plurality of markers having a predetermined, fixed relationship to one another;
positioning on the subject a third optical marking element having a third plurality of markers, each of the third plurality of markers having a predetermined, fixed relationship to one another; and
providing a tracking receiver to determine a position and orientation of each marker in each of the first, second, and third optical marking elements.

12. The method according to claim 1, wherein tracking one or more markers on each of the two or more probes of the probe assembly comprises:
determining a first set of coordinates specifying the location of the first optical marking element; and
determining a second set of coordinates specifying the location of the second optical marking element.

13. A method for performing co-registered optical imaging, the method comprising:
acquiring a three-dimensional (3D) surface outline of a subject to be imaged;
representing the 3D surface outline as a discretized mesh;
using two or more probes of a probe assembly to acquire an optical signal at a surface of the subject;
tracking one or more markers on each of the two or more probes of the probe assembly to track a position and orientation of each of the two or more probes as the optical signal is acquired to track the one or more markers on the subject by (i) positioning on the subject a first optical marking element having a first plurality of markers, each of the first plurality of markers having a predetermined, fixed relationship to one another, (ii) positioning on the subject a second optical marking element having a second plurality of markers, each of the second plurality of markers having a predetermined, fixed relationship to one another, (iii) positioning on the subject a third optical marking element having a third plurality of markers, each of the third plurality of markers having a predetermined, fixed relationship to one another, and (iv) providing a tracking receiver to determine a position and orientation of each marker in each of the first, second, and third optical marking elements;
receiving, via an imaging system coupled to the probe assembly, the optical signal acquired by the probe assembly;
converting the optical signal to image data; and
co-registering the image data to the discretized mesh in accordance with the tracked position and orientation of each of the two or more probes to form an image of the subject.

14. The method according to claim 13, further comprising:
mounting a scanning device on one or more rails arranged to have curvilinear shape extending at least partially around the subject;
positioning the scanning device to maintain a view toward the subject;
positioning the subject within the curvilinear shape of the one or more rails; and
moving the scanning device along the one or more rails to capture a plurality of measurements of the surface of the subject at each of a plurality of heights.

15. The method according to claim 13, wherein using the two or more probes of the probe assembly to acquire the optical signal at the surface of the subject comprises:
placing a first probe at a first point on the surface of the subject;
illuminating one or more first points on a face of the first probe; and
receiving, via a first detector, data of a first optical signal from the subject, and wherein tracking one or more markers on each probe of the probe assembly further comprises:
receiving first tracking data, the first tracking data indicating a first 3D position and a first 3D orientation of the first probe.

16. The method according to claim 15, wherein using the two or more probes of the probe assembly to acquire the optical signal at the surface of the subject comprises:
placing a second probe at a second point on the surface of the subject;
illuminating one or more second points on a face of the second probe; and
receiving, via a second detector, data of a second optical signal from the subject, and wherein tracking one or more markers on each probe of the probe assembly further comprises;
receiving second tracking data, the second tracking data indicating a second 3D position and a second 3D orientation of the second probe.

17. The method according to claim 15, wherein the first detector is associated with a second probe, and
wherein receiving data of the first optical signal from the subject comprises receiving data generated by detecting, at the first detector, illumination emitted through the subject as a result of illumination emitted from the first probe.

18. The method according to claim 15, wherein the first detector is associated with the first probe, and
wherein receiving data of the first optical signal from the subject comprises receiving data generated by detecting, at the first detector, illumination emitted through the subject as a result of illumination emitted from the first probe.

19. The method according to claim 13, further comprising:
relocating one of the two or more probes of the probe assembly to probe a second area of the subject;

receiving, via the imaging system, a second optical signal acquired at a second area of the subject;

converting the second optical signal to second image data of the second area; and co-registering the second image data to the discretized mesh in accordance with the tracked position and orientation of the relocated one of the two or more probes to form an image of the second area.

20. The method according to claim 13, wherein providing a tracking receiver comprises:

providing a plurality of sensors having a pre-determined, fixed relationship to one another, each of the plurality of sensors receiving a tracking optical signal from each marker of each of the first and second optical marking elements.

21. The method according to claim 20, further comprising:

determining, for each of the markers, a 3D location and orientation of the markers in each of the first and second optical marking elements using the tracking optical signal from each of the markers.

22. The method according to claim 13, wherein tracking one or more markers on each of the two or more probes of the probe assembly comprises:

determining a first set of coordinates specifying the location of the first optical marking element; and determining a second set of coordinates specifying the location of the second optical marking element.

23. A method for performing co-registered optical imaging, the method comprising:

acquiring a three-dimensional (3D) surface outline of a subject to be imaged;

representing the 3D surface outline as a discretized mesh;

using at least one probe of a probe assembly to acquire an optical signal at a surface of the subject;

tracking one or more markers on the at least one probe of the probe assembly to track a position and orientation of each the at least one probe as the optical signal is acquired to track the one or more markers on the subject by (i) positioning on the subject a first optical marking element having a first plurality of markers, each of the first plurality of markers having a predetermined, fixed relationship to one another, (ii) positioning on the subject a second optical marking element having a second plurality of markers, each of the second plurality of markers having a predetermined, fixed relationship to one another, (iii) positioning on the subject a third optical marking element having a third plurality of markers, each of the third plurality of markers having a predetermined, fixed relationship to one another, and (iv) providing a tracking receiver to determine a position and orientation of each marker in each of the first, second, and third optical marking elements;

receiving, via an imaging system coupled to the probe assembly, the optical signal acquired by the probe assembly;

converting the optical signal to image data; and co-registering the image data to the discretized mesh in accordance with the tracked position and orientation of each of the one or more probes to form an image of the subject.

* * * * *

UNITED STATES PATENT AND TRADEMARK OFFICE
CERTIFICATE OF CORRECTION

PATENT NO. : 9,635,349 B2
APPLICATION NO. : 13/703270
DATED : April 25, 2017
INVENTOR(S) : Anuradha Godavarty et al.

It is certified that error appears in the above-identified patent and that said Letters Patent is hereby corrected as shown below:

In the Specification

In Column 1, Line 22, delete "R15-CA119253" and insert -- R15 CA119253 --.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*